United States Patent [19]

Reiffenrath et al.

[11] Patent Number: 5,536,442
[45] Date of Patent: * Jul. 16, 1996

[54] FLUORINATED LIQUID CRYSTAL COMPOUNDS AND LIQUID CRYSTAL MEDIUM CONTAINING SAME

[75] Inventors: Volker Reiffenrath, Rossdorf; Hans A. Kurmeier, Seeheim-Jugenheim; Eike Poetsch, Mühltal; Herbert Plach, Darmstadt; Ulrich Finkenzeller, Plankstadt; Ekkehard Bartmann, Erzhausen; Joachim Krause, Dieburg; Bernhard Scheuble, Seeheim-Jugenheim; Dieter Dorsch, Darmstadt; Georg Weber, Erzhausen, all of Germany

[73] Assignee: Merck Patent Gesellschaft Mit Beschrankter Haftung, Darmstadt, Germany

[ * ] Notice: The term of this patent shall not extend beyond the expiration date of Pat. No. 5,409,637.

[21] Appl. No.: 907,928

[22] Filed: Jul. 6, 1992

Related U.S. Application Data

[63] Continuation-in-part of Ser. No. 846,230, Mar. 6, 1992, abandoned, and a continuation-in-part of Ser. No. 623,385, Nov. 19, 1990, abandoned, and a continuation-in-part of Ser. No. 845,818, Mar. 9, 1992, Pat. No. 5,389,292, which is a continuation of Ser. No. 424,219, Oct. 4, 1989, abandoned, and a continuation-in-part of Ser. No. 803,787, Dec. 6, 1991, abandoned, which is a continuation of Ser. No. 362,438, May 24, 1989, abandoned.

[30] Foreign Application Priority Data

| Sep. 25, 1987 | [DE] | Germany | 37 32 284.2 |
| Jul. 27, 1988 | [DE] | Germany | 38 25 425.5 |
| Mar. 24, 1989 | [DE] | Germany | 39 09 802.8 |
| Sep. 6, 1989 | [DE] | Germany | 39 29 526.5 |
| Sep. 6, 1989 | [DE] | Germany | 39 29 525.7 |
| Sep. 7, 1989 | [DE] | Germany | 39 29 764.0 |
| Mar. 28, 1990 | [DE] | Germany | 40 09 907.5 |

[51] Int. Cl.$^6$ .......... C09K 19/52; C07C 25/13; C07D 238/02; C07D 319/06; C02F 1/13

[52] U.S. Cl. .......... 252/299.01; 252/299.61; 252/299.62; 252/299.63; 252/299.66; 252/299.67; 570/127; 544/334; 549/369; 560/55; 560/65; 359/103

[58] Field of Search .......... 252/299.01, 299.61, 252/299.62, 299.63, 299.64, 299.65, 299.66, 299.67; 359/103, 104; 570/127; 544/334; 549/369, 374; 560/55, 65

[56] References Cited

U.S. PATENT DOCUMENTS

| 3,506,718 | 4/1970 | Mutsch . | |
| 3,998,972 | 12/1976 | Farooq et al. . | |
| 4,048,235 | 9/1977 | Karrer . | |
| 4,199,595 | 4/1980 | Berkelhammer et al. | 568/655 |
| 4,393,231 | 7/1983 | Misaki et al. . | |
| 4,415,470 | 11/1983 | Eidenschink et al. . | |
| 4,512,636 | 4/1985 | Andrews et al. . | |
| 4,617,140 | 10/1986 | Eidenschink et al. . | |
| 4,630,897 | 12/1986 | Andrews et al. . | |
| 4,678,811 | 7/1987 | Franke et al. . | |
| 4,709,030 | 11/1987 | Petrzilka et al. . | |
| 4,726,911 | 2/1988 | Krause et al. . | |
| 4,822,519 | 4/1989 | Saito et al. . | |
| 4,871,470 | 10/1989 | Wächtler et al. . | |
| 4,874,545 | 10/1989 | Heppke et al. . | |
| 4,877,548 | 11/1989 | Kitano et al. . | |
| 4,880,562 | 11/1989 | Kitano et al. . | |
| 4,886,619 | 12/1989 | Janulis . | |
| 4,886,620 | 12/1989 | Hopf et al. . | |
| 4,886,621 | 12/1989 | Sage et al. . | |
| 4,911,863 | 3/1990 | Sage et al. . | |
| 5,032,313 | 7/1991 | Goto et al. . | |
| 5,045,229 | 9/1991 | Bartmann et al. . | |
| 5,082,587 | 1/1992 | Janulis . | |
| 5,122,295 | 6/1992 | Weber et al. . | |
| 5,171,469 | 12/1992 | Hittich et al. | 252/299.01 |
| 5,178,790 | 1/1993 | Weber et al. | 252/299.01 |
| 5,368,772 | 11/1994 | Rieger et al. | 252/299.63 |
| 5,372,746 | 12/1994 | Buchecker et al. | 252/299.61 |
| 5,389,292 | 2/1995 | Dorsch et al. | 252/299.61 |
| 5,409,637 | 4/1995 | Rieger et al. | 252/299.63 |

FOREIGN PATENT DOCUMENTS

| 0193191 | 9/1986 | European Pat. Off. . |
| 0387032 | 9/1990 | European Pat. Off. . |
| 3511111 | 10/1986 | Germany . |
| 3906040 | 9/1989 | Germany . |
| 55-157523 | 12/1980 | Japan . |
| 58-18326 | 2/1983 | Japan . |
| 2162515 | 2/1986 | United Kingdom . |
| 88/08441 | 11/1988 | WIPO . |

OTHER PUBLICATIONS

Titov et al., Mol. Cryst. Liq. Cryst., vol. 47, pp. 1–5 (1978).
Rieger et al., "Bulk Resistivity of Liquid Crystals and their RC–Time Constant in Displays", Presentation No. 16 at Freiburger Arbeidstagung 1989, Conference Proceedings, Frieburg (1989).
Finkenzeller et al., "Physical Properties of Liquid Crystals: III. Dielectric Permittivities." Liquid Crystal Newsletter 4, Merck (1989).

*Primary Examiner*—Shean C. Wu
*Attorney, Agent, or Firm*—Millen, White, Zelano & Branigan

[57] ABSTRACT

The invention relates to liquid crystal compounds having a terminal structure in accordance with formula 1, 2, 3 or 4:

| $-A^3-OCF_3$ | 1 |
| $-A^2-Q-CHF_2$ | 2 |
| $-3,5$-difluoro-1,4-phenylene-$X^1$ | 3 |
| $-3$-fluoro-1,4-phenylene-$X^2$ | 4 | wherein $A^2$, $A^3$, $X^1$ and $X^2$ and are defined herein. The invention further relates liquid crystal phases containing the above components as well as electrooptical displays containing same.

16 Claims, No Drawings

FLUORINATED LIQUID CRYSTAL COMPOUNDS AND LIQUID CRYSTAL MEDIUM CONTAINING SAME

CROSS-REFERENCE TO RELATED APPLICATIONS

This application is a continuation-in-part of Ser. No. 07/846,230, filed Mar. 6, 1992, now abandoned; a continuation-in-part of Ser. No. 07/623,385, now abandoned, filed Nov. 19, 1990; a continuation-in-part of Ser. No. 07/845,818, filed Mar. 9, 1992, now U.S. Pat. No. 5,389,292, which is a continuation of Ser. No. 07/424,219, now abandoned, filed Oct. 4, 1989; and a continuation-in-part of Ser. No. 07/803,787, filed Dec. 6, 1991, now abandoned which is a continuation of Ser. No. 07/362,438, filed May 24, 1989, now abandoned. The entire disclosures of all six of the above-mentioned applications are hereby incorporated by reference.

Also hereby incorporated by reference are the entire disclosures of International Applications PCT/EP88/00804, filed Sep. 5, 1988; PCT/EP89/00821, filed Jul. 26, 1989; and PCT/EP90/01471, filed Sep. 3, 1990. Furthermore, also hereby incorporated by reference are the entire disclosures of German Patent Applications P 37 32 284.2, filed Sep. 25, 1987; P 38 25 425.5, filed Jul. 27, 1988; P 39 09 802.8, filed Mar. 24, 1989; P 39 29 525.7, filed Sep. 6, 1989; P 39 29 526.5, filed Sep. 6, 1989; P 39 29 764.0, filed Sep. 7, 1989; P 40 09 907.5, filed Mar. 28, 1990; and DE 40 27 840A1.

SUMMARY OF THE INVENTION

The invention relates to fluorinated liquid crystal compounds, particularly fluorobenzene derivatives, and their use in liquid crystalline media. The fluoro-benzene liquid crystal compounds have a terminal structure in accordance with the formula 1, 2, 3 or 4:

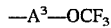    1 wherein $A^3$ is a 1,4-phenylene group which is substituted by one or two F atoms;

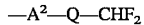    2 wherein $A^2$ is 3-fluoro-1,4-phenylene or 3,5-difluoro-1,4-phenylene and Q is —O— or a single bond;

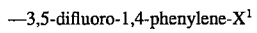    3 wherein $X^1$ is —$CF_3$, —$CF_2Cl$, —$OCF_2Cl$ or —$OCHFCl$; or

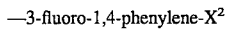    4 wherein $X^2$ is —$CF_3$, —$CF_2Cl$, —$OCF_2Cl$ or —$OCHFCl$.

The fluorobenzene liquid crystal compounds of the invention possess a central portion having at least two optionally substituted rings, all rings optionally being separated from each other by a bridging group, and the central portion is bonded at each end to a wing group. At least one terminal portion of the compound is a structure in accordance with formulae 1, 2, 3, or 4.

Compounds of Formula 1 as well as their preparation and use, are disclosed in Ser. No. 07/362,438 and its continuation Ser. No. 07/803,787. Compounds of Formula 2, their preparation and their use are disclosed in Ser. No. 07/424,219. In addition, compounds of formulas 3 and 4, their preparation and their use are disclosed in Ser. No. 07/623,385.

The invention furthermore relates to the use of the above-described compounds as components of liquid-crystalline media and to liquid-crystalline electrooptical display elements containing liquid crystal media according to the invention. The compounds of formulae 1, 2, 3 and 4 can be used as components of liquid crystal media, in particular for displays based on the principle of the twisted cell, the guest-host effect, the effect of the deformation of aligned phases or the effect of dynamic scattering.

An object of the invention is therefore to provide new stable liquid-crystalline or mesogenic compounds which are suitable as components of liquid-crystalline phases and, in particular, have a comparably low viscosity and a relatively high dielectric anisotropy.

Upon further study of the specification and appended claims, further objects and advantages of this invention will become apparent to those skilled in the art.

It has now been found that the compounds of formulae 1, 2, 3 and 4 are highly suitable as components of liquid crystalline media. In particular, they have comparatively low viscosities. They can be used to obtain stable liquid-crystalline phases having a broad mesogenic range and advantageous values for optical and dielectrical anisotropy.

In formula 1 above, $A^3$ is preferably a —3-fluoro-1,4-phenylene group.

The compounds of the formulae 1, 2, 3 and 4 are prepared by methods known per se, as described in the literature (for example in the standard works such as Houben-Weyl, Methoden der Organischen Chemie, [Methods of Organic Chemistry], Georg-Thieme-Verlag, Stuttgart, namely under the reaction conditions which are known and suitable for the reactions mentioned. Variants which are known per se, but not described here in greater detail, can also be used here.

The liquid-crystalline phases according to the invention generally comprise 2 to 40, preferably 4 to 30, components, including at least one compound of formulae 1, 2, 3 or 4. The other components are selected from nematic or nematogenic substances, in particular the known substances from the classes comprising the azoxybenzenes, benzylideneanilines, biphenyls, terphenyls, phenyl or cyclohexylbenzoates, phenyl or cyclohexyl cyclohexanoates, phenyl cyclohexanes, cyclohexylbiphenyls, cyclohexylcyclohexanes, cyclohexylnaphthalenes, 1,4-biscyclohexylbenzenes, 4,4'-biscyclohexylbiphenyls, phenyl- or cyclohexylpyrimidines, phenyl- or cyclohexyldioxanes, phenyl- or cyclohexyldithianes, 1,2-bisphenylethanes, 1,2-biscyclohexylethanes, 1-phenyl-2-cyclohexylethanes, optionally halogenated stilbenes, benzyl phenyl ethers, tolanes and substituted cinnamic acids.

The most important compounds which are suitable as components of liquid-crystalline phases of this type may be characterized by the formula

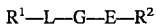

in which L and E are each a carbocyclic or heterocyclic ring system from the group formed from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

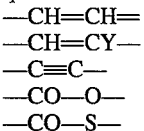

—CH=N—
—N(O)=N—
—CH=N(O)—
—CH$_2$—CH$_2$—
—CH$_2$—O—
—CH$_2$—S—
—COO—Phe—COO or a C—C single bond, Y is halogen, preferably chlorine, or —CN, and R$^1$ and R$^2$ are alkyl, alkoxy, alkanoyloxy or alkoxycarbonyloxy having up to 18, preferably up to 8, carbon atoms, or one of these radicals is alternatively CN, NO$_2$, CF$_3$, F, Cl or Br.

In most of these compounds, R$^1$ and R$^2$ are different from one another, one of these radicals usually being an alkyl or alkoxy group. However, other variants of the proposed substituents are common. Many such substances or mixtures thereof are commercially available. All these substances can be prepared by methods known from the literature. The invention further relates to substituted phenyl trifluoromethyl ethers of the formula I $$R^1—(A^1—Z^1)_n—A^2—Z^2—A^3—OCF_3 \quad\quad I$$

in which
R$^1$ is H or alkyl having 1–18 C atoms in which one or more CH$_2$ groups may also be replaced by —E—, —O—, —S— and/or —CO—, where two heteroatoms are not linked directly to one another, or perfluoroalkyl having 1–18 C atoms in which one or more CF$_2$ groups may also be replaced by —CH$_2$—, —E—, —O—, —S— and/or —CO—, where two heteroatoms are not linked directly to one another,
E is CH=CX, CX=CH, C≡C, CHY,

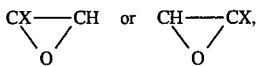

X is Y, CH$_3$ or H,
Y is CN, NCS, NCO or halogen,
A$^1$ and A$^2$, independently of one another, are each 1,4-cyclohexylene, in which one or two non-adjacent CH$_2$ groups may also be replaced by —O— and/or S atoms, 1,4-cyclohexenylene, 1,4-bicyclo(2.2.2)octylene, piperidine-1,4-diyl or 1,4-phenylene in which one or more CH groups may be replaced by N, which is unsubstituted or monosubstituted or polysubstituted by halogen atoms and/or CN and/or CH$_3$ groups,
Z$^1$ and Z$^2$ are each —CO—O—, —O—CO—, —CH$_2$O—, —OCH$_2$—, —CH$_2$CH$_2$—, —CH=CH— or a single bond,
A$^3$ is a 1,4-phenylene group which is unsubstitued or monosubstituted or polysubstituted by halogen atoms and/or CN and/or CH$_3$ groups and
n is 0, 1 or 2,
with the proviso that Z$^2$ is —CH$_2$O—, —OCH$_2$—, —CH$_2$CH$_2$—, —CH=CH— or a single bond in the case where n=0 or 1, R$^1$=alkoxy and A$^1$=A$^2$=A$^3$=unsubstituted 1,4-phenylene, and to the use thereof as components in liquid-crystalline phases.

For reasons of simplicity, Cyc is a 1,4-cyclohexylene group, Che is a 1,4-cyclohexenylene group, Dio is a 1,3-dioxane-2,5-diyl group, Dit is a 1,3-dithiane-2,5-diyl group, Phe is a 1,4-phenylene group, Pyd is a pyridine-2,5-diyl group, Pyr is a pyrimidine-2,5-diyl group and Bi is a bicyclo(2,2,2)octylene group, where Cyc and/or Phe may be unsubstituted or substituted by one or more halogen atoms and/or CH$_3$ groups and/or CN groups.

The compounds of the formula I can be used as components in liquid-crystalline phases, in particular for displays which are based on the principle of the twisted cell, the guest/host effect, the effect of deformation of aligned phases or the effect of dynamic scattering.

It has now been found that compounds of the formula I are highly suitable as components of liquid-crystalline phases. In particular, they have comparatively low viscosities. They can be used to obtain stable liquid-crystalline phases having a broad meso-phase range and advantageous values for optical and dielectrical anisotropy.

In addition, the provision of compounds of the formula I considerably extends, very generally, the range of liquid-crystalline substances which are suitable, from various applicational points of view, for the production of liquid-crystalline mixtures.

The compounds of the formula I have a broad field of application. Depending on the choice of substituents, these compounds can be used as base materials of which liquid-crystalline phases are predominantly composed, or compounds of the formula I can be added to liquid-crystalline base materials made of other classes of compounds in order, for example, to influence the dielectrical and/or optical anisotropy of a dielectric of this type and/or to optimize its threshold voltage and/or its viscosity.

The compounds of the formula I are colorless in the pure state and form liquid-crystalline mesophases in a temperature range which is favorable for electro-optical use. They are stable chemically, thermally and against light.

The invention thus relates to the compounds of the formula I and to the use of these compounds as components of liquid-crystalline phases. The invention furthermore relates to liquid-crystalline phases containing at least one compound of the formula I and to liquid-crystal display elements, in particular electro-optical display elements, which contain such phases.

Above and below, R$^1$, A$^1$, Z$^1$, n, A$^2$, Z$^2$ and A$^3$ of formula I and its subformulae have the meaning indicated, unless expressly stated otherwise.

The compounds of the formula I accordingly cover compounds containing two rings of the sub-formulae Ia and Ib:

| | |
|---|---|
| R$^1$—A$^2$—A$^3$—OCF$_3$ | Ia |
| R$^1$—A$^2$—Z$^2$—A$^3$—OCF$_3$ | Ib | compounds containing three rings of the sub-formulae Ic to If:

| | |
|---|---|
| R$^1$—A$^1$—A$^2$—A$^3$—OCF$_3$ | Ic |
| R$^1$—A$^1$—Z$^1$—A$^2$—Z$^2$—A$^3$—OCF$_3$ | Id |
| R$^1$—A$^1$—Z$^1$—A$^2$—A$^3$—OCF$_3$ | Ie |
| R$^1$—A$^1$—A$^2$—Z$^2$—A$^3$—OCF$_3$ | If | and compounds containing four rings of the sub-formulae Ig to In:

| | |
|---|---|
| R$^1$—A$^1$—A$^1$—A$^2$—A$^3$—OCF$_3$ | Ig |
| R$^1$—A$^1$—Z$^1$—A$^1$—A$^2$—A$^3$—OCF$_3$ | Ih |
| R$^1$—A$^1$—A$^1$—Z$^1$—A$^2$—A$^3$—OCF$_3$ | Ii |
| R$^1$—A$^1$—A$^1$—A$^2$—Z$^2$—A$^3$—OCF$_3$ | Ij |
| R$^1$—A$^1$—Z$^1$—A$^1$—Z$^1$—A$^2$—A$^3$—OCF$_3$ | Ik |
| R$^1$—A$^1$—Z$^1$—A$^1$—A$^2$—Z$^2$—A$^3$—OCF$_3$ | Il |
| R$^1$—A$^1$—A$^1$—Z$^1$—A$^2$—Z$^2$—A$^3$—OCF$_3$ | Im |
| R$^1$—A$^1$—Z$^1$—A$^1$—Z$^1$—A$^2$—Z$^2$—A$^3$—OCF$_3$ | In |

Of these, those of the sub-formulae Ia, Ib, Ic, Id, Ie, If, Ih, Ij and II are particularly preferred.

The preferred compounds of the sub-formula Ia cover those of the sub-formulae Iaa to Iaf:

| | |
|---|---|
| $R^1$—Phe—Phe—$OCF_3$ | Iaa |
| $R^1$—Dio—Phe—$OCF_3$ | Iab |
| $R^1$—Pyr—Phe—$OCF_3$ | Iac |
| $R^1$—Pyd—Phe—$OCF_3$ | Iad |
| $R^1$—Cyc—Phe—$OCF_3$ | Iae |
| $R^1$—Che—Phe—$OCF_3$ | Iaf |

Of these, those of the formulae Iaa, Iab, Iad and Iae are particularly preferred.

The preferred compounds of the sub-formula Ib cover those of the sub-formulae Iba to Ibl:

| | |
|---|---|
| $R^1$—Phe—$CH_2CH_2$—Phe—$OCF_3$ | Iba |
| $R^1$—Phe—$OCH_2$—Phe—$OCF_3$ | Ibb |
| $R^1$—Cyc—$CH_2CH_2$—Phe—$OCF_3$ | Ibc |
| $R^1$—Cyc—OCO—Phe—$OCF_3$ | Ibd |
| $R^1$—$A^2$—$CH_2CH_2$—Phe—$OCF_3$ | Ibe |
| $R^1$—$A^2$—$CH_2O$—Phe—$OCF_3$ | Ibf |
| $R^1$—$A^2$—$OCH_2$—Phe—$OCF_3$ | Ibg |
| $R^1$—$A^2$—COO—Phe—$OCF_3$ | Ibh |
| $R^1$—$A^2$—OCO—Phe—$OCF_3$ | Ibi |
| $R^1$—Che—$CH_2CH_2$—Phe—$OCF_3$ | Ibj |
| $R^1$—Phe—OCO—Phe—$OCF_3$ | Ibk |
| $R^1$—Cyc—COO—Phe—$OCF_3$ | Ibl |

The preferred compounds of the sub-formula Ic cover those of the sub-formulae Ica to Ici:

| | |
|---|---|
| $R^1$—Phe—Phe—Phe—$OCF_3$ | Ica |
| $R^1$—Phe—Dio—Phe—$OCF_3$ | Icb |
| $R^1$—Cyc—Cyc—Phe—$OCF_3$ | Icc |
| $R^1$—Pyd—Phe—Phe—$OCF_3$ | Icd |
| $R^1$—Pyr—Phe—Phe—$OCF_3$ | Ice |
| $R^1$—Cyc—Phe—Phe—$OCF_3$ | Icf |
| $R^1$—Dio—Phe—Phe—$OCF_3$ | Icg |
| $R^1$—Che—Phe—Phe—$OCF_3$ | Ich |
| $R^1$—Phe—Che—Phe—$OCF_3$ | Ici |

Of these, those of the formulae Icc and Icf are particularly preferred.

The preferred compounds of the sub-formula Id cover those of the sub-formulae Ida to Idk:

| | |
|---|---|
| $R^1$—Phe—$Z^1$—Phe—$Z^2$—Phe—$OCF_3$ | Ida |
| $R^1$—Phe—$Z^1$—Dio—$Z^2$—Phe—$OCF_3$ | Idb |
| $R^1$—Cyc—$Z^1$—Cyc—$Z^2$—Phe—$OCF_3$ | Idc |
| $R^1$—Pyd—$Z^1$—Phe—$Z^2$—Phe—$OCF_3$ | Ide |
| $R^1$—Phe—$Z^1$—Pyd—$Z^2$—Phe—$OCF_3$ | Idf |
| $R^1$—Pyr—$Z^1$—Phe—$Z^2$—Phe—$OCF_3$ | Idg |
| $R^1$—Phe—$Z^1$—Pyr—$Z^2$—Phe—$OCF_3$ | Idh |
| $R^1$—Phe—$Z^1$—Cyc—$Z^2$—Phe—$OCF_3$ | Idi |
| $R^1$—Dio—$Z^1$—Phe—$Z^2$—Phe—$OCF_3$ | Idj |
| $R^1$—Che—$Z^1$—Phe—$Z^2$—Phe—$OCF_3$ | Idk |

The preferred compounds of the sub-formula Ie cover those of the sub-formulae Iea to Iei:

| | |
|---|---|
| $R^1$—Pyr—$Z^1$—Phe—Phe—$OCF_3$ | Iea |
| $R^1$—Dio—$Z^1$—Phe—Phe—$OCF_3$ | Ieb |
| $R^1$—Cyc—$Z^1$—Phe—Phe—$OCF_3$ | Iec |
| $R^1$—Phe—$Z^1$—Cyc—Phe—$OCF_3$ | Ied |
| $R^1$—Cyc—$Z^1$—Cyc—Phe—$OCF_3$ | Iee |
| $R^1$—Phe—$Z^1$—Dio—Phe—$OCF_3$ | Ief |
| $R^1$—Pyd—$Z^1$—Phe—Phe—$OCF_3$ | Ieg |
| $R^1$—Phe—$Z^1$—Pyr—Phe—$OCF_3$ | Ieh |
| $R^1$—Phe—$Z^1$—Che—Phe—$OCF_3$ | Iei |

The preferred compounds of the sub-formula If cover those of the sub-formulae Ifa to Ifm:

| | |
|---|---|
| $R^1$—Pyr—Phe—$Z^2$—Phe—$OCF_3$ | Ifa |
| $R^1$—Pyr—Phe—$OCH_2$—Phe—$OCF_3$ | Ifb |
| $R^1$—Phe—Phe—$Z^2$—Phe—$OCF_3$ | Ifc |
| $R^1$—Cyc—Cyc—$Z^2$—Phe—$OCF_3$ | Ifd |
| $R^1$—Cyc—Cyc—$CH_2CH_2$—Phe—$OCF_3$ | Ife |
| $R^1$—Pyd—Phe—$Z^2$—Phe—$OCF_3$ | Iff |
| $R^1$—Dio—Phe—$Z^2$—Phe—$OCF_3$ | Ifg |
| $R^1$—Pyr—Cyc—$Z^2$—Phe—$OCF_3$ | Ifh |
| $R^1$—Pyr—Pyd—$Z^2$—Phe—$OCF_3$ | Ifi |
| $R^1$—Che—Phe—$Z^2$—Phe—$OCF_3$ | Ifj |
| $R^1$—Phe—Che—$Z^2$—Phe—$OCF_3$ | Ifk |
| $R^1$—Pyr—Phe—$CH_2CH_2$—Phe—$OCF_3$ | Ifl |
| $R^1$—Cyc—Phe—$CH_2CH_2$—Phe—$OCF_3$ | Ifm |

The preferred compounds of the sub-formulae Ig to In cover those of the sub-formulae Io to Iv:

| | |
|---|---|
| $R^1$—Cyc—Cyc—Phe—Phe—$OCF_3$ | Io |
| $R^1$—$A^1$—$CH_2O$—$A^1$—$A^2$—Phe—$OCF_3$ | Ip |
| $R^1$—Cyc—Cyc—$Z^1$—$A^2$—Phe—$OCF_3$ | Iq |
| $R^1$—$A^1$—$A^1$—$A^2$—$CH_2CH_2$—Phe—$OCF_3$ | Ir |
| $R^1$—Phe—$Z^1$—Phe—$Z^1$—Dio—Phe—$OCF_3$ | Is |
| $R^1$—Phe—$Z^1$—Phe—Phe—$Z^2$—Phe—$OCF_3$ | It |

R¹—A¹—COO—A¹—Coo—A²—Phe—OCF₃   Iu

R¹—A¹—A¹—COO—A²—Z²—Phe—OCF₃   Iv

In the compounds of the formulae I, Ia–Iv, Iaa–Iaf, Iba–Ibl, Ica–Ici, Ida–Idk, Iea–Iei, and Ifa–Ifm, R¹ is preferably alkyl, furthermore alkoxy. A¹ and A² are preferably Phe, Cyc, Che, Pyd, Pyr or Dio. The compounds of the formula I preferably contain no more than one of the radicals Bi, Pyd, Pyr, Dio and Dit.

R¹ is preferably also an alkyl group in which two adjacent CH₂ groups have been replaced by —O— and —CO— or —CO— and —O—. Furthermore, R¹ is preferably an alkyl group in which one CH₂ group has been replaced by —C≡C— or —CH=CH—.

Preferred compounds of the formula I and of all the subformulae thereof are also those in which A¹ and/or is A² (are) 1,4-phenylene which is substituted by one or more F atoms.

Z¹ and Z² of formula I and its subformulae are preferably single bonds, and secondarily preferably —CH₂CH₂—, —CH₂O— or —OCH₂—. Furthermore, the groups —COO—, —OCO— or —CH=CH— are preferred for Z¹ and Z².

A³ of formula I and its subformulae is preferably a 1,4-phenylene group which is unsubstituted or substituted by one or two F atoms.

The following compounds of the formulae 1' to 13' are particularly preferred of the laterally substituted compounds of formula I.

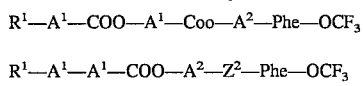

1'

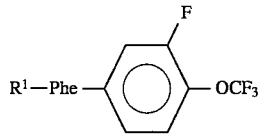

2'

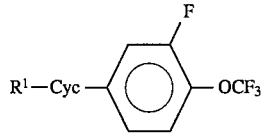

3'

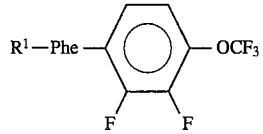

4'

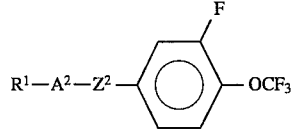

5'

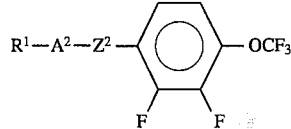

6'

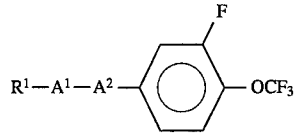

7'

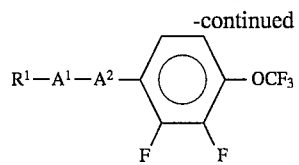

8'

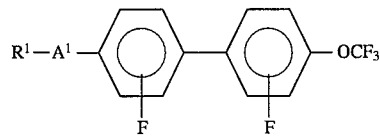

9'

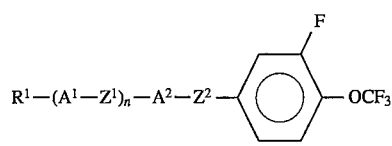

10'

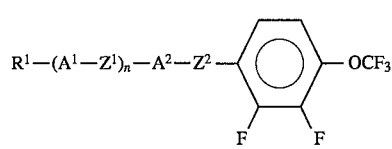

11'

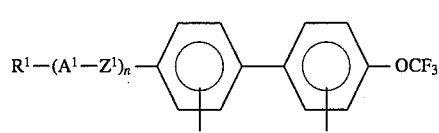

12'

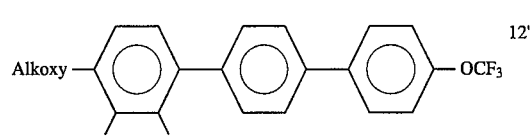

13'

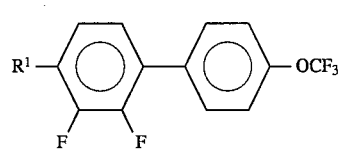

If R¹ is an alkyl radical or an alkoxy radical, it may be straight-chain or branched. It is preferably straight-chain, has 2, 3, 4, 5, 6, 7, 8 or 9 C atoms and is accordingly preferably ethyl, propyl, butyl, pentyl, hexyl, heptyl, octyl, nonyl, ethoxy, propoxy, butoxy, pentoxy, hexyloxy, heptyloxy, octyloxy or nonyloxy, furthermore also methyl, methoxy, decyl, undecyl, dodecyl, tridecyl, tetradecyl, decyloxy, undecyloxy, tridecyloxy or tetradecyloxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl.

If R¹ is an alkyl radical in which A CH₂ group is replaced by —CH=CH—, it may be straight-chain or branched. It is preferably straight-chain and has 2 to 10 C atoms. It is accordingly preferably vinyl, prop-1- or 2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

Compounds of the formula 1' having a branched wing group R¹ may occasionally be important due to better solubility in the customary liquid-crystalline base materials, but in particular as chiral dopes if they are optically active. Compounds of the formula I having S_A phases are suitable for thermally addressed displays.

Branched groups of this type generally contain not more than one chain branch. Preferred branched radicals R¹ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxycarbonyl, 2methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

Formula I covers the racemates of the compounds and the optical antipodes, and mixtures thereof.

In the formula I, R¹ is furthermore alternatively perfluoroalkyl preferably having 2, 3, 4, 5, 6, 7, 8 or 9 C atoms.

Of these compounds of the formula I and of the subformulae thereof, those are preferred in which at least one of the radicals present therein has one of the preferred meanings indicated.

In the compounds of the formula I, preferred stereoisomers are those which the Cyc and piperidine rings are trans-1,4-disubstituted. Those of the abovementioned formula I and its subformulae which contain one or more Pyd, Pyr and/or Dio groups in each case include the two 2,5-positioned isomers.

The 1,4-cyclohexenylene group, Che, of formula I, preferably has the following structures:

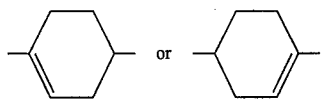

The compounds of the formula I are prepared by methods known per se, as described in the literature (for example in the standard works such as Houben-Weyl,-Methoden der Organischen Chemie, [Methods of Organic Chemistry], Georg-Thieme-Verlag, Stuttgart, Vol. IX, pp. 867 ff.), namely under the reaction conditions which are known and suitable for the reactions mentioned. Variants which are known per se, but not described here in greater detail, can also be used here.

If desired, the starting materials can also be formed in situ in a manner such that they are not isolated from the reaction mixture but instead reacted further to form the compounds of the formula I.

Thus, compounds of the formula I can be prepared by reducing a compound which otherwise corresponds to the formula I, but contains one or more reducible groups and/or C—C bonds in place of H atoms.

Suitable reducible groups are preferably carbonyl groups, in particular keto groups, furthermore, for example, free or esterified hydroxyl groups or aromatically bound halogen atoms. Preferred starting materials for the reduction correspond to the formula I, but contain a cyclohexene ring or cyclohexanone ring in place of a cyclohexane ring and/or a —CH=CH— group in place of a —CH2CH₂— group and/or a —CO— group in place of a —CH₂— group and/or a free or functionally derived (for example in the form of its p-toluenesulfonate) OH group in place of an H atom.

The reduction can be carried out, for example, by catalytic hydrogenation at temperatures between about 0° and about 200° and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid or a hydrocarbon, such as cyclohexane. Suitable catalysts are expediently noble metals, such as Pt or Pd, which can be employed in the form of oxides (for example $PtO_2$ or PdO), on a support (for example Pd on charcoal, calcium carbonate or strontium carbonate) or in finely divided form.

Ketones can also be reduced by the method of Clemmensen (using zinc, amalgamated zinc or tin and hydrochloric acid, expediently in aqueous alcoholic solution or in the heterogeneous phase with water/toluene at temperatures between about 80° and 120° ) or by the method of Wolff-Kishner (using hydrazine, expediently in the presence of alkali, such as KOH or NaOH, in a high-boiling solvent, such as diethylene glycol or triethylene glycol, at temperatures between about 100° and 200° ) to form the corresponding compounds of the formula I, which contain alkyl groups and/or —$CH_2CH_2$— bridges, In addition, reductions using complex hydrides are possible, for example, arylsulfonyloxy groups can be reductively removed using $LiAlH_4$, and in particular p-toluenesulfonyloxymethyl groups can be reduced to methyl groups, expediently in an inert solvent, such as diethyl ether or THF, at temperatures between about 0° and 100°. Double bonds can be hydrogenated using $NaBH_4$ or tributyltin hydride in methanol.

Esters of the formula I can also be obtained by esterification of corresponding carboxylic acids (or reactive derivatives thereof) using alcohols or phenols (or reactive derivatives thereof).

The appropriate carboxylic acids and alcohols or phenols are known and can be prepared analogously to known processes.

Suitable reactive derivatives of the carboxylic acids mentioned are, in particular, the acyl halides, above all the chlorides and bromides, furthermore the anhydrides, for example also mixed anhydrides, azides or esters, in particular alkyl esters having 1–4 C atoms in the alkyl group.

Suitable reactive derivatives of the alcohols or phenols mentioned are, in particular, the corresponding metal alkoxides or phenoxides, preferably of an alkali metal, such as sodium or potassium.

The esterification is advantageously carried out in the presence of an inert solvent. In particular, ethers, such as diethyl ether, di-n-butyl ether, THF, dioxane or anisole, ketones, such as acetone, butanone or cyclohexanone, amides such as DMF or hexamethylphosphoric triamide, hydrocarbons, such as benzene, toluene or xylene, halogenated hydrocarbons, such as carbon tetrachloride or tetrachloroethylene, and sulfoxides, such as dimethyl sulfoxide or sulfolane, are highly suitable.

In order to prepare nitriles of the formula I (in which A¹, A² and/or A³ is substitued by at least one CN group), appropriate acid amides, for example those in which a $CONH_2$ group is present in place of the CN radical, can be de hydrated. The amides can be obtained, for example, from the corresponding esters or acyl halides by reaction with ammonia, Suitable dehydrating agents are, for example, inorganic acid chlorides, such as $SOCl_2$, $PCl_3$, $PCl_5$, $POCl_3$, $SO_2Cl_2$, $COCl_2$ and further $P_2O_5$, $P_2S_5$ and $AlCl_3$ (for example as a double compound with NaCl), aromatic sulfonic acids and sulfonyl halides. This reaction can be carried out in the presence or absence of an inert solvent at temperatures between about 0° and 150°; suitable solvents are, for example, bases, such as pyridine or triethylamine, aromatic hydrocarbons, such as benzene, toluene or xylene, or amides, such as DMF.

In order to prepare the abovementioned nitriles: of the formula I, it is also possible to react appropriate acid halides, preferably the chlorides, with sulfamide, expediently in an inert solvent, such as tetramethylene sulfone, at temperatures between about 80° and 150°, preferably at 120°. After customary work-up, the nitriles can be isolated directly.

Ethers of the formula I (in which R is an alkoxy group and/or $Z^1$ and/or $Z^2$ is an —$OCH_2$— or —$CH_2O$—group) can be obtained by etherification of the corresponding hydroxyl compounds, preferably the corresponding phenols, the hydroxyl compound expediently first being converted into an appropriate metal derivative, for example into the corresponding alkali metal alkoxide or alkali metal phenoxide by treatment with NaH, $NaNH_2$, NaOH, KOH, $Na_2CO_3$ or $K_2CO_3$. This metal derivative can then be reacted with the appropriate alkyl halide alkylsulfonate or dialkyl sulfate, expediently in an inert solvent, such as acetone, 1,2-dimethoxyethane, DMF or dimethyl sulfoxide, or alternatively an excess of aqueous or aqueous alcoholic NaOH or KOH at temperatures between about 20° and 100°.

In order to prepare nitriles of the formula I (in which $A^1$, $A^2$ and/or $A^3$ is substituted by at least one CN group), it is also possible to react corresponding chlorine or bromine compounds of the formula I (in which A and/or $A^2$ and/or $A^3$ is substituted by at least one Cl or Br atom) with a cyanide, expediently with a metal cyanide, such as NaCN, KCN or $Cu_2(CN)_2$, for example in the presence pyridine in an inert solvent, such as DMF or N-methyl-pyrrolidone, at temperatures between 20° and 200°.

Compounds of the formula I in which $A^1$, $A^2$ and/or $A^3$ is substituted by at least one F or Cl atom and/or a CN group can also be obtained from the corresponding diazonium salts by replacement of the diazonium group by a fluorine or chlorine atom or by a CN group, for example by the method of Schiemann or Sandmeyer.

Dioxane derivatives or dithiane derivatives of the formula I (in which one of the $A^1$ and/or $A^2$ groups is a 1,3-dioxane-2,5-diyl group or a 1,3-dithiane-2,5-diyl group are expendiently prepared by reacting a corresponding aldehyde (or a reactive derivative thereof) with an appropriate 1,3-diol (or a reactive derivative thereof) or an appropriate 1,3-dithiol, preferably in the presence of an inert solvent, such as benzene or toluene, and/or in the presence of a catalyst, for example a strong acid, such as sulfuric acid, benzenesulfonic acid or p-toluenesulfonic acid at temperatures between about 20° and about 150°, preferably between about 80° and 120°. Suitable reactive derivatives of the starting materials are primarily acetals.

Some of the aldehydes and 1,3-diols or 1,3-dithiols mentioned, and the reactive derivatives thereof, are known and some can be prepared without difficulties by standard methods of organic chemistry from compounds known from the literature. For example, the aldehydes can be obtained by oxidation of the corresponding alkyls or by reduction of the corresponding carboxylic acids or derivatives thereof, and the diols can be obtained by reduction of the corresponding diesters and the dithiols by reaction of the corresponding dihalides with NaSH.

When preparing the compounds of the formula I, it particularly advantageous to start from starting compounds which already contain the —$OCF_3$ group, for example p-trifluoromethoxybenzaldehyde or 1-bromo-4-trifluoromethoxybenzene. A person skilled in the art can obtain further possible preparations from the literature mentioned or from the Examples.

The liquid-crystalline phases according to an aspect of the invention comprise 2 to 25, preferably 3 to 15, components, including at least one compound of the formula I. The other components are selected from nematic or nematogenic substances, in particular the known substances from the classes comprising the azoxybenzenes, benzylideneanilines, biphenyls, terphenyls, phenyl or cyclohexylbenzoates, phenyl or cyclohexyl cyclohexanoates, phenyl cyclohexanes, cyclohexylbiphenyls, cyclohexylcyclohexanes, cyclohexylnapthalenes, 1,4-biscyclohexylbenzenes, 4,4'-biscyclohexyl-biphenyls, phenyl- or cyclohexylpyrimidines, phenyl- or cyclohexyldioxanes, phenyl- or cyclohexyldithianes, 1,2-bisphenylethanes, 1,2-biscyclohexylethanes, 1-phenyl-2-cyclohexylethanes, optionally halogenated stilbenes, benzyl phenyl ethers, tolanes and substituted cinnamic acids.

The most important compounds which are suitable as components of liquid-crystalline phases of this type may be characterized by the formula II $$R^1—L—G—E—R^2 \qquad \text{II}$$

in which L and E are each a carbocyclic or heterocyclic ring system from the group formed from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthaline, di- and tetra-hydronaphthaline, quinazoline and tetrahydroquinazoline, G is
—CH=CH—
—CH=CY—
—C≡C—
—CO—O—
—CO—S—
—CH=N—
—N(O)=N—
—CH=N(O)—
—$CH_2$—$CH_2$—
—$CH_2$—O—
—$CH_2$—S—
—COO—Phe—COO—
or a C—C single bond, Y is halogen, preferably chlorine or —CN, and $R^1$ and $R^2$ are alkyl, alkoxy, alkanoyloxy or alkoxycarbonyloxy having up to 18, preferably up to 8, carbon atoms, or one of these radicals is altenatively CN, $NO_2$, $CF_3$, F, Cl or Br.

In most of these compounds of formula II, $R^1$ and $R^2$ are different from one another, one of these radicals usually being an alkyl or alkoxy group. However, other variants of the proposed substituents are common. Many such substances or mixtures thereof are commercially available. All these substances can be prepared by methods known from the literature.

The liquid-crystalline phases according to an aspect of the invention contain about 0.1 to 99, preferably 10 to 95%, of one or more compounds of the formula I. Further preferred liquid-crystalline phases are those which contain 0.1–50, in particular 0.5–30, % of one or more compounds of the formula I. It is also possible to use isotropic compounds of the formula I in the phases according to an aspect of the invention.

The liquid-crystalline phases according to the invention are produced in a manner which is known per se. In general, the components are dissolved in one another, expediently at elevated temperature.

By means of suitable additives, the liquid-crystalline phases according to the invention can be modified so that they can be used in all types of liquid-crystal display elements which have been disclosed hitherto.

Such additives are known to those skilled in the art and described in detail in the literature. For example, conductive salts, preferably ethyldimethyldodecylammonium 4-hexyloxybenzoate, tetrabutylammonium tetraphenylboranate or complex salts of crown ethers (cf., for example, I. Haller et al., Mol. Cryst. Liq. Cryst., volume 24, pages 249–258 (1973)) can be added in order to improve the conductivity, dichroic dyes in order to produce coloured guest/host systems or substances in order to change the dielectric anisotropy, the viscosity and/or the orientation of the nematic phases. Such substances are described, for example, in DE-OS 2,209,127, 2,240,864, 2,321,632, 2,338,281, 2,450,088, 2,637,430, 2,853,728 and 2,902,177.

The invention further relates to difluoromethyl compounds of the formula I'

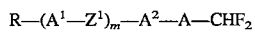

in which

R is H, halogen, —CN, —NCS, an unsubstituted, CN— or $CF_3$-monosubstituted or at least halogen-monosubstituted alkyl or alkenyl radical having 1 to 15 carbon atoms, in which one or more $CH_2$ groups in these radicals, independently of one another, can each also be replaced by —O—, —S—,

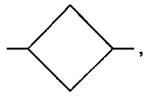

—CO—, —CO—O—, —O—CO— or —O—CO—O— in such a manner that oxygen atoms are not directly linked to one another, $A^1$ and $A^2$, independently of one another, are each a (a) trans-1,4-cyclohexylene radical in which one or more non-adjacent $CH_2$ groups can also be replaced by —O— and/or —S—, (b) 1,4-phenylene radical in which one or two CH groups can also be replaced by N, (c) radical from the group consisting of 1,4-cyclohexenylene, 1,4-bicyclo[2.2.2]-octylene, piperidine-1,4-diyl, naphthalene-2,6-diyl, decahydronaphthalene-2,6-diyl and 1,2,3,4-tetrahydronaphthalene-2,6-diyl, in which the radicals (a) and (b) can be substituted by CN or fluorine, $Z^1$ independently of one another are each —CO—O—, O—CO—, —$CH_2$O—, —O$CH_2$—, —$CH_2CH_2$—, —CH=CH—, —C≡C&13 or a single bond, m is 1, 2 or 3 and Q is alkylene having 2 to 6 carbon atom/s in which a $CH_2$ group can also be replaced by —O—, —S—, —CO—O— or —O—CO—, —O—, —S—, —$CH_2$—, —CO—O—, —O—CO— or a single bond, with the proviso that Q is alkylene having 2 to 6 carbon atoms in which one $CH_2$ group can also be replaced by —O—, —S—, —CO—O— or —O—CO—, —S—, —$CH_2$—, —CO—O—, —O—CO— or a single bond, provided R—($A^1$—$Z^1$)$_m$—$A^2$— is

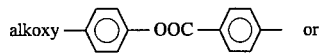

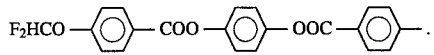

The invention furthermore relates to the use of the compounds of formula I' as components of liquid-crystalline media and liquid crystal and electrooptical display elements containing the liquid-crystalline media.

The compounds of the formula I' can be used as components of liquid-crystalline media, in particular for displays based on the principle of the twisted cell, the guest-host effect, the effect of the deformation of aligned phases or the effect of dynamic scattering.

It has now been found that compounds of the formula I' are highly suitable as components of liquid-crystalline media. In particular, they have comparably low viscosities. With their aid, it is possible to obtain stable liquid-crystalline media having a broad mesophase range and advantageous values for optical and dielectric anisotropy.

Compounds which have liquid-crystalline properties and a terminally bound $OCHF_2$ group are already known. On the one hand, crystal structure investigations have been carried out with Schiff bases [S. V. Sereda et al. in Kristallografiya, 32 (5), 1165 (1987) and ibid. 33 (1) 118 (1988)]. On the other hand, V. V. Titov et al. have described in Mol. Cryst. Liq. Cryst. 47 (1–2), 1 (1978) benzoic esters which carry an $OCHF_2$ group in the para position. However, the known compounds are unstable or unusable in commercial displays.

By providing the compounds of the formula I', very generally the range of liquid-crystalline substances which are suitable under various aspects relating to their application for the preparation of liquid-crystalline mixtures is furthermore considerably widened.

The compounds of the formula I' have a wide application range. Depending on the selection of the substituents, these compounds can serve as basis materials of which liquid-crystalline media are predominantly composed; however, it is also possible to add liquid-crystalline basis materials from other classes of compounds to the compounds of the formula I', in order to effect, for example, dielectric and/or optical anisotropy of such a dielectric and/or to optimize its threshold voltage and/or its viscosity.

The compounds of the formula I' are colorless in their pure state and form liquid-crystalline mesophases in a temperature range favorable for electrooptical use. They are chemically and thermally stable and resistant to light.

The invention accordingly relates to the compounds of the formula I' and the use of these compounds as components of liquid-crystalline media. The invention further relates to liquid-crystalline media containing at least one compound of the formula I' and to liquid crystal display elements, in particular electrooptical display elements containing this type of media.

For the sake of simplicity, in formula I' and its subformulae, X is Q—$CHF_2$, Cyc a 1,4-cyclohexylene radical, Che a 1,4-cyclohexenylene radical, Dio a 1,3-dioxane-2,5-diyl radical, Dit a 1,3-dithiane-2,5-diyl radical, Phe a 1,4-phenylene radical, Pyd a pyridine-2,5-diyl radical, Pyr a pyrimidine-2,5-diyl radical, Pip a piperidine-1,4-diyl radical, Nap a naphthalene-2,6-diyl radical, Dec and Tet a decahydronaphthalene radical and a 1,2,3,4-tetrahydronaphthalene radical and Bi a bicyclo[2.2.2]octylene radical in which Cyc and/or Phe can be unsubstituted or monosubstituted or disubstituted by F or CN.

The compounds of the formula I' accordingly comprise compounds having two rings of the partial formulae Ia' and Ib':

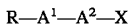   Ia'

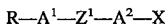   Ib'

Compounds having three rings of the partial formulae Ic' to If':

   Ic'

R—A¹—Z¹—A¹—Z¹—A²—X    Id'

R—A¹—Z¹—A¹—A²—X    Ie'

R—A¹—A¹—Z¹—A²—X    If' and compounds having four rings of the partial formulae Ig' to In':

R—A¹—A¹—A¹—A²—X    Ig'

R—A¹—Z¹—A¹—A¹—A²—X    Ih'

R—A¹—A¹—Z¹—A¹—A²—X    Ii'

R—A¹—A¹—A¹—Z¹—A²—X    Ij'

R—A¹—Z¹—A¹—Z¹—A¹—A²—X    Ik'

R—A¹—Z¹—A¹—A¹—A¹—Z¹—A²—X    Il'

R—A¹—A¹—Z¹—A¹—Z¹—A²—X    Im'

R—A¹—Z¹—A¹—Z¹—A¹—Z¹—A²—X    In'

Of these, in particular those of the partial formulae Ia', Ib', Ic', Id', Ie', If', Ii' and Il' are preferred.

The preferred compounds of the partial formula Ia' comprise those of the partial formulae Iaa' to Iah':

R—Phe—Phe—X    Iaa'

R—Phe—Cyc—X    Iab'

R—Dio—Phe—X    Iac'

R—Pyr—Phe—X    Iad'

R—Pyd—Phe—X    Iae'

R—Cyc—Phe—X    Iaf'

R—Cyc—Cyc—X    Iag'

R—Che—Phe—X    Iah'

Of these, those of the formulae Iaa', Iab', Iac', Iad', Iaf' and Iag' are particularly preferred.

The preferred compounds of the partial formula Ib' comprise those of the partial formulae Iba' to Ibm':

R—Phe—CH₂CH₂—Phe—X    Iba'

R—Phe—OCH₂—Phe—X    Ibb'

R—Cyc—CH₂CH₂—Phe—X    Ibc'

R—Cyc—CH₂—CH₂—Cyc—X    Ibd'

R—Cyc—COO—Phe—X    Ibe'

R—Cyc—COO—Cyc—X    Ibf'

R—A¹—CH₂CH₂—Phe—X    Ibg'

R—A¹—CH₂CH₂—Cyc—X    Ibh'

R—A¹—CH₂O—Phe—X    Ibi'

R—A¹—OCH₂—Phe—X    Ibj'

R—A¹—COO—Phe—X    Ibk'

R—A¹—OOC—Phe—X    Ibl'

R—Che—CH₂CH₂—Phe—X    Ibm'

The preferred compounds of the partial formula Ic' comprise those of the partial formulae Ica' to Icq':

R—Phe—Phe—Phe—X    Ica'

R—Phe—Phe—Cyc—X    Icb'

R—Phe—Dio—Phe—X    Icc'

R—Cyc—Cyc—Phe—X    Icd'

R—Phe—Cyc—Phe—X    Ice'

R—Cyc—Cyc—Cyc—X    Icf'

R—Pyd—Phe—Phe—X    Icg'

R—Pyr—Phe—Phe—X    Ich'

R—Phe—Pyr—Phe—X    Ici'

R—Cyc—Pyr—Phe—X    Icj'

R—Cyc—Phe—Phe—X    Ick'

R—Cyc—Phe—Cyc—X    Icl'

R—Dio—Phe—Phe—X    Icm'

R—Che—Phe—Phe—X    Icn'

R—Phe—Che—Phe—X    Ico'

R—Che—Cyc—Phe—X    Icp'

R—Cyc—Che—Phe—X    Icq'

Of these, those of the formulae Ica', Icc', Icd', Ice', Ici' and Icj' are particularly preferred.

The preferred compounds of the partial formula Id' comprise those of the partial formulae Ida' to Idn':

R—Phe—Z¹—Phe—Z¹—Phe—X    Ida'

R—Phe—Z¹—Phe—Z¹—Cyc—X    Idb'

R—Phe—Z¹—Dio—Z¹—Phe—X    Idc'

R—Cyc—Z¹—Cyc—Z¹—Phe—X    Idd'

R—Cyc—Z¹—Cyc—Z¹—Cyc—X    Ide'

R—Pyd—Z¹—Phe—Z¹—Phe—X    Idf'

R—Phe—Z¹—Pyd—Z¹—Phe—X    Idg'

R—Pyr—Z¹—Phe—Z¹—Phe—X    Idh'

R—Phe—Z¹—Pyr—Z¹—Phe—X    Idi'

R—Phe—Z¹—Cyc—Z¹—Phe—X    Idj'

R—Cyc—Z¹—Phe—Z¹—Cyc—X    Idk'

R—Cyc—Z¹—Phe—Z¹—Phe—X    Idl'

R—Dio—Z¹—Phe—Z¹—Phe—X    Idm'

R—Che—Z¹—Phe—Z¹—Phe—X    Idn'

The preferred compounds of the partial formula Ie' comprise those of the partial formulae Iea' to Iem':

R—Pyr—Z¹—Phe—Phe—X    Iea'

R—Dio—Z¹—Phe—Phe—X    Ieb'

R—Phe—Z¹—Phe—Phe—X    Iec'

R—Cyc—Z¹—Phe—Phe—X    Ied'

R—Cyc—Z¹—Phe—Cyc—X    Iee'

| | |
|---|---|
| R—Phe—Z¹—Cyc—Phe—X | Ief' |
| R—Cyc—Z¹—Cyc—Phe—X | Ieg' |
| R—Cyc—Z¹—Cyc—Cyc—X | Ieh' |
| R—Phe—Z¹—Dio—Phe—X | Iei' |
| R—Pyd—Z¹—Phe—Phe—X | Iej' |
| R—Phe—Z¹—Pyr—Phe—X | Iek' |
| R—Cyc—Z¹—Pyr—Phe—X | Iel' |
| R—Phe—Z¹—Che—Phe—X | Iem' |

The preferred compounds of the partial formula If' comprise those of the partial formulae Ifa' to Ifr':

| | |
|---|---|
| R—Pyr—Phe—Z¹—Phe—X | Ifa' |
| R—Pyr—Phe—OCH₂—Phe—X | Ifb' |
| R—Phe—Phe—Z¹—Phe—X | Ifc' |
| R—Pyr—Phe—OOC—Phe—X | Ifd' |
| R—Pyr—Phe—Z¹—Cyc—X | Ife' |
| R—Cyc—Cyc—Z¹—Phe—X | Iff' |
| R—Cyc—Cyc—Z¹—Cyc—X | Ifg' |
| R—Cyc—Cyc—CH₂CH₂—Phe—X | Ifh' |
| R—Pyd—Phe—Z¹—Phe—X | Ifi' |
| R—Dio—Phe—Z¹—Phe—X | Ifj' |
| R—Phe—Cyc—Z¹—Phe—X | Ifk' |
| R—Phe—Cyc—Z¹—Cyc—X | Ifl' |
| R—Phe—Pyd—Z¹—Phe—X | Ifm' |
| R—Che—Phe—Z¹—Phe—X | Ifn' |
| R—Phe—Che—Z¹—Phe—X | Ifo' |
| R—Cyc—Phe—Z¹—Phe—X | Ifp' |
| R—Cyc—Phe—OOC—Phe—X | Ifq' |
| R—Cyc—Phe—Z¹—Cyc—X | Ifr' |

The preferred compounds of the partial formulae Ig' to In' comprise those of the partial formulae Io' to Iy':

| | |
|---|---|
| R—Cyc—Phe—Cyc—Phe—X | Io' |
| R—Cyc—Cyc—Phe—Phe—X | Ip' |
| R—Cyc—Phe—Phe—Cyc—X | Iq' |
| R—A¹—CH₂O—A¹—A¹—Phe—X | Ir' |
| R—Cyc—Cyc—Z¹—A¹—Phe—X | Is' |
| R—Cyc—Cyc—Z¹—Y¹—Cyc—X | It' |
| R—A¹—A¹—A¹—CH₂CH₂—Phe—X | Iu' |
| R—Phe—Z¹—Phe—Z¹—Dio—Phe—X | Iv' |
| R—Phe—Z¹—Phe—Phe—Z¹—Phe—X | Iw' |
| R—A¹—COO—A¹—COO—A¹—Phe—X | Ix' |
| R—A¹—A¹—COO—A¹—Z¹—Phe—X | Iy' |

In the compounds of the formulae I', Ia'–Iy', Iaa'–Iah', Iba'–Ibm', Ica'–Icq', Ida'–Idn', Iea'–Iem', and Ifn'–Ifr', X is preferably Q—CHF₂ in which Q is alkylene having 2 to 4 carbon atoms and in which a CH₂ group can also be replaced by —O—, —CO—O— or —O—CO—. Furthermore, Q is preferably a single bond, —O—, —S—, —CH₂— and— CO—O—; —O— and —S— are particularly preferred.

If Q is a single bond, those compounds of the formula I' are preferred in which X is bound to a cycloaliphatic ring. If Q is —O— or —S—, those compounds of the formula I' are preferred in which X is bound to an aromatic ring.

R in formula I' and its subformulae is preferably alkyl, furthermore alkoxy. Furthermore, R is preferably a perfluoroalkyl radical in which fluorine can also be partially replaced by hydrogen. In particular those radicals R of the general formula —CH₂—$C_nF_{2n+1}$ and $C_pF_{2p+1}$ where n is equal to 1 to 14 and p is equal to 1 to 15 are preferred. $A^1$ and/or $A^2$ are preferably Phe, Cyc, Che, Pyr or Dio. Particularly preferably, $A^1$ and $A^2$ are Phe or Cyc. Furthermore, those compounds of the formula I' are preferred in which, in addition to Phe and/or Cyc, a further ring selected from the group consisting of Che, Pip, Pyr, Pyd, Dio, Dit, Bi, Nap, Dec or Tet is present.

Compounds of the formula I' and of all partial formulae in which $A^1$ and/or $A^2$ are 1,4-phenylene which is monosubstituted or substituted by F or monosubstituted by CN are also preferred. These are in particular 2-fluoro- 1,4-phenylene, 3-fluoro-1,4-phenylene and 2,3-difluoro-1,4 -phenylene and 2-cyano-1,4-phenylene and 3-cyano-1,4 -phenylene. Of the F-substituted 1,4-phenylene radicals, in particular

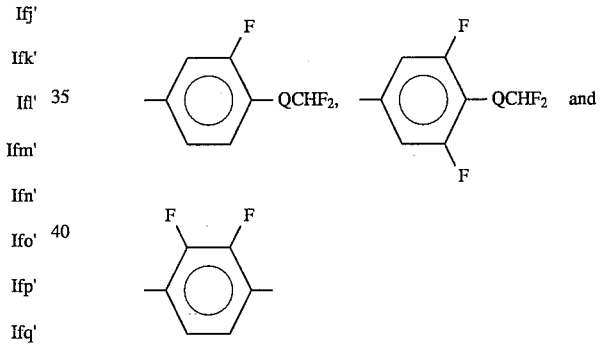

are preferred.

If a radical (a) is substituted by F or CN,

is preferred.

$Z^1$ of formula I' and its subformulae is preferably a single bond, —CO—O—, —O—CO— and —CH₂CH₂—, the second preference being —CH₂O— and—OCH₂—. Compounds which contain no more than one and at most two linking groups $Z^1$ ($Z^1$ not being a single bond) are particularly preferred.

m is preferably 1 or 2.

If R is halogen, R is preferably F, Cl, Br, furthermore also I.

If R is an alkyl radical and/or an alkoxy radical, it can be straight-chain or branched. Preferably it is straight-chain, has 2, 3, 4, 5, 6 or 7 carbon atoms and is accordingly preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2 -, 3-, 4- or 5-oxahexyl, 2-, 3-, 4-, 5- or 6-oxaheptyl, 2-, 3-, 4-, 5-, 6 - or 7-oxaoctyl, 2 -, 3-, 4 -, 5-, 6 -, 7 - or 8-oxanonyl, 2-, 3-, 4-, 5-, 6-, 7-, 8- or 9-oxadecyl.

If R is an alkyl radical in which one $CH_2$ group has been replaced by -CH=CH-, it can be straight-chain or branched. Preferably, it is straight-chain and has 2 to 10 carbon atoms. Accordingly, it is in particular vinyl, prop-1- or prop-2-enyl, but-1-, -2- or but-3-enyl, pent 1-, -2-, -3- or pent-4-enyl, hex-1-, -2-, -3-, -4- or hex-5-enyl, hept-1-, -2-, -3-, -4-, -5- or hept-6-enyl, oct-1-, -2-, -3-, -4-, -5-, -6- or oct-7-enyl, non-1-, -2-, -3-, -4-, -5-, -6-, -7- or non-8-enyl, dec-1-, -2-, -3-, -4 -, -5-, -6-, -7-, -8- or dec-9-enyl.

If R is an alkyl radical in which one $CH_2$ group has been replaced by —O— and one by —CO—, these groups are preferably adjacent. Thus, they contain an acyloxy group —CO—O— or an oxycarbonyl group —O—CO—. Preferably, these are straight-chain and have 2 to 6 carbon atoms. Accordingly, they are in particular acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)-ethyl, 3-(methoxycarbonyl)propyl, 3-(ethoxycabonyl)propyl, 4-(methoxycarbonyl)butyl.

If R is an alkyl radical in which one $CH_2$ group has been replaced by unsubstituted or substituted —CH=CH— and one adjacent $CH_2$ group by CO or CO—O or O—CO—, it can be straight-chain or branched. Preferably, it is straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9 -acryloyloxynonyl, 10-acryloyloxydecyl, methacryloyloxymethyl, 2 -methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl, 9-methacryloyloxynonyl.

Compounds of the formula I' which have wing groups R suitable for polymerization reactions are suitable for the preparation of liquid-crystalline polymers.

Compounds of the formula I' containing branched wing groups R can in some cases be important because of better solubility in the conventional liquid-crystalline basis materials, but in particular as chiral doping substances, if they are optically active. Smectic compounds of this type are suitable as components for ferroelectric materials.

Compounds of the formula I' which have $S_A$ phases are suitable, for example, for thermally addressed displays.

Branched groups of this type contain, as a rule, not more than one chain branching. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy.

If R is an alkyl radical in which two or more $CH_2$ groups have been replaced by —O— and/or —CO—O—, it can be straight-chain or branched. Preferably, it is branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl, 5,5-bis(ethoxycarbonyl)hexyl.

Compounds of the formula I' which have wing groups R suitable for polycondensations are suitable for the preparation of liquid-crystalline polycondensation products.

Formula I' comprises not only the racemates of these compounds but also the optical antipodes and their mixtures.

Of these compounds of the formula I' and the Subformulae thereof, those are preferred in which at least one the radicals contained therein has one of the preferred meanings mentioned.

In the compounds of the formula I', those stereoisomers are preferred in which the rings Cyc and piperidine are trans-1,4-disubstituted. Those of the above-mentioned formula I' and its subformulae which contain one or several groups Pyd, Pyr and/or Dio each comprise the two isomers in the 2,5-position.

The 1,4-cyclohexenylene group, Che, of formula I' preferably has the following structures:

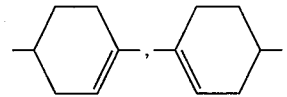

The compounds of the formula I' are prepared by methods known per se, such as are described in the literature (for example in the standard works such as Houben-Weyl, Methoden der Organischen Chemie (Methods of Organic Chemistry), Georg-Thieme Verlag, Stuttgart Vol. IX, p. 867 ff.) under reaction conditions which are known and suitable for the reactions mentioned. It is also possible to make use of variations which are known per se and not mentioned in more detail at this point.

The aryldifluoromethyl ethers according to the invention can be prepared, for example, by reacting hydroxyaryl compounds with chlorodifluoromethane under reaction conditions which are suitable for the Reimer-Tiemann reaction between phenols and chloroform [T. G. Miller, J. W. Thanassi, J. Org. Chem. 25., 2009 (1960)].

The etherification can be carried out in known manner in aprotic, strongly polar solvents (JP-OS 59/157,041) and in aqueous or even in almost anhydrous media, for example, by carrying out the formation of alcohol in aqueous-organic phase (#or example tetrahydrofuran/water), but removing most of the water azeotropically before the actual etherification.

Difluoroalkylaryl ethers according to the invention can, for example, also be prepared, for example, by reacting the corresponding nitro- or fluorobenzenes which additionally carry at least one electron-withdrawing substituent directly with alkali metal difluoroalkoxy compounds, in which F or $NO_2$ is substituted by the difluoroalkoxy radical [J.P. Idoux et al., J. Org. Chem. 50, 1976 (1985)].

Difluoromethyl compounds of the formula I' can be prepared, for example, by reacting aldehydes with dialkylaminosulfur trifluoride, for example DAST (diethylamino sulfurtrifluoride) [W. J. Middleton, J. Org. Chem. 40, 574 (1975)].

Difluoromethylthio compounds can be prepared by the same method as difluoromethoxy compounds (for example according to L. N. Sedova et al., Zh. Org. Khim. 6, (1970) 568).

If desired, the starting materials can also be formed in situ in such a manner that they are not isolated from the reaction mixture but immediately reacted further to give the compounds of the formula I'.

Thus, the compounds of the formula I' can be prepared by reducing a compound which otherwise corresponds to the formula I', but contains one or more reducible groups and/or C—C bonds instead of the hydrogen atoms.

Suitable reducible groups are preferably carbonyl groups, in particular keto groups, furthermore, for example, free or esterified hydroxyl groups or aromatically bound halogen atoms. Preferred starting materials for the reduction have the formula I', but can contain a cyclohexene ring or cyclohexanone ring instead of a cyclohexane ring and/or a —CH=CH— group instead of a —$CH_2CH_2$— group and/or a —CO— group instead of a —$CH_2$— group and/or a free or functionally (for example in the form of its p-toluenesulfonate) modified OH group instead of a hydrogen atom.

The reduction can be carried out, for example, by catalytic hydrogenation at temperatures between about 0° and about 200° and pressures between about 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid or: a hydrocarbon such as cyclohexane. Suitable catalysts are advantageously noble metals such as Pt or Pd, which can be used in the form of oxides (for example $PtO_2$, PdO) on a support (for example Pd on carbon, calcium carbonate or strontium carbonate) or in finely divided form.

Ketones can also be reduced by the methods of Clemmensen (using zinc, amalgamated zinc or tin and hydrochloric acid, advantageously in aqueous-alcoholic solution or in heterogeneous phase using water/toluene at temperatures between about 80° and 120° ) or Wolff-Kishner (using hydrazine, advantageously in the presence of alkali such as KOH or NaOH in a high-boiling solvent such as diethylene glycol or triethylene glycol at temperatures between about 100° and 200° ) to give the corresponding compounds of the formula I' containing alkyl groups and/or —$CH_2CH_2$— bridges.

Another possibility are reductions using complex hydrides. For example, arylsulfonyloxy groups can be removed reductively using $LiAlH_4$, in particular p-toluenesulfonyloxymethyl groups can be reduced to methyl groups, advantageously in an inert solvent such as diethyl ether or THF at temperatures between about 0° and 100° . Double bonds can be hydrogenated using $NaBH_4$ or tributyltin hydride in methanol.

Compounds of the formula I' which otherwise correspond to the formula I', but have 1,4-cyclohexenylene radicals instead of 1,4-phenylene radicals, can be oxidized, for example, with DDQ (dichlorodicyanobenzoquinone) in a suitable solvent.

Esters of the formula I' can also be obtained by esterification of the corresponding carboxylic acids (or their reactive derivatives) with alcohols or phenols (or their reactive derivatives) or by the DCC method (DCC=dicyclohexylcarbodiimide).

The corresponding carboxylic acids and alcohols or phenols are known or can be prepared in analogy to known processes.

Thiophenols can be prepared, for example, by reacting the corresponding benzene derivatives with chlorosulfonic acid and then reducing the product, for example using zinc/dilute hydrochloric acid, or reacting the corresponding phenol derivatives with dimethylcarbamoyl chloride and then rearranging the product, as described in DE 3,434,335.

Suitable reactive derivatives of the carboxylic acids mentioned are in particular acid halides, in particular the chlorides and bromides, furthermore the anhydrides, for example even mixed anhydrides, azides or esters, in particular alkyl esters having 1–4 carbon atoms in the alkyl group.

Suitable reactive derivatives of the alcohols and phenols mentioned are in particular the corresponding metal alcoholates or phenolates, preferably of an alkali metal such as sodium or potassium.

The esterification is advantageously carried out in the presence of an inert solvent. Very suitable for this purpose are in particular ethers such as, for example, diethyl ether, di-n-butyl ether, THF, dioxane or anisole, ketones such as, for example, acetone, butanone or cyclohexanone, amides such as, for example, DMF or hexamethylphosphoric triamide, hydrocarbons such as, for example, benzene, toluene or xylene, halogenated hydrocarbons such as, for example, carbon tetrachloride, dichloromethane or tetrachloroethylene and sulfoxides such as, for example, dimethyl sulfoxide or sulfolane.

In a further process for the preparation of the compounds of the formula I', an aryl halide is reacted with an olefin in the presence of a tertiary amine and a palladium catalyst (cf. R. F. Heck, Acc. Chem. Res. 12 (1979) 146). Examples of suitable aryl halides are chlorides, bromides and iodides, in particular bromides and iodides. The tertiary amines which are necessary for the successful completion of the coupling reaction, such as, for example, triethylamine, are also suitable as solvents. Examples of suitable palladium catalysts are palladium salts, in particular Pd(II) acetate, in combination with organic, phosphorus(III) compounds such as, for example, triarylphosphanes. This reaction can be carried out in the presence or absence of an inert solvent at temperatures between about 0° and 150°, preferably between 20° and 100°; examples of suitable solvents are nitriles such as acetonitrile or hydrocarbons such as benzene or toluene. Many of the aryl halides and olefins used as starting materials are commercially available or can be prepared by processes known from the literature, for example by halogenation of the corresponding parent compounds or by elimination reactions of the corresponding alcohols or halides.

For example, stilbene derivatives can be prepared in this manner. The stilbenes can also be prepared by reaction of a 4-substituted benzaldehyde with the corresponding phosphorus ylide according to Wittig. However, it is also possible to prepare tolans of the formula I' by using monosubstituted acetylene instead of the-olefin (Synthesis 627 (1980) or Tetrahedron Lett. 27, 1171 (1986)).

Furthermore, aromatics can be coupled by reacting aryl halides with aryltin compounds. Preferably, these reactions are carried out with the addition of a catalyst such as, for example, a palladium(0) complex in inert solvents such as hydrocarbons at high temperatures, for example in boiling xylene, under a protective gas.

Couplings of alkyinyl compounds with aryl halides can be carried out analogously to the process described by A. O. King, E. Negishi, F. J. Villani and A. Silveira in J. Org. Chem. 43, 358 (1978).

Tolans of the formula I' can also be prepared via the Fritsch-Buttenberg-Wiechell rearrangement (Ann. 279, 319, 332, 1984), in which 1,1-diaryl-2-halogenoethylenes are rearranged to diarylacetylenes in the presence of strong bases.

Tolanes of the formula I' can also be prepared by bromination of the corresponding stilbenes, followed by dehydrohalogenation. It is possible to use the variations of this reaction which are known per se but not mentioned here in more detail.

Nitriles of the formula I' can be prepared by dehydrating the corresponding amides, for example those which have a $CONH_2$ group instead of the radical CN. The amides are obtainable, for example, from the corresponding esters or acid halides by reaction with ammonia. Examples of suitable dehydrating agents are inorganic acid chlorides such as $SOCl_2$, $PCl_3$, $PCl_5$, $POCl_3$, $SO_2Cl_2$, $COCl_2$, furthermore $P_2O_5$, $P_2S_5$, $AlCl_3$ (for example as double salt with NaCl), aromatic sulfonic acids and sulfonyl halides. This reaction can be carried out in the presence or absence of an inert solvent at temperatures between about 0° and 150°; examples of suitable solvents are bases such as pyridine or triethylamine, aromatic hydrocarbons such as benzene, toluene or xylene or amides such as DMF.

The abovementioned nitriles of the formula I' can also be prepared by reacting the corresponding acid halides, preferably the chlorides, with sulfamide, advantageously in an inert solvent such as, for example, tetramethylene sulfone at temperatures between about 80° and 150°, preferably at 120°. After conventional work-up, the nitriles can be isolated directly.

Ethers of the formula I' are available by etherification of the corresponding hydroxy compounds, preferably of the corresponding phenols, in which the hydroxy compound is advantageously first converted into a corresponding metal derivative, for example converted into a corresponding alkali metal alcoholate or alkali metal phenolate by treatment with NaH, $NaNH_2$, NaOH, KOH, $Na_2CO_3$ or $K_2CO_3$. This derivative can then be reacted with the corresponding alkyl halide, alkyl sulfonate or dialkyl sulfate, advantageously in an inert solvent such as, for example, acetone, 1,2-dimethoxyethane, DMF or dimethyl sulfoxide or even with an excess of aqueous or aqueous-alcoholic NaOH or KOH at temperatures between about 20° and 100°.

The nitriles of the formula I' can also be prepared by reacting the corresponding chlorine, bromine or iodine compounds of the formula I' with a cyanide, preferably with a metal cyanide such as, for example, NaCN, KCN or $Cu_2(CN)_2$, for example in the presence of pyridine in an inert solvent such as, for example, DMF or N-methylpyrrolidone at temperatures between 20° and 200°.

Compounds of the formula I' in which $A^1$ is substituted by at least one F atom and/or one CN group can also be obtained from the corresponding diazonium salts by exchange of the diazonium group for a fluorine atom or for a CN group, for example by the methods of Schiemann or Sandmeyer.

Dioxane derivatives or dithiane derivatives of the formula I' are advantageously prepared by reaction of the corresponding aldehyde (or one of its reactive derivatives) with a suitable 1,3-diol (or one of its reactive derivatives) or a suitable 1,3-dithiol, preferably in the presence of an inert solvent such as, for example, benzene or toluene and/or a catalyst, for example a strong acid such as sulfuric acid, benzenesulfonic acid or p-toluenesulfonic acid, at temperatures between about 20° and about 150°, preferably between 80° and 120°. Suitable reactive derivatives of the starting materials are primarily acetals.

Some of the aldehydes and 1,3-diols or 1,3-dithiols mentioned and their reactive derivatives are known and others can be prepared without difficulties by standard processes of organic chemistry from compounds known from the literature. For example, the aldehydes are available by oxidation of the corresponding alcohols or by reduction of nitriles or the corresponding carboxylic acids or their derivatives, the diols by reduction of the corresponding diesters and the dithiols by reaction of the corresponding dihalides with NaSH.

The liquid-crystalline media according to an aspect of the invention preferably contain, in addition to one or more compounds of formula I' as further components 2 to 40, in particular 4 to 30 components. Very particularly preferably, these media contain, in addition to one or more compounds according to formula I', 7 to 25 components. These further components are preferably selected from nematic or nematogenic (monotropic or isotropic) substances, in particular substances from the classes of azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl benzoates, cyclohexylphenyl cyclohexanecarboxylates, cyclohexylphenyl cyclohexylcyclohexanecarboxylates, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl-or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, halogenated or unhalogenated stilbenes, benzyl phenyl ethers, tolanes and substituted cinnamic acids. The 1,4-phenylene groups in these compounds can also be fluorinated.

The most important compounds which are suitable as further components of media according to an aspect of the invention can be characterized by formulae 1a, 2a, 3a, 4a and 5a:

    1a

    2a

    3a

    4a

    5a

In the formulae 1a, 2a, 3a, 4a and 5a, L and E, which can be identical or different, are each, independently of one another, a divalent radical from the group consisting of —Phe—, —Cyc—, —Phe—Phe—, —Phe—Cyc—, —Cyc—Cyc—, —Pyr—, —Dio—, —G—Phe— and —G—Cyc— and their mirror images, in which Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

Preferably, one of the radicals L and E is Cyc, Phe or Pyr. E is preferably Cyc, Phe or Phe—Cyc. Preferably, the media according to an aspect of the invention contain one or more components selected from the compounds of the formulae 1a, 2a, 3a, 4a and 5a, in which L and E are selected from the group consisting of Cyc, Phe and Pyr and simultaneously one or more components of Cyc, Phe and Pyr and simultaneously one or more components are selected from the compounds of the formulae 1a, 2a, 3a, 4a and 5a, in which one of the radicals L and E is selected from the group consisting of Cyc, Phe and Pyr and the other radical is selected from the group consisting of —Phe—Phe—, —Phe—Cyc—, —Cyc—Cyc—, —G—Phe— and —G—Cyc—, and possibly one or more components are selected from the compounds of the formulae 1a, 2a, 3a, 4a and 5a, in which the radicals l and E are selected from the group consisting of —Phe—Cyc—, —Cyc—Cyc—, —G—Phe— and —G—Cyc—.

R' and R" in the compounds of the partial formulae 1a', 2a', 3a', 4a' and 5a' are each, independently of one another, alkyl, alkenyl, alkoxy, alkenyloxy or alkanoyloxy having up to 8 carbon atoms. In most of these compounds, R' and R" are different from one another and one of these radicals is in most cases alkyl or alkenyl. In the compounds of the partial formulae 1b, 2b, 3b, 4b and 5b, R" is —CN, —CF$_3$, F, Cl or —NCS; in these formulae, R has the meaning mentioned in the compounds of the partial formulae 1a' to 5a' and is preferably alkyl or alkenyl. However, other variations of the substituents intended for the compounds of the formulae 1a, 2a, 3a, 4a and 5a are common. Many of these substances or even mixtures thereof are commercially available. All these substances are available by methods known from the literature or analogously to those methods.

The media according to an aspect of the invention preferably contain, in addition to the components from the group of compounds 1a', 2a', 3a', 4a' and 5a' (group 1), also components from the group of compounds 1b, 2b, 3b, 4b and 5b (group 2), the relative proportions of which are preferably as follows:

Group 1: 20 to 90%, in particular 30 to 90%,
Group 2: 10 to 80%, in particular 10 to 50%,
the sum of the relative proportions of the compounds according to the invention and the compounds from groups 1 and 2 adding up to 100%.

The media according to an aspect of the invention preferably contain 1 to 40%, in particular preferably 5 to 30%, of compounds according to formula I' of the invention. Further preference is given to media containing more than 40%, in particular 45 to 90%, of compounds according to formula I' of the invention. The media preferably contain three, four or five compounds according to formula I' of the invention.

The media according to the invention are prepared in a manner customary per se. As a rule, the components are dissolved in one another, advantageously at elevated temperature. By means of suitable additives, the liquid-crystalline phases according to the invention can be modified in such a manner that they can be used in all previously known types of liquid crystal display elements. This type of additive is known to one skilled in the art and has been described in detail in the literature (H. Kelker/R. Hatz, Handbook of liquid Crystals, Verlag Chemie, Weinheim, 1980). For example, pleochroitic dyes to prepare coloured guest-host systems or substances to change the dielectric anisotropy, the viscosity and/or the orientation of the nematic phases can be added.

The invnetion further relates to new fluorobenzene derivatives of the formula I",

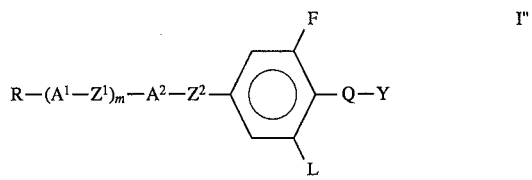

in which

R is H, an alkyl or alkenyl radical of 1 to 15 carbon atoms which is unsubstituted or monosubstituted by CN or CF$_3$ or at least monosubstituted by halogen, it being possible for one or more CH$_2$ groups in these radicals also to be replaced, in each case independently of one another, by —O—, —S—, —CO—, —CO—O—, —O—CO— or —O—CO—O— in such a manner that O atoms are not linked directly to one another, A$^1$ and A$^2$, in each case independently of one another, are
(a) trans-1,4-cyclohexylene radical, in which one or more non-adjacent CH$_2$ groups can also be replaced by —O— and/or —S—,
(b) 1,4-phenylene radical, in which one or two CH groups can also be replaced by N,
(c) radical from the group comprising 1,4-cyclohexenylene, 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, it being possible for the radicals (a) and (b) to be substituted by CN or fluorine, Z$^1$ and Z$^2$, in each case independently of one another, are —CO—O—, —O—CO—, —CH$_2$O—, —OCH$_2$—, —CH$_2$CH$_2$—, —CH=CH—, —C≡C— or a single bond, one of the radicals Z$^1$ and Z$^2$ is also —(CH$_2$)$_4$— or —CH=CH—CH$_2$CH$_2$—, L is H or F,
m is 0, 1 or 2,
Y is F or Cl, and
Q is a single bond, —CF$_2$—, —OCF$_2$— or —OCHF—, with the proviso that L is F, if Q is a single bond.

The invention furthermore relates to the use of compounds of formula I" as components of liquid-crystalline media and to liquid-crystal and electrooptical display elements containing the liquid-crystalline media.

The compounds of the formula I" can be used as components of liquid-crystalline media, in particular for displays based on the principle of the twisted cell, the guest-host effect, the effect of the deformation of aligned phases or the effect of dynamic scattering.

It has now been found that compounds of the formula I" are highly suitable as components of liquid-crystalline media. In particular, they have comparatively low viscosities. By means of them, it is possible to obtain stable liquid-crystalline media having a broad mesophase range and advantageous values for optical and dielectric anisotropy. These media furthermore have a very good low-temperature behavior.

Liquid crystals of the formula

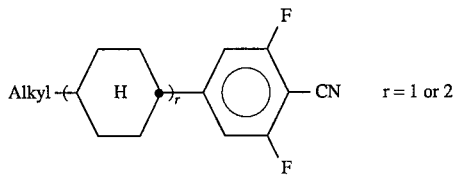

have already been disclosed in DE 3,209,178: Compounds of the formulae

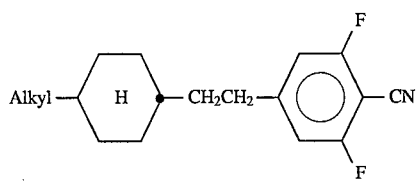

and

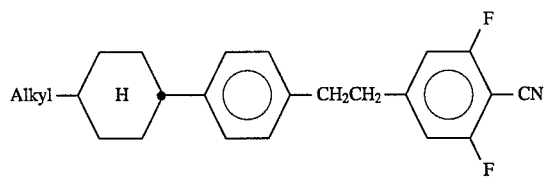

are disclosed in JP 62/103,057. Finally, compounds of-the formula

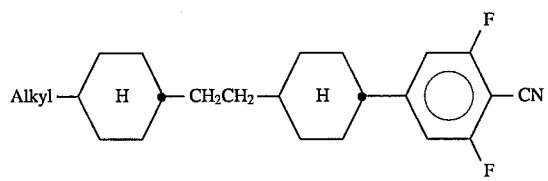

are described in JP 63/216,858. Compounds of the following formulae:

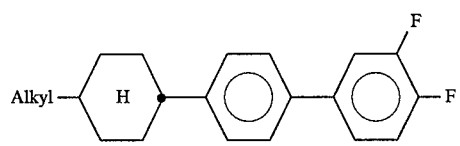

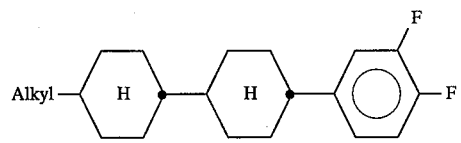

are disclosed in German Offenlegungsschriften 3,042,391 and 3,139,130.

Various compounds having liquid-crystalline properties and a terminally-bound $CF_3$ group are already known (U.S. Pat. No. 4,330,426; U.S. Pat. No. 4,684,476; J. C. Liang and S. Kumar, Mol. Cryst. Liq. Cryst. 1987; Vol. 142, pp. 77–84). However, these compounds often have a strongly smectogenic character and are less suitable for many practical applications.

However, in view of the wide range of applications of these compounds having a high $\Delta\epsilon$, it was desirable to have available further compounds of exactly tailor-made properties for the particular applications. In addition, by providing the compounds of the formula I", the range of liquid-crystalline substances, which in the various aspects of industrial application are suitable for the preparation of liquid-crystalline mixtures, is very generally and significantly broadened.

The compounds of the formula I" have a broad range of applications. Depending on the choice of substituents, these compounds can serve as base material of which liquid-crystalline media are composed for the most part; however, it is also possible to add compounds of the formula I" to liquid-crystalline base materials from other classes of compounds, in order, for example, to influence the dielectric and/or optical anisotropy of such a dielectric and/or to optimize its threshold voltage and/or its viscosity.

In the pure state, the compounds of the formula I" are colorless and form liquid-crystalline mesophases in a temperature range favored for electrooptical use. They have very good chemical, heat and light stability.

Accordingly, the invention relates to compounds of the formula I" and to the use of these compounds as components of liquid-crystalline media containing at least one compound of the formula I" and to liquid-crystal display elements, in particular electrooptical display elements, containing such media.

For the sake of simplicity, below $A^3$ of formula I" and it subformulae is a radical of the formula

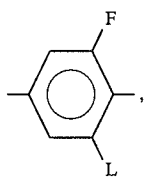

Cyc a 1,4-cyclohexylene radical, Che a 1,4-cyclohexenyl radical, Dio a 1,3-dioxane-2,5-diyl radical, Dit a 1,3-dithiane-2,5-diyl radical, Phe a 1,4-phenylene radical, Pyd a pyridine-2,5-diyl radical, Pyr a pyrimidine-2,5-diyl radical and Bi a bicyclo[2.2.2]-octylene radical, it being possible for Cyc and/or Phe to be unsubstituted or mono- or disubstituted by F or CN. L is preferably F. Y is preferably F.

$A^1$ and $A^2$ of formula I" and its subformulae are preferably selected from the group comprising Cyc, Che, Phe, Pyr, Pyd and Dio, preferably only one of the radicals $A^1$ and $A^2$ present in the molecule being Che, Phe, Pyr, Pyd or Dio.

The compounds of the formula I" accordingly comprise compounds having two rings of the subformulae Ia" and Ib":

| R—$A^2$—$A^3$—Q—Y | Ia" |
|---|---|
| R—$A^2$—$Z^2$—$A^3$—Q—Y | Ib" |

Compounds having three rings of the subformulae Ic" to If":

| R—$A^1$—$A^2$—$A^3$—Q—Y | Ic" |
|---|---|
| R—$A^1$—$Z^1$—$A^2$—$Z^2$—$A^3$—Q—Y | Id" |
| R—$A^1$—$Z^1$—$A^2$—$A^3$—Q—Y | Ie" |
| R—$A^1$—$A^2$—$Z^2$—$A^3$—Q—Y | If" | and compounds having four rings of the subformulae Ig" to Im":

| R—$A^1$—$A^1$—$A^2$—$A^3$—Q—Y | Ig" |
|---|---|

Of these, in particular those of the subformulae Ia", Ib", Ic", Id", Ie", If", Ii" and Il" are preferred.

The preferred compounds of the subformulae Ia" comprise those of the subformulae Iaa" to Iah":

| | |
|---|---|
| R—Phe—A³—Q—Y | Iaa" |
| R—Phe—A³—Q—Y | Iab" |
| R—Dio—A³—Q—Y | Iac" |
| R—Pyr—A³—Q—Y | Iad" |
| R—Pyd—A³—Q—Y | Iae" |
| R—Cyc—A³—Q—Y | Iaf" |
| R—Cyc—A³—Q—Y | Iag" |
| R—Che—A³—Q—Y | Iah" |

Of these, those of the formulae Iaa", Iab", Iac", Iad", Iaf" and Iag" are particularly preferred.

The preferred compounds of the subformula Ib" comprise those of the subformulae Iba" and Ibb":

| | |
|---|---|
| R—Cyc—CH₂CH₂—A³—Q—Y | Iba" |
| R—Cyc—COO—A³—Q—Y | Ibb" |

The preferred compounds of the subformula Ic" comprise those of the subformulae Ica" to Ico":

| | |
|---|---|
| R—Phe—Phe—A³—Q—Y | Ica" |
| R—Phe—Phe—A³—Q—Y | Icb" |
| R—Phe—Dio—A³—Q—Y | Icc" |
| R—Cyc—Cyc—A³—Q—Y | Icd" |
| R—Phe—Cyc—A³—Q—Y | Ice" |
| R—Cyc—Cyc—A³—Q—Y | Icf" |
| R—Pyd—Phe—A³—Q—Y | Icg" |
| R—Pyr—Phe—A³—Q—Y | Ich" |
| R—Phe—Pyr—A³—Q—Y | Ici" |
| R—Cyc—Pyr—A³—Q—Y | Icj" |
| R—Cyc—Phe—A³—Q—Y | Ick" |
| R—Cyc—Phe—A³—Q—Y | Icl" |
| R—Dio—Phe—A³—Q—Y | Icm" |
| R—Che—Phe—A³—Q—Y | Icn" |
| R—Phe—Che—A³—Q—Y | Ico" |

Of these, those of the formulae Ica", Icc", Icd", Ice", Ici" and Icj" are particularly preferred.

The preferred compounds of the subformula Id" comprise those of the subformulae Ida" to Idm":

| | |
|---|---|
| R—Phe—Z¹—Phe—Z¹—A³—Q—Y | Ida" |
| R—Phe—Z¹—Phe—Z¹—A³—Q—Y | Idb" |
| R—Phe—Z¹—Dio—Z¹—A³—Q—Y | Idc" |
| R—Cyc—Z¹—Cyc—Z¹—A³—Q—Y | Idd" |
| R—Cyc—Z¹—Cyc—Z¹—A³—Q—Y | Ide" |
| R—Pyd—Z¹—Phe—Z¹—A³—Q—Y | Idf" |
| R—Phe—Z¹—Pyd—Z¹—A³—Q—Y | Idg" |
| R—Pyr—Z¹—Phe—Z¹—A³—Q—Y | Idh" |
| R—Phe—Z¹—Pyr—Z¹—A³—Q—Y | Idi" |
| R—Phe—Z¹—Cyc—Z¹—A³—Q—Y | Idj" |
| R—Cyc—Z¹—Phe—Z¹—A³—Q—Y | Idk" |
| R—Cyc—Z¹—Phe—Z¹—A³—Q—Y | Idl" |
| R—Dio—Z¹—Phe—Z¹—A³—Q—Y | Idm" |

The preferred compounds of the subformula Ie" comprise those of the subformulae Iea" to Iel":

| | |
|---|---|
| R—Pyr—Z¹—Phe—A³—Q—Y | Iea" |
| R—Dio—Z¹—Phe—A³—Q—Y | Ieb" |
| R—Phe—Z¹—Phe—A³—Q—Y | Iec" |
| R—Cyc—Z¹—Phe—A³—Q—Y | Ied" |
| R—Cyc—Z¹—Phe—A³—Q—Y | Iee" |
| R—Phe—Z¹—Cyc—A³—Q—Y | Ief" |
| R—Cyc—Z¹—Cyc—A³—Q—Y | Ieg" |
| R—Cyc—Z¹—Cyc—A³—Q—Y | Ieh" |
| R—Phe—Z¹—Dio—A³—Q—Y | Iei" |
| R—Pyd—Z¹—Phe—A³—Q—Y | Iej" |
| R—Phe—Z¹—Pyr—A³—Q—Y | Iek" |
| R—Cyc—Z¹—Pyr—A³—Q—Y | Iel" |

The preferred compounds of the subformula If" comprise those of the subformulae Ifa" to Ifr":

| | |
|---|---|
| R—Pyr—Phe—Z¹—A³—Q—Y | Ifa" |
| R—Pyr—Phe—OCH₂—A³—Q—Y | Ifb" |
| R—Phe—Phe—Z¹—A³—Q—Y | Ifc" |
| R—Phe—Phe—OOC—A³—Q—Y | Ifd" |
| R—Phe—Phe—Z¹—A³—Q—Y | Ife" |
| R—Cyc—Cyc—Z¹—A³—Q—Y | Iff" |
| R—Cyc—Cyc—Z¹—A³—Q—Y | Ifg" |
| R—Cyc—Cyc—CH₂CH₂—A³—Q—Y | Ifh" |
| R—Pyd—Phe—Z¹—A³—Q—Y | Ifi" |
| R—Dio—Phe—Z¹—A³—Q—Y | Ifj" |
| R—Phe—Cyc—Z¹—A³—Q—Y | Ifk" |
| R—Phe—Cyc—Z¹—A³—Q—Y | Ifl" |
| R—Phe—Pyd—Z¹—A³—Q—Y | Ifm" |
| R—Che—Phe—Z¹—A³—Q—Y | Ifn" |
| R—Phe—Che—Z¹—A³—Q—Y | Ifo" |
| R—Cyc—Phe—Z¹—A³—Q—Y | Ifp" |
| R—Cyc—Phe—OOC—A³—Q—Y | Ifq" |
| R—Cyc—Phe—Z¹—A³—Q—Y | Ifr" |

In the compounds of formulae I" and its subformulae, Y is preferably F.

R in formula I" and its subformulae is preferably alkyl, furthermore alkoxy. $A^1$ and/or $A^2$ are preferably Phe, Cyc, Che, Pyr or Dio. Preferably, the compounds of formula I" do not contain more than one of the radicals Bi, Pyd, Pyr, Dio or Dit.

Compounds of the formula I" and of all subformulae in which $A^1$ and/or $A^2$ is 1,4-phenylene which is mono- or disubstituted by F or monosubstituted by CN are also preferred. They are in particular 2-fluoro-1,4-phenylene, 3-fluoro-1,4-phenylene and 3,5-difluoro-1,4-phenylene and 2-cyano-1,4-phenylene and 3-cyano-1,4-phenylene. In a particularly preferred embodiment, $A^2$ is 3,5-difluoro-1,4-phenylene and m is 1 or 2.

$Z^1$ and $Z^2$ of formula I" and its subformulae are preferably a single bond, —CO—O—, —O—CO— and —$CH_2CH_2$—, and secondly preferably —$CH_2O$— and —$OCH_2$—.

If in formula I" and its subformulae, one of the radicals $Z^1$ and $Z^2$ is —$(CH_2)_4$— or —CH=CH—$CH_2CH_2$—, the other radical $Z^1$ or $Z^2$ (if present) is preferably a single bond.

Preferred compounds of this type correspond to the subformula I'''

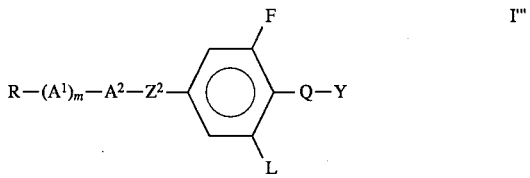

in which $Z^2$ is —$(CH_2)_4$— or —CH=CH—$CH_2CH_2$— and R, $A^1$, $A^2$, m, L, Q and Y have the meaning indicated in formula I". The preferred meanings for R, $A^1$, $A^2$, m, L, Q and Y also correspond to those for the compounds of the formula I".

m in formula I" and its subformulae is preferably 1 or 0, in particular preferably 0.

An alkyl radical and/or alkoxy radical R of formula I" and its subformulae can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7 or 8-oxanonyl, 2-, 3-, 4-, 5-, 6-, 7-, 8- or 9-oxadecyl.

An alkyl radical R in which a $CH_2$ group is replaced by —CH=CH— can be straight-chain or branched. It is preferably straight-chain and has 2 to 10 carbon atoms. Accordingly, it is in particular vinyl, prop-1-, or prop-2-enyl, but-1-, but-2- or but-3-enyl, pent-1-, pent-2-, pent-3- or pent-4-enyl, hex-1-, hex-2-, hex-3-, hex-4- or hex-5 -enyl, hept-1-, hept-2-, hept-3 -, hept-4-, hept-5 - or hept-6-enyl, oct-1-, oct-2-, oct-3-, oct-4-, oct-5-, oct-6- or oct-7-enyl, non-1-, non-2-, non-3-, non-4-, non-5-, non-6-, non-7- or non-8-enyl, dec-1-, dec-2-, dec-3-, dec-4-, dec-5-, dec-6-, dec-7-, dec-8- or dec-9-enyl.

In an alkyl radical R in which one $CH_2$ group is replaced by —O— and by —CO—, these groups are preferably adjacent. Accordingly, they contain one acyloxy group —CO—O— or one oxycarbonyl group —O—CO—. Preferably, these are straight-chain and have 2 to 6 carbon atoms.

Accordingly, they are in particular acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)butyl.

An alkyl radical R in which one $CH_2$ group is replaced by unsubstituted or substituted —CH=CH— and one adjacent $CH_2$ group by CO or CO—O or O—CO— can be straight-chain or branched. It is preferably straight-chain and has 4 to 13 carbon atoms. Accordingly it is in particular acryloyloxymethyl, 2-acryloyloxymethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl, 9-methacryloyloxynonyl.

An alkyl or alkenyl radical R which is monosubstituted by CN or $CF_3$ is preferably a straight-chain radical and the substitution by CN or $CF_3$ is in the ω-position.

An alkyl or alkenyl radical R which is at least monosubstituted by halogen is preferably a straight-chain radical and halogen is preferably F or Cl. In the case of multiple substitution, halogen is preferably F. The resulting radicals also include perfluorinated radicals.

In the case of monosubstitution, the fluorine or chlorine substituent may be in any desired position, but is preferably in the ω-position.

Compounds of the formula I" containing wing groups suitable for polymerization reactions are suitable for preparing liquid-crystalline polymers.

Compounds of the formula I" having branched wing groups R can occasionally be of importance due to better solubility in the conventional liquid-crystalline base materials, but in particular as chiral doping substances, provided they are optically active. Smectic compounds of this type are suitable as components for ferroelectric materials.

Compounds of the formula I" having $S_A$ phases are suitable, for example, for thermally addressed displays.

Branched groups of this type, as a rule, do not contain more than one chain branching. Preferred branched radicals R are isopropyl, 2-butyl (=1-methylpropyl), isobutyl (=2-methylpropyl), 2-methylbutyl, isopentyl (=3methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy.

An alkyl radical R in which two or more $CH_2$ groups are replaced by —O— and/or —CO—O— can be straight-chain or branched. It is preferably branched and has 3 to 12 carbon atoms. Accordingly, it is in particular bis(carboxy)methyl, 2,2-bis(carboxy)ethyl, 3,3-bis(carboxy)propyl, 4,4-bis(carboxy)butyl, 5,5-bis(carboxy)pentyl, 6,6-bis(carboxy)hexyl, 7,7-bis(carboxy)heptyl, 8,8-bis(carboxy)octyl, 9,9-bis(carboxy)nonyl, 10,10-bis(carboxy)decyl, bis(methoxycarbonyl)methyl 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3 bis(ethoxycarbonyl)propyl, 4,4-bis(ethoxycarbonyl)butyl, 5,5-bis(ethoxycarbonyl)hexyl.

Compounds of the formula I" containing wing groups R suitable for polycondensations are suitable for preparing liquid-crystalline polycondensation products.

Formula I" comprises not only the racemates of these compounds but also the optical antipodes and mixtures thereof.

Of these compounds of the formula I" and the subformulae thereof, those are preferred in which at least one of the radicals contained therein has one of the preferred meanings mentioned.

In the compounds of the formula I", those stereoisomers are preferred in which the rings Cyc and piperidine are trans-1,4-disubstituted. Those of the above-mentioned formulae containing one or more groups Pyd, Pyr and/or Dio each comprise the two isomers in the 2,5-position.

A few very particularly preferred smaller groups of compounds of formula I" are those of the subformulae I1 to I11:

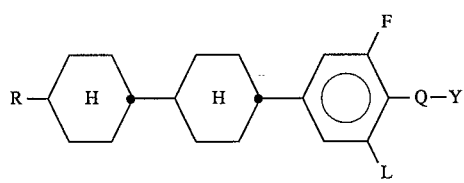
I1

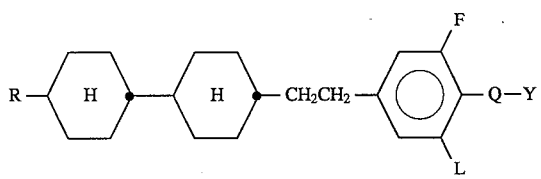
I2

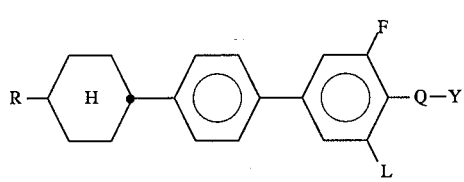
I3

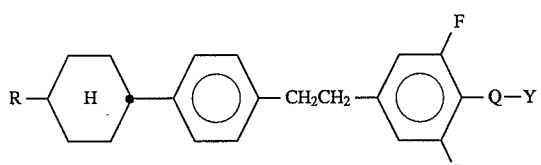
I4

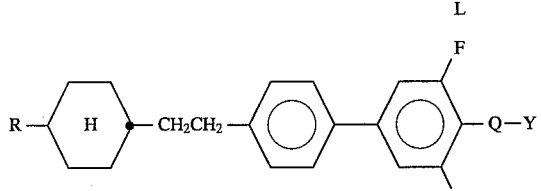
I5

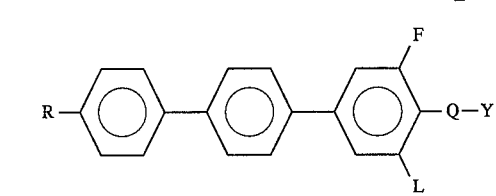
I6

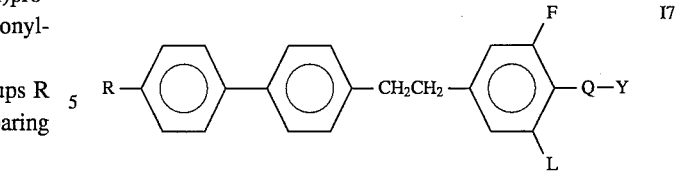
I7

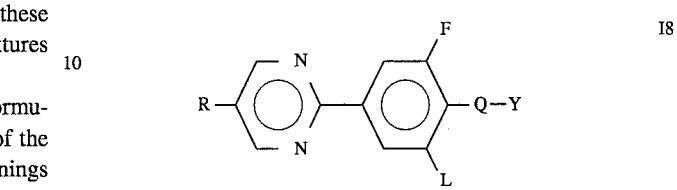
I8

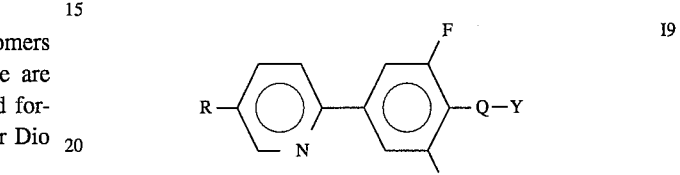
I9

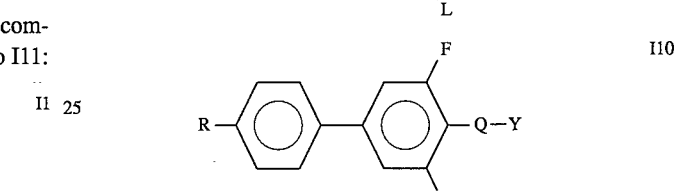
I10

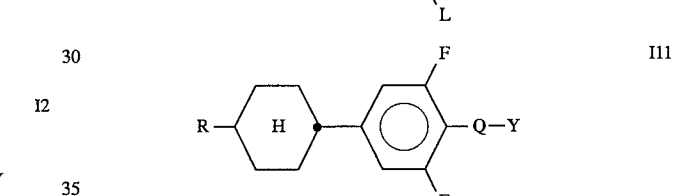
I11

The 1,4-cyclohexenylene group, Che, of formula I" and its subformulae preferably has the following structures:

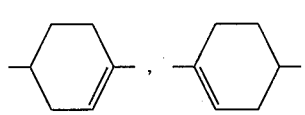

The compounds of the formula I" are prepared by methods known per se, such as are described in the literature (e.g. in the standard works such as Houben-Weyl, Methoden der Organischen Chemie [Methods of Organic Chemistry], Georg-Thieme-Verlag, Stuttgart Vol. IX, p. 867 ff.), under reaction conditions known and suitable for the reactions mentioned.

It is also possible to use variations known per se and not mentioned here in more detail.

The compounds according to the invention can be prepared, for example, by metalating a compound of the formula II"

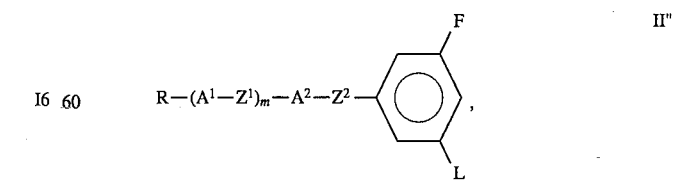
II"

in which R, $A^1$, $A^2$, $Z^1$, $Z^2$ and m have the meaning mentioned for formula I", in accordance with the reaction scheme below and then reacting the product with a suitable electrophile:

Scheme 1

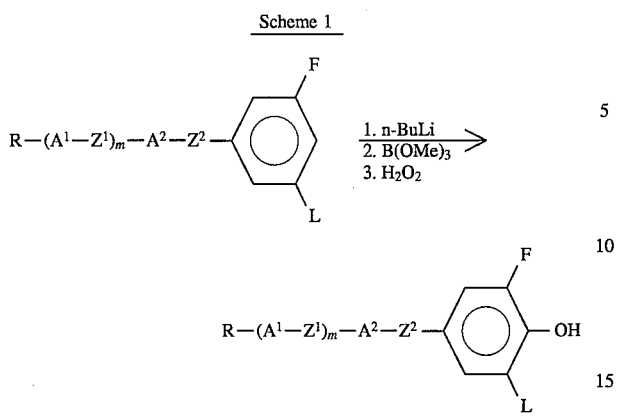

The target products where Q is $OCF_2$ or OCHF can be obtained from the phenol formed by known methods, for example by reaction with chlorodifluoromethane or carbon tetrachloride/HF.

Further methods of synthesis are evident to one skilled in the art. For example, 1,3-difluorobenzene compounds appropriately substituted in the 5 position or monofluorinated analogues (L=H) can be converted according to the above scheme to the 2-$OCF_2$Y-1,3-difluoro compounds or to the mono-fluorinated analogues (L=H) and the radical $R—(A^1—Z^1)_m—A^2—Z^2$ can then be introduced via reactions customary in liquid-crystal chemistry (e.g. esterification, etherification or coupling reactions, for example as described in E. Poetsch, Kontakte (Darmstadt) 1988 (2), p.15).

Scheme 2

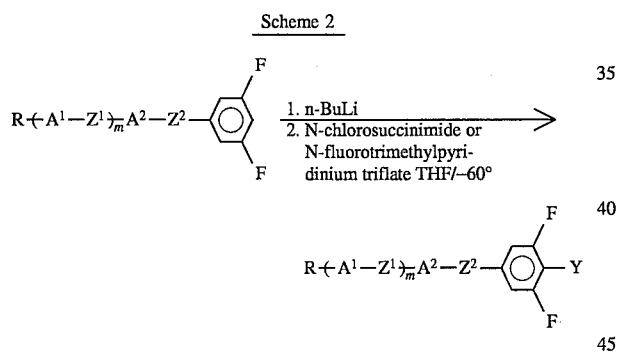

Further methods of synthesis are evident to one skilled in the art, For example, 1,3-difluorobenzene compounds appropriately substituted in the 5 position can be converted in accordance with the above scheme to the 2-Y-1,3-difluoro compounds and the radical $R—(A^1—Z^1)_m—A^2—Z^2$ can then be led by reactions customary in liquid-crystal chemistry (e.g. esterification, etherification or coupling reactions, for example as described in E. Poetsch, Kontakte (Darmstadt) 1988 (2), p. 15).

The compounds according to the invention of the formula I" in which l is F and Q—Y is $CF_3$ can be prepared by metalation of the unsubstituted 3,5-difluorophenyl compounds where n-BuLi, followed by reaction with iodine and reaction of the iodine compound with sodium trifluoroacetate according to the following scheme:

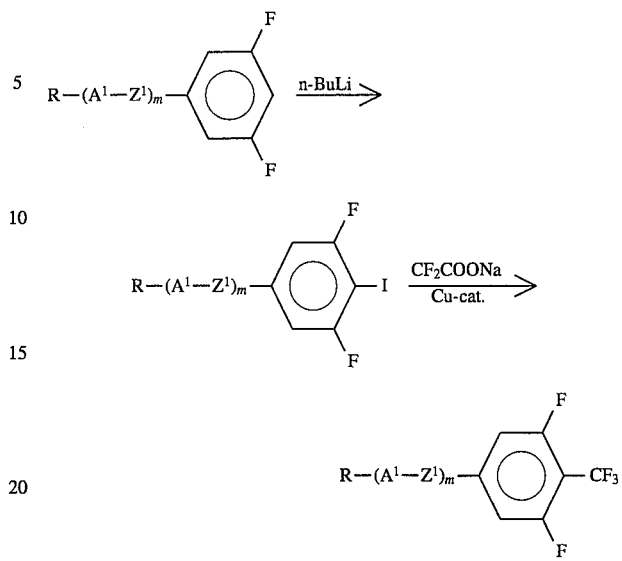

The compounds according to the invention where L is H and Q—Y is $CF_3$ can be prepared by converting 3-fluoro-4-iodobromobenzene to the benzotrifluoride compound with $CF_3COONa$ and then introducing the radical $R—(A^1—Z^1)_m$, for

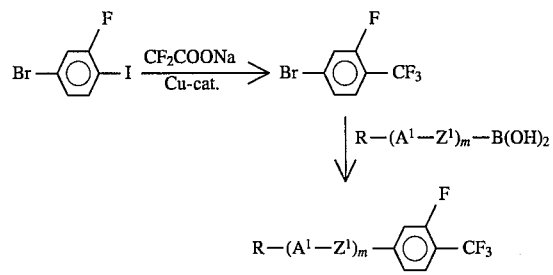

The compounds of the formula II" can be prepared, for example, according to the following synthetic schemes:

Scheme 3

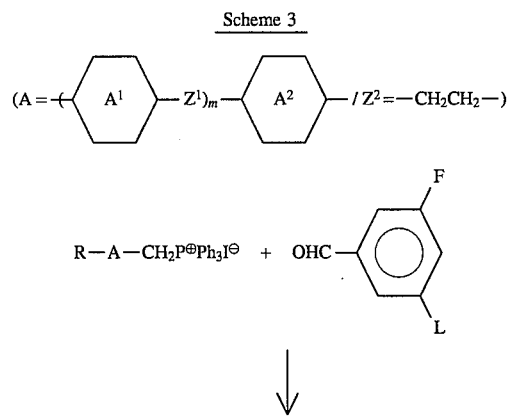

Scheme 3 -continued

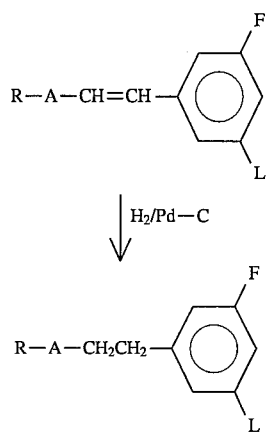

Scheme 4

$(A = -(A^1-Z^1)_m-A^2-/Z^2 = \text{single bond})$

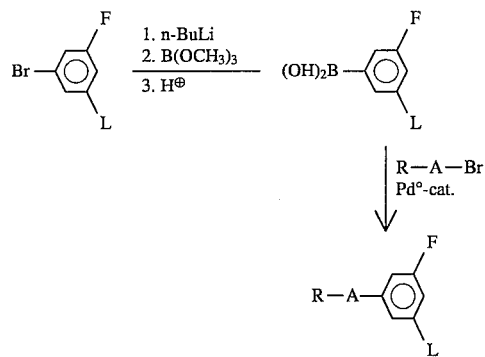

Scheme 5

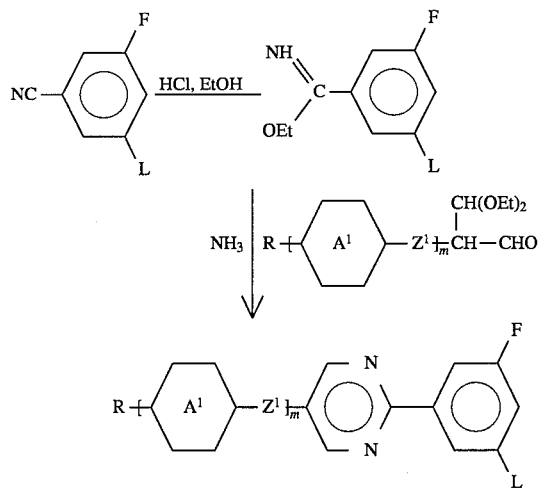

Scheme 6

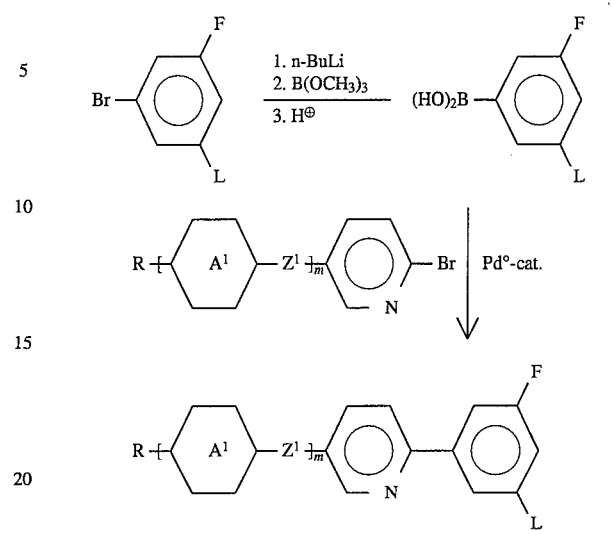

Scheme 7

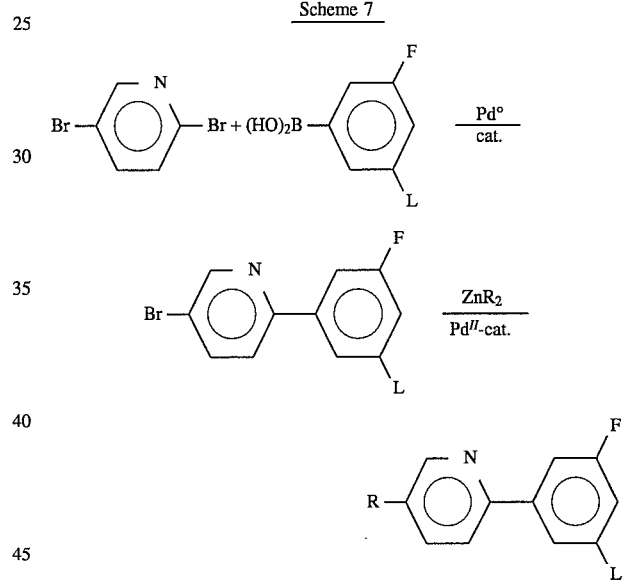

The starting materials are either known or can be prepared in analogy with known compounds.

Esters of the formula I″ can also be obtained by esterification of the corresponding carboxylic acids (or reactive derivatives thereof) with alcohols or phenols (or reactive derivatives thereof) or by the DCC method (DCC=dicyclohexylcarbodiimide).

The corresponding carboxylic acids and alcohols and phenols are known or can be prepared in analogy with known processes.

The synthesis of a few particularly preferred compounds is detailed below:

Scheme 8
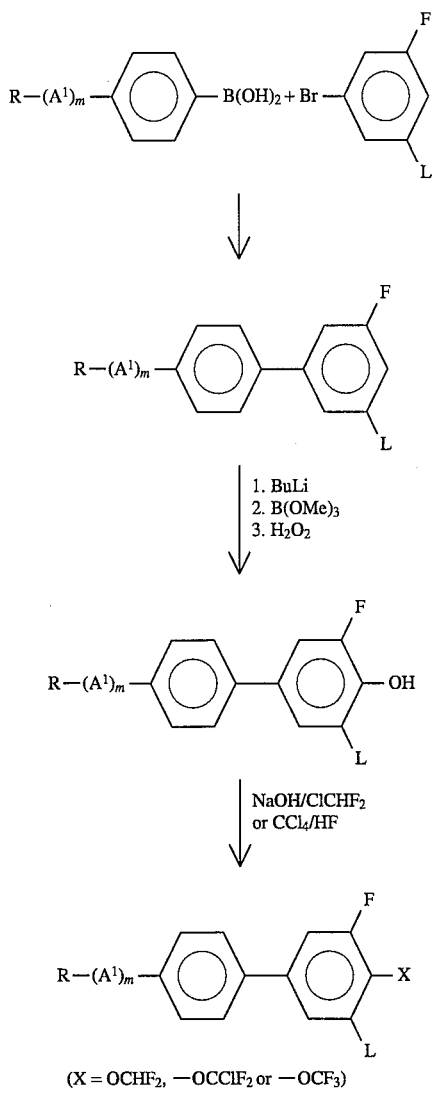
Scheme 9
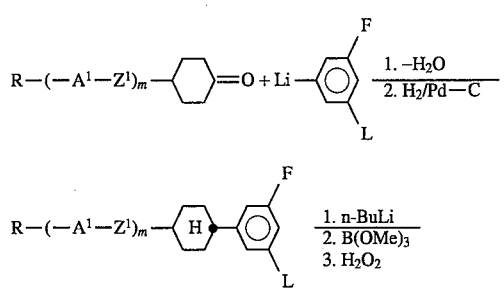
-continued
Scheme 9
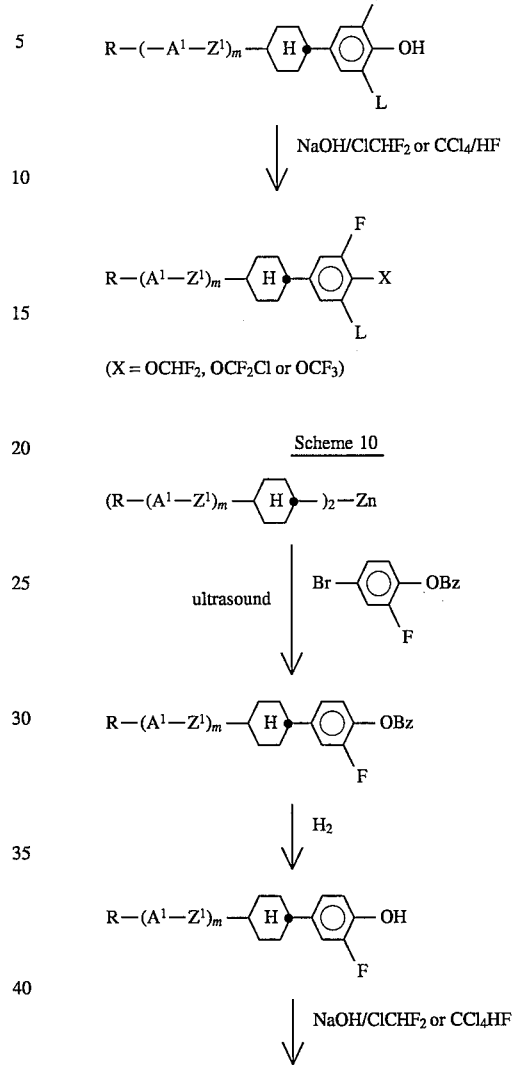
In schemes 8, 9 and 10, m is preferably 0 or 1 and —$A^1$—$Z^1$ is
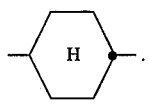

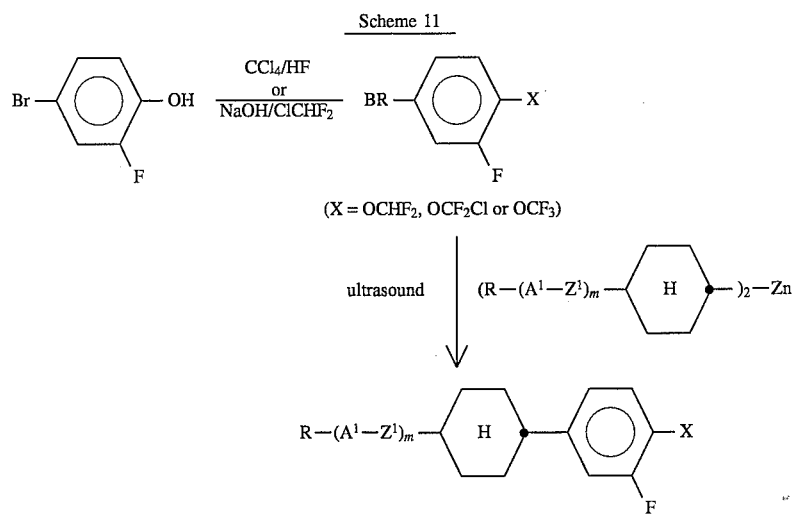
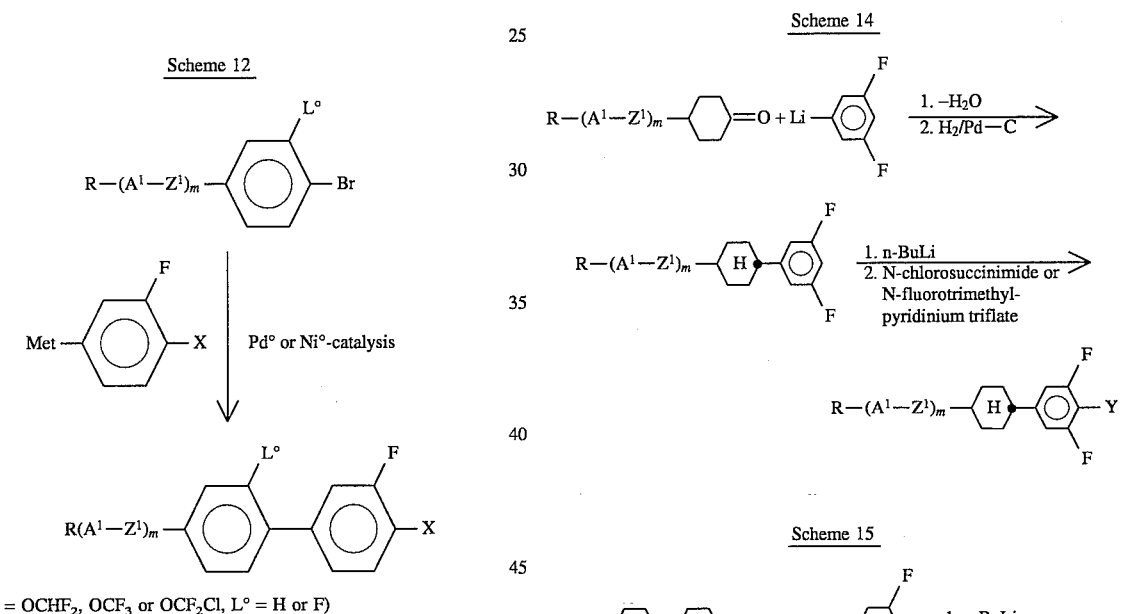
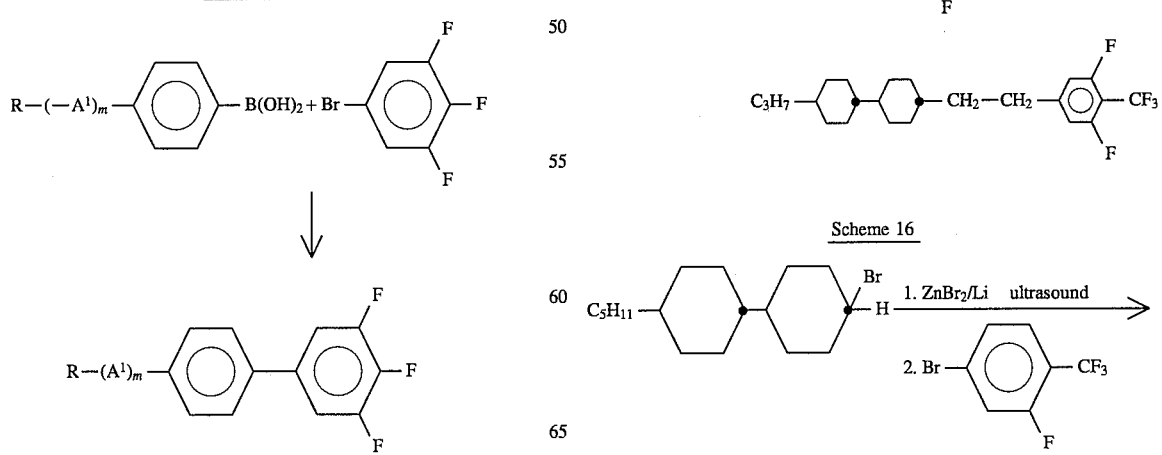

-continued
Scheme 16
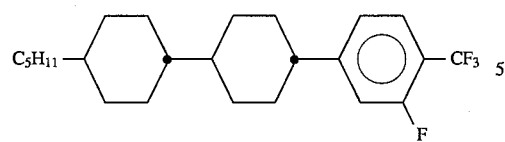
Scheme 17
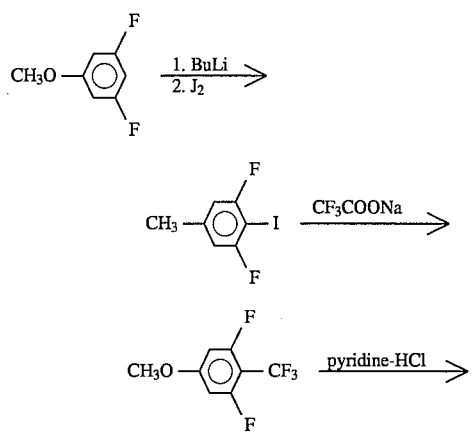
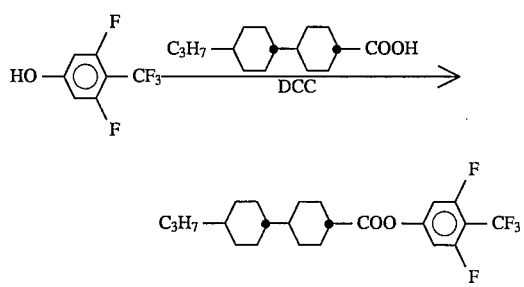
Scheme 18
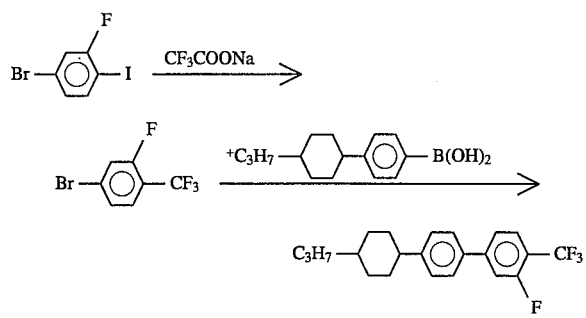
Scheme 19
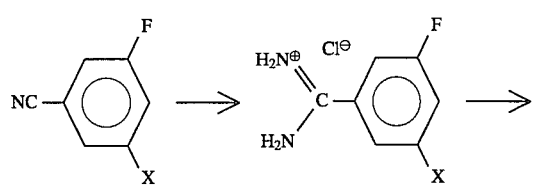
-continued
Scheme 19
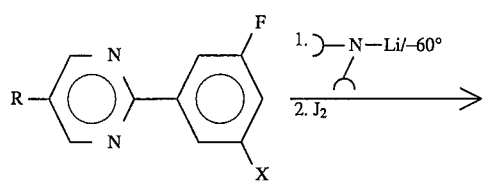
Scheme 20
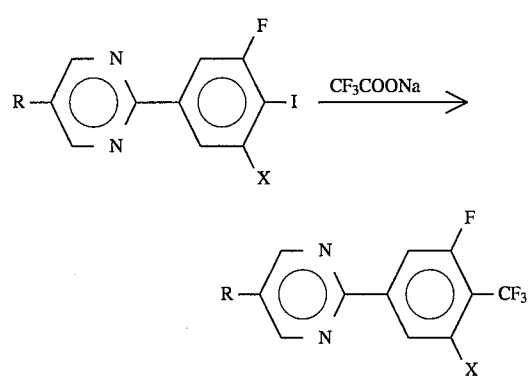
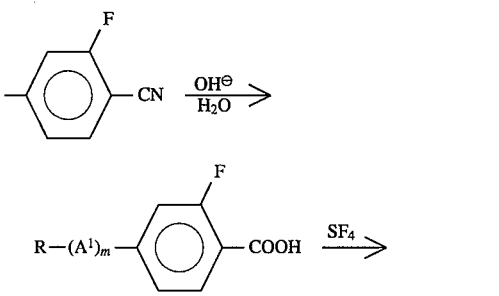
Scheme 21
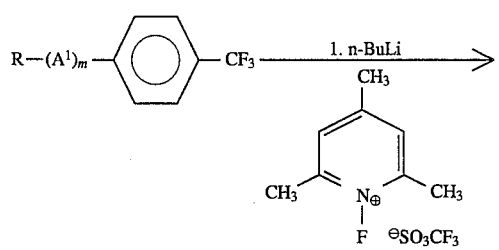

-continued
Scheme 21

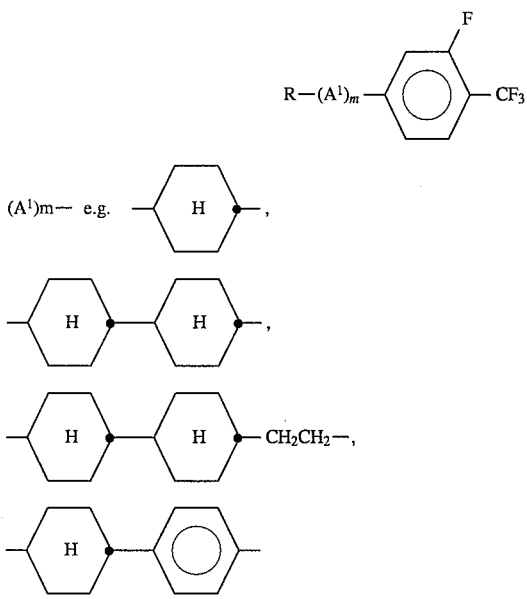

Esters of the formula I" can also be obtained by esterification of corresponding carboxylic acids (or their reactive derivatives) with alcohols or phenols (or their reactive derivatives) or by the DCC method (DCC=dicyclohexylcarbodiimide).

The corresponding carboxylic acids and alcohols or phenols are known or can be prepared in analogy to known processes.

In a further process for the preparation of the compounds of the formula I", an aryl halide is reacted with an olefin in the presence of a tertiary amine and a palladium catalyst (cf. R. F. Heck, Acc. Chem. Res. 12 (1979) 146). Examples of suitable aryl halides are chlorides, bromides and iodides, in particular bromides and iodides. The tertiary amines which are necessary for the coupling reaction to succeed, such as, for example, triethylamine, are also suitable as solvents. Examples of suitable palladium catalysts are palladium salts, in particular Pd(II) acetate, with organic phosphorus(III) compounds, such as, for example, triarylphosphanes. The reaction can be carried out in the presence or absence of an inert solvent at temperatures between about 0° and 150°, preferably between 20° and 100°; examples of suitable solvents are nitriles, such as acetonitriles, or hydrocarbons, such as benzene or toluene. The aryl halides and olefins which are used as starting materials are commercially available in large numbers or can be prepared by processes known from the literature, for example by halogenation of the corresponding parent compounds or by elimination reactions performed on the corresponding alcohols or halides.

In this manner, it is, for example, possible to prepare stilbene derivatives. The stilbenes can furthermore be prepared by reaction of a 4-substituted benzaldehyde with the corresponding phosphorus ylide, according to Wittig. However, it is also possible to prepare tolans of the formula I" by using monosubstituted acetylene instead of the olefin (Synthesis 627 (1980) or Tetrahedron Lett. 27, 1171 (1986)).

Furthermore, in order to couple aromatics, aryl halides can be reacted with aryltin compounds. These reactions are preferably carried out with the addition of a catalyst, such as, for example, a palladium(0) complex, in inert solvents, such as hydrocarbons, at elevated temperatures, for example in boiling xylene, under an inert gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I" can also be prepared via the Fritsch-Buttenberg-Wiechell rearrangement (Ann. 279, 319, 1984), in which 1,1-diaryl-2-halogenoethylenes are rearranged to diarylacetylenes in the presence of strong bases.

Tolans of the formula I" can also be prepared by brominating the corresponding stilbenes and then subjecting the product to dehydrohalogenation. It is possible to use variations known per se of this reaction not mentioned here in more detail.

Ethers of the formula I" can be obtained by etherification of the corresponding hydroxy compounds, preferably of the corresponding phenols, in which the hydroxy compound is preferably first converted to the corresponding metal derivative, for example by treatment with NaH, NaNH$_2$, NaOH, KOH, Na$_2$CO$_3$ or K$_2$CO$_3$ to the corresponding alkali metal alcoholate or alkali metal phenolate. This derivative can then be reacted with the corresponding alkyl halide, alkyl sulfonate or dialkyl sulfate, preferably in an inert solvent, such as, for example, acetone, 1,2-dimethoxyethane, DMF or dimethyl sulfoxide or even with excess aqueous or aqueous-alcoholic NaOH or KOH at temperatures between about 20° and 100°.

The starting materials are either known or can be prepared in analogy to known compounds.

The compounds of the formula I''' where $Z^2$=—(CH$_2$)$_4$— can be prepared by the following scheme:

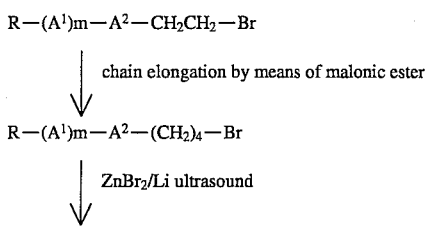

-continued

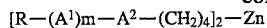

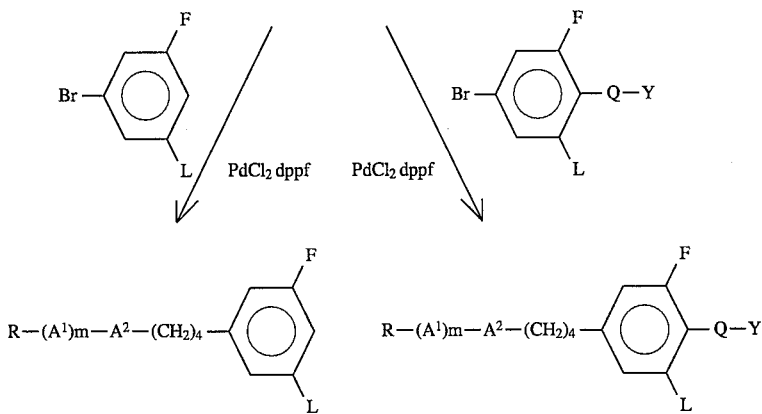

In the Pd(II)-catalyzed coupling reaction, either the target product I''' is formed directly or a precursor in which the radical —Q—Y is introduced completely analogously to the above methods for compounds of formula I''.

The compounds of the formula I''' where $Z^2=$—CH=CH—CH$_2$CH$_2$— can be prepared via Wittig as in the following scheme:

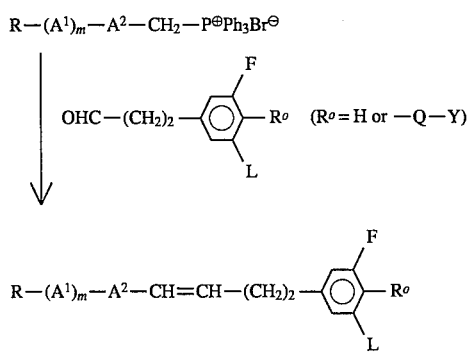

The preferred trans isomers can be prepared by the isomerization methods known from the literature. The precursors where R°=H which may be obtained are converted into the compounds of the formula I''' completely analogously to the precursors of the compounds of the formula I'' by introducing the radical —Q—Y.

The aldehydes can be obtained by Heck reaction of appropriately substituted 1-bromo-3-fluorobenzene derivatives with allyl alcohol.

The liquid-crystalline media according to an aspect of the invention preferably contain, in addition to one or more compounds according to formula I''2 to 40, in particular 4 to 30 further components. These media very particularly preferably contain, in addition to one or more compounds according to formula I'', 7 to 25 components. These further components are preferably selected from nematic or nematogenic (monotropic or isotropic) substances, in particular substances from the classes of azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl benzoates, cyclohexanecarboxylates or cyclohexylcyclohexanecarboxylates, phenylcyclohexanes, cyclohexylbiphenyls, phenylcyclohexylcyclohexanes, cyclohexylcyclohexanes, cyclohexylcyclohexylcyclohexenes, 1,4-bis(cyclohexyl)benzenes, 4,4'-bis(cyclohexyl)biphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, halogenated or unhalogenated stilbenes, benzyl phenyl ethers, tolans and substituted cinammic acids. The 1,4-phenylene groups in these compounds can also be fluorinated.

The most important compounds which are suitable as further components of media according to an aspect of the invention can be characterized by the formulae 1c, 2c, 3c, 4c and 5c:

| | |
|---|---|
| R'—L—E—R'' | 1c |
| R'—L—COO—E—R'' | 2c |
| R'—L—OOC—E—R'' | 3c |
| R'—L—CH$_2$CH$_2$—E—R'' | 4c |
| R'—L—C≡C—E—R'' | 5C |

In the formulae 1c, 2c, 3c, 4c and 5c, L and E, which can be identical or different, are in each case independently of one another, are a divalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, in which Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Bio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

Preferably, one of the radicals L and E is Cyc, Phe or Pyr. E is preferably Cyc, Phe or Phe—Cyc. The media according to an aspect of the invention preferably contain one or more components selected from the compounds of the formulae 1c, 2c, 3c, 4c and 5c, in which L and E are selected from the group comprising Cyc, Phe and Pyr and simultaneously one or more components selected from the compounds of the 1c, 2c, 3c, 4c and 5c, in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and, if desired, one or more components selected from the compounds of the formulae 1c, 2c, 3c, 4c and 5c, in which the radicals 1 and E are selected from the group —Phe—Cyc—, —Cyc—Cyc—, —G—Phe— and —G—Cyc—.

R' and R", in a similar subgroup of the compounds of the formulae 1c, 2c, 3c, 4c and 5c, are in each case independently of one another alkyl, alkenyl, alkoxy, alkoxyalkyl, alkenyloxy or alkanoyloxy having up to 8 carbon atoms. In the following, this smaller subgroup is named group A and the compounds are denoted by the subformulae 1d, 2d, 3d, 4d and 5d. In most of these compounds, R' and R" are different from one another, one of these radicals usually being alkyl, alkenyl, alkoxy or alkoxyalkyl.

In another smaller subgroup of the compounds of the formulae 1c, 2c, 3c, 4c and 5c named group B, R" is —F, —Cl, —NCS or —(O)$_i$CH$_{3-(k+l)}$F$_k$Cl$_l$, where i is 0 or 1 and k+l is 1, 2 or 3; the compounds in which R" has this meaning are denoted by the subformulae 1e, 2e, 3e, 4e and 5e. Particularly preferred compounds are those of the subformulae 1e, 2e, 3e, 4e and 5e in which R" has the meaning —F, —Cl, —NCS, —CF$_3$, —OCHF$_2$ or —OCF$_3$.

In the compounds of the subformulae 1e, 2e, 3e, 4e and 5e, R' has the meaning indicated for the compounds of the subformulae 1d–5d and is preferably alkyl, alkenyl, alkoxy or alkoxyalkyl.

In a further smaller subgroup of the compounds of the formulae 1c, 2c, 3c, 4c and 5c, R" is —CN; this subgroup is denoted as group C in the following and the compounds of this subgroup are correspondingly described by subformulae 1f, 2f, 3f, 4f and 5f. In the compounds of the subformulae 1f, 2f, 3f, 4f and 5f, R' has the meaning indicated for the compounds of the subformulae 1d–5d and is preferably alkyl, alkoxy or alkenyl.

In addition to the preferred compounds of the groups A, B and C, other compounds of the formulae 1c, 2c, 3c, 4c and 5c having other variants of the intended substituents are also customary. All these substances are obtainable by methods which are known in the literature or in analogy to these.

In addition to compounds of the formula I" according to the invention, the media according to the invention preferably contain one or more compounds which are selected from the group A and/or group B and/or group C. The proportions by weight of the compounds of these groups in the media according to an aspect of the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50% the sum of the proportions by weight of the compounds of the groups A and/or B and/or C contained in the respective media according to an aspect of the invention preferably being 5%–90% and in particular 10% to 90%.

The media according to an aspect of the invention preferably contain 1 to 40%, particularly preferably 5 to 30%, of the compounds according to formula I" of the invention. Media containing more than 40%, in particular 45 to 90%, of the compounds according to formula I" of the invention are furthermore preferred. The media preferably contain three, four or five compounds according to formula I" of the invention.

The media according to the invention are prepared in a manner customary per se. As a rule, the components are dissolved in one another, preferably at elevated temperature. By means of suitable additives, the liquid-crystalline phases according to the invention can be modified in such a manner that they can be used in all previously known types of liquid-crystal display elements. These types of additives are known to one skilled in the art and have been described in detail in the literature (H. Kelker/R. Hatz, Handbook of Liquid Crystals, Verlag Chemie, Weinheim, 1980). For example, pleochroic dyes for preparing coloured guest-host systems or substances for changing the dielectric anisotropy, the viscosity and/or the orientation of the nematic phases can be added.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding applications German P 37 32 284.2, filed Sep. 25, 1987; German P 38 25 425.5, filed Jul. 27, 1988; German P 39 09 802.8, filed Mar. 24, 1989; German P 39 29 525.7, filed Sep. 6, 1989; German P 39 29 526.5, filed Sep. 6, 1989; German P 40 09 907.5, filed Mar. 28, 1990; and German P 39 29 764.0, filed Sep. 7, 1989, are hereby incorporated by reference.

EXAMPLES

The examples which follow are intended to illustrate the invention without limiting it. Above and below, percentages are by weight. All temperatures are given in degrees centigrade. m.p. denotes melting point and c.p.=clear point. Furthermore, C denotes crystalline state, N nematic phase, S smectic phase and I isotropic phase. The data between these symbols represent the transition temperatures. $\Delta$n denotes optical anisotropy (589 nm, 20° C.) and viscosity (mm$^2$/sec) was determined at 20° C.

"Usual work-up" means: if desired, water is added, the product is extracted with methylene chloride, diethyl ether or toluene, the organic phase is separated off, dried, evaporated, and the product is purified by distillation under reduced pressure or crystallization and/or chromatography. The following abbreviations are used:
DAST—diethylaminosulfur trifluoride
DCC—dicyclohexylcarbodiimide
DDQ—dichlorodicyanobenzoquinone
DIBALH—diisobutylaluminum hydride
KOT—potassium t-butoxide
THF—tetrahydrofuran
pTSOH—p-toluenesulfonic acid
TMEDA—tetramethylethylenediamine.

Example 1

0.1 mol of p-trifluormethoxybenzaldehyde, 0.1 mol of ethylpropanediol and 0.2 g of p-toluenesulfonic acid are refluxed for 2 hours in 100 ml of toluene. After evaporation of the solvent, vacuum distillation and subsequent crystallization, trifluoromethoxy-4-(5-ethyl-1,3-dioxan-2 -yl)benzene of m.p.=31° and c.p. (extr.)=–90° is obtained.

The following are prepared analogously:
Trifluoromethoxy-4-(5-propyl-1,3-dioxan-2-yl)benzene, m.p. 36.3°, c.p. 35°

Trifluoromethoxy-4-(5-butyl-1,3-dioxan-2-yl)benzene
Trifluoromethoxy-4-(5-pentyl-1,3-dioxan-2-yl)benzene, m.p.23°, c.p. 36°
Trifluoromethoxy-4-(5-hexyl-1,3-dioxan-2-yl)benzene
Trifluoromethoxy-4-(5-heptyl-1,3-dioxan-2-yl)benzene
Trifluoromethoxy-4-(5-octyl-1,3-dioxan-2-yl)benzene
Trifluoromethoxy-4-(5-nonyl-1,3-dioxan-2-yl)benzene
Trifluoromethoxy-4-(5-decyl-1,3-dioxan-2-yl)benzene
Trifluoromethoxy-4-[5-(trans-4-ethylcyclohexyl)-1,3-dioxan-2-yl]benzene
Trifluoromethoxy-4-[5-(trans-4-propylcyclohexyl)-1,3-dioxan-2-yl]benzene
Trifluoromethoxy-4-[5-(trans-4-butylcyclohexyl)-1,3-dioxan-2-yl]benzene
Trifluoromethoxy-4-[5-(trans-4-pentylcyclohexyl)-1,3-dioxan-2-yl]benzene, C 67° $S_B$ 146° N 150.5° I
Trifluoromethoxy-4-[5-(trans-4-hexylcyclohexyl)-1,3-dioxan-2-yl]benzene
Trifluoromethoxy-4-[5-(trans-4-heptylcyclohexyl)-1,3-dioxan-2-yl]benzene Example 2

2 mol of anhydrous hydrofluoric acid are transferred into an autoclave which has been cooled to 0°. A mixture of 0.18 mol of tetrachloromethane and 0.06 mol of 4-(trans-4-ethylcyclohexyl)phenol is then added. The mixture is stirred for about 8 hours at 150°, cooled, poured into ice water and washed with ether. The two phases are stirred for about 30 minutes and separated, and the ether solution is washed with 5% KOH until alkaline. After drying, filtering off, distilling off and purification, trifluoromethoxy-4-(trans-ethylcyclohexyl)benzene is obtained.

The following are pre pared analogously:
Trifluoromethoxy-4-(trans-4-propylcyclohexyl)benzene
Trifluoromethoxy-4-(trans-4-butylcyclohexyl)benzene
Trifluoromethoxy-4-(trans-4-pentylcyclohexyl)benzene
Trifluoromethoxy-4-(trans-4-hexylcyclohexyl)benzene
Trifluoromethoxy-4-(trans-4-heptylcyclohexyl)benzene
Trifluoromethoxy-4-(trans-4-octylcyclohexyl)benzene
Trifluoromethoxy-4-(trans-4-nonylcyclohexyl)benzene
Trifluoromethoxy-4-(trans-4-decylcyclohexyl)benzene Example 3

0.42 g of lithium and 3.5 g of ZnBr$_2$ are added to a mixture of 8.6 g of trans-4-(trans-4-propylcyclo-hexyl)cyclohexyl bromide and 50 ml of THF/toluene (1:4) at 0°. The reaction solution is treated with ultrasound for 3 hours at 0°–10°. After addition of 7.4 g of 1-bromo-4 -(trifluoromethoxy)benzene and 0.44 g of 1,1-bis(diphenyl-phosphino)-ferrocene-palladium (II) dichloride [PdCl$_2$ (dppf)], the mixture is stirred at room temperature for 24 hours, poured into 25 ml of water (+5 ml of 1N HCl) and stirred for 15 minutes, the organic phase is separated off, and the aqueous phase is extracted with toluene.

After work-up of the organic phases and purification by chromatography and/or crystallization, trifluoromethoxy-4-[trans-4-(trans-4-propylcyclohexyl)-cyclohexyl]-benzene is obtained, C 39° S 68° N148.6° I.

The following are prepared analogously:
Trifluoromethoxy-4-[trans-4-(trans-4-ethylcyclohexyl)cyclohexyl]benzene
Trifluoromethoxy-4-[trans-4-(trans-4-butylcyclohexyl)cyclohexyl]benzene
Trifluoromethoxy-4-[trans-4-(trans-4-pentylcyclohexyl)cyclohexyl]benzene
Trifluoromethoxy-4-[trans-4-(trans-4-hexylcyclohexyl)cyclohexyl]benzene
Trifluoromethoxy-4-[trans-4-(trans-4-heptylcyclohexyl)cyclohexyl]benzene
Trifluoromethoxy-4-[trans-4-(trans-4-octylcyclohexyl)cyclohexyl]benzene
Trifluoromethoxy-4-[trans-4-(trans-4-nonylcyclohexyl)cyclohexyl]benzene
Trifluoromethoxy-4-[trans-4-(trans-4-decylcyclohexyl)cyclohexyl]benzene Example 4

By etherification of 50 mmol of trifluoromethoxy-p-hydroxymethylbenzene with 50 mmol of 2-(p-hydroxybenzene)- 5-nonylpyrimidine (sic) in 150 ml of THF in the presence of 55 mmol of triphenylphosphine and 55 mmol of diethyl azodi-carboxylate, 4-(5-nonylpyrimidin-2-yl)-phenyl p-trifluoro-methoxybenzyl ether of m.p.=56° and c.p.= 155° is obtained, The following are obtained analogously:
4-(5-Ethylpyrimidin-2-yl)phenyl p-trifluoromethoxybenzyl ether
4-(5-Methylpyrimidin-2-yl)phenyl p-trifluoromethoxybenzyl ether
4-(5-Propylpyrimidin-2-yl)phenyl p-trifluoromethoxybenzyl ether
4-(5-Butylpyrimidin-2-yl)phenyl p-trifluoromethoxybenzyl ether
4-(5-Pentylpyrimidin-2-yl)phenyl p-trifluoromethoxybenzyl ether
4-(5-Hexylpyrimidin-2-yl)phenyl p-trifluoromethoxybenzyl ether
4-(5-Heptylpyrimidin-2-yl)phenyl p-trifluoromethoxybenzyl ether
4-(5-Octylpyrimidin-2-yl)phenyl p-trifluoromethoxybenzyl ether Example 5

Equimolar amounts of p-trifluoromethoxybenzimidamide hydrochloride (can be prepared from the corresponding nitrile via the corresponding ethyl benzimidate hydrochloride) and heptylmalondialdehyde bisdiethyl acetal are heated at 150° for 15 hours. After cooling, the residue is dissolved in ethanol. Customary work-up gives 2 -(p-trifluoromethoxybenzene )-5-heptylpyrimidine of m.p. 23° and c .p. 34°.

The following are prepared analogously:
2-(p-Trifluoromethoxybenzene)-5-ethylpyrimidine
2-(p-Trifluoromethoxybenzene)-5-propylpyrimidine
2-(p-Trifluoromethoxybenzene)-5-butylpyrimidine
2-(p-Trifluoromethoxybenzene)-5-pentylpyrimidine
2-(p-Trifluoromethoxybenzene)-5-hexylpyrimidine
2-(p-Trifluoromethoxybenzene)-5-methoxypyrimidine
2-(p-Trifluoromethoxybenzene)-5-ethoxypyrimidine
2-(p-Trifluoromethoxybenzene)-5-propoxypyrimidine
2-(p-Trifluoromethoxybenzene)-5-butoxypyrimidine
2-(p-Trifluoromethoxybenzene)-5-pentyloxypyrimidine
2-(p-Trifluoromethoxybenzene)-5-hexyloxypyrimidine
2-(p-Trifluoromethoxybenzene)-5-heptyloxypyrimidine Example 6 a) 95 g of trifluoromethoxybenzaldehyde in 150 ml of THF are added over the course of 2–3 hours at −10° to −5° to a mixture of 300 g of trans-4-(trans-4-propylcyclohexyl)cyclohexylmethyltriphenylphosphonium iodide, 56 g of potassium tert.-butoxide and 500 ml of THF. The mixture is allowed to warm to room temperature and neutralized using 2N HCl, water is added, and the mixture is extracted with methyl tert.-butyl ether. After work-up of the organic phase and purification by chromatography on silica gel, 1-(4-trifluoromethoxyphenyl)- 2-[trans-4-(trans-4-propylcyclohexyl)cyclohexyl]ethene is obtained.

b) 162 g of the ethene derivative are hydrogenated at room temperature and atmospheric pressure in 800 ml of THF over 40 g of 5% Pd/C. After work-up and purification by crystallization, 1-(4-trifluoromethoxyphenyl)-2 -[trans-4-(trans-4-propylcyclohexyl)-cyclohexyl]ethane having C 24° C 60° $S_G$ 76° N 133.7° I is obtained.

The following are prepared analogously:
1-(4-Trifluoromethoxyphenyl)-2-[trans-4-(trans-4-ethylcyclohexyl)cyclohexyl]ethane
1-(4-Trifluoromethoxyphenyl)-2-[trans-4-(trans-4-butylcyclohexyl)cyclohexyl]ethane
1-(4-Trifluoromethoxyphenyl)-2-[trans-4-(trans-4-pentylcyclohexyl)cyclohexyl]ethane, C44° $S_B$ 108° N139° I
1-(4-Trifluoromethoxyphenyl)-2-[trans-4-(trans-4-hexylcyclohexyl)cyclohexyl]ethane
1-(4-Trifluoromethoxyphenyl)-2-[trans-4-(trans-4-heptylcyclohexyl)cyclohexyl]ethane

Example 7

15.5 g of 1-bromo-4-(trans-4-pentylcyclohexyl)benzene in 50 ml of THF are added to a boiling mixture of 1.2 g of magnesium and 25 ml of THF. When the addition is complete, the mixture is heated for a further 1 hour, cooled and added to a solution of 6.7 g of $ZnBr_2$ in 50 ml of THF at 0°–15°. After stirring for 1 hour, 12.3 g of 1-bromo-4-(trifluoromethoxy)benzene and 0.75 g of $PdCl_2$ (dppf) are added. The mixture is stirred at 5° for 15 minutes and then at room temperature for 24 hours. The mixture is poured onto 100 ml of saturated $NH_4Cl$ solution, and the organic phase is separated off and extracted with toluene. After work-up of the organic phase and purification by chromatography and/or crystallization, trifluoromethoxy-4 -[4-(trans-4-pentyl-cyclohexyl)phenyl]benzene, C 43° $S_B$ 128° N 147.4° I is obtained.

The following are prepared analogously:
Trifluoromethoxy-4-[4-(trans-4-ethylcyclohexyl)phenyl]benzene
Trifluoromethoxy-4-[4-(trans-4-propylcyclohexyl)phenyl]benzene
Trifluoromethoxy-4-[4-(trans-4-butylcyclohexyl)phenyl]benzene
Trifluoromethoxy-4-[4-(trans-4-hexylcyclohexyl)phenyl]benzene
Trifluoromethoxy-4-[4-(trans-4-heptylcyclohexyl)phenyl]benzene
Trifluoromethoxy-4-[4-(trans-4-octylcyclohexyl)phenyl]benzene
Trifluoromethoxy-4-[4-(trans-4-nonylcyclohexyl)phenyl]benzene
Trifluoromethoxy-4-[4-(trans-4-decylcyclohexyl)phenyl]benzene
Trifluoromethoxy-2-fluoro-4-[4-(trans-4-ethylcyclohexyl)phenyl]benzene
Trifluoromethoxy-2-fluoro-4-[4-(trans-4-propylcyclohexyl)phenyl]benzene
Trifluoromethoxy-2-fluoro-4-[4-(trans-4-butylcyclohexyl)phenyl]benzene
Trifluoromethoxy-2-fluoro-4-[4-(trans-4-pentylcyclohexyl)phenyl]benzene
Trifluoromethoxy-2-fluoro-4-[4-(trans-4-hexylcyclohexyl)phenyl]benzene
Trifluoromethoxy-2-fluoro-4-[4-(trans-4-heptylcyclohexyl)phenyl]benzene
Trifluoromethoxy-2-fluoro-4-[4-(trans-4-octylcyclohexyl)phenyl]benzene
Trifluoromethoxy-2-fluoro-4-[4-(trans-4-nonylcyclohexyl)phenyl]benzene
Trifluoromethoxy-2-fluoro-4-[4-(trans-4-decylcyclohexyl)phenyl]benzene.

Example 8

Analogously to Example 7, from 4-bromo-4'-pentylbiphenyl and trifluoromethoxy-4-bromobenzene, the corresponding trifluoromethoxy-4-(4'-pentylbiphenyl-4-yl)benzene is obtained.

The following are prepared analogously:
Trifluoromethoxy-4-(4-ethylbiphenyl-4-yl)benzene
Trifluoromethoxy-4-(4-propylbiphenyl-4-yl)benzene
Trifluoromethoxy-4-(4-butylbiphenyl-4-yl)benzene
Trifluoromethoxy-4-(4-hexylbiphenyl-4-yl)benzene
Trifluoromethoxy-4-(4-heptylbiphenyl-4-yl)benzene
Trifluoromethoxy-4-(4-octylbiphenyl-4-yl)benzene
Trifluoromethoxy-2-fluoro-4-(4'-ethylbiphenyl-4-yl)benzene
Trifluoromethoxy-2-fluoro-4-(4'-propylbiphenyl-4-yl)benzene
Trifluoromethoxy-2-fluoro-4-(4'-butylbiphenyl-4-yl)benzene
Trifluoromethoxy-2-fluoro-4-(4'-pentylbiphenyl-4-yl)-benzene
Trifluoromethoxy-2-fluoro-4-(4'-hexylbiphenyl-4-yl)benzene
Trifluoromethoxy-2-fluoro-4-(4'-heptylbiphenyl-4-yl)benzene
Trifluoromethoxy-2-fluoro-4-(4'-octylbiphenyl-4-yl)benzene
Trifluoromethoxy-4-(2',3'-difluoro-4'-ethoxybiphenyl-4yl)-benzene
Trifluoromethoxy-4-(2',3'-difluoro-4'-propoxybiphenyl-4-yl)-benzene
Trifluoromethoxy-4-(2',3'-difluoro-4'-butoxybiphenyl-4-yl)-benzene
Trifluoromethoxy-4-(2',3'-difluoro-4'-pentyloxybiphenyl-4-yl)-benzene
Trifluoromethoxy-4-(2',3'-difluoro-4'-hexyloxybiphenyl-4-yl)-benzene
Trifluoromethoxy-4-(2',3'-difluoro-4'-ethylbiphenyl-4-yl)-benzene
Trifluoromethoxy-4-(2',3'-difluoro-4'-propylbiphenyl-4-yl)-benzene
Trifluoromethoxy-4-(2',3'-difluoro-4'-butylbiphenyl-4-yl)-benzene
Trifluoromethoxy-4-(2',3'-difluoro-4'-pentylbiphenyl-4-yl)-benzene
Trifluoromethoxy-4-(2',3'-difluoro-4'-hexylbiphenyl-4-yl)-benzene
Trifluoromethoxy-4-(2',3'-difluoro-4'-heptylbiphenyl-4-yl)-benzene

Example 9

37 ml of butyllithium (15% in hexane) are added at −75° to a mixture of 12 g of 2-ethoxy-5-bromopyridine and 50 ml of THF, and the mixture is stirred for a further 1hour. 7.5 g of $ZnBr_2$ in 25 ml of THF are subsequently added at −70° to −65°, and the mixture is again stirred for 1 hour. 14.5 g of trifluoromethoxy-4-bromobenzene in 25 ml of THF and 1 g of PdCl$_2$ (dppf) are then added. The temperature is allowed to rise to room temperature, and the mixture is then stirred for 16 hours. Work-up is effected analogously to Example 7, and 2-ethoxy-5-(4 -trifluoromethoxyphenyl)pyridine having C 36° S$_A$ ((33°)I is obtained after purification by chromatography and/or crystallization.

The following are prepared analogously:
2-Methoxy-5-(4-trifluoromethoxyphenyl)pyridine
2-Propoxy-5-(4-trifluoromethoxyphenyl)pyridine
2-Butoxy-5-(4-trifluoromethoxyphenyl)pyridine
2-Pentyloxy-5-(4-trifluoromethoxyphenyl)pyridine
2-Hexyloxy-5-(4-trifluoromethoxyphenyl)pyridine
2-Heptyloxy-5-(4-trifluoromethoxyphenyl)pyridine
2-Octyloxy-5-(4-trifluoromethoxyphenyl)pyridine
2-Methyl-5-(4-trifluoromethoxyphenyl)pyridine
2-Ethyl-5-(4-trifluoromethoxyphenyl)pyridine
2-Propyl-5-(4-trifluoromethoxyphenyl)pyridine
2-Butyl-5-(4-trifluoromethoxyphenyl)pyridine
2-Pentyl-5-(4-trifluoromethoxyphenyl)pyridine
2-Hexyl-5-(4-trifluoromethoxyphenyl)pyridine
2-Heptyl-5-(4-trifluoromethoxyphenyl)pyridine
2-Octyl-5-(4-trifluoromethoxyphenyl)pyridine

Example 10

Analogously to Example 9, by reacting 14.0 g of 2-(4-bromophenyl)-5-propylpyrimidine and 12.1 g of trifluoromethoxy-4-bromobenzene, the corresponding 2-(4'-trifluoromethoxybiphenyl-4-yl )-5-propylpyrimidine having C 125° S$_G$ 1110 S$_A$ 218° I is obtained.

The following are prepared analogously:
2-(4'-Trifluoromethoxybiphenyl-4-yl)-5-methylpyrimidine
2-(4'-Trifluoromethoxybiphenyl-4-yl)-5-ethylpyrimidine
2-(4'-Trifluoromethoxybiphenyl-4-yl)-5-butylpyrimidine
2-(4'-Trifluoromethoxybiphenyl-4-yl)-5-pentylpyrimidine
2-(4'-Trifluoromethoxybiphenyl-4-yl)-5-hexylpyrimidine
2-(4'-Trifluoromethoxybiphenyl-4-yl)-5-heptylpyrimidine
2-(4'-Trifluoromethoxybiphenyl-4-yl)-5-octylpyrimidine
2-(4'-Trifluoromethoxybiphenyl-4-yl)-5-methoxypyrimidine
2-(4'-Trifluoromethoxybiphenyl-4-yl)-5-ethoxypyrimidine
2-(4'-Trifluoromethoxybiphenyl-4-yl)-5-propoxypyrimidine
2-(4'-Trifluoromethoxybiphenyl-4-yl)-5-butoxypyrimidine
2-(4'-Trifluoromethoxybiphenyl-4-yl)-5-pentyloxypyrimidine
2-(4'-Trifluoromethoxybiphenyl-4-yl)-5-hexyloxypyrimidine
2-(4'-Trifluoromethoxybiphenyl-4-yl)-5-heptyloxypyrimidine
2-(4'-Trifluoromethoxybiphenyl-4-yl)-5-octyloxypyrimidine.

Example 11 a) A mixture of 2.8 g of 4-(5-heptylpyrimidin-2-yl)styrene, 3.7 g of trifluoromethoxy-4-bromobenzene, 1.4 ml of triethylamine, 25 ml of acetonitrile, 50 m g of Pd(II) acetate and 125 mg of tri-o-tolylphosphine is refluxed for 36 hours. After cooling, the mixture is evaporated and, after purification by chromatography, 1-(4-trifluoromethoxyphenyl)-2-[4-(5-heptylpyrimidin-2-yl)phenyl]ethene having C 123° S$_C$ 151° S$_A$ 242° I is obtained.

b) This vinyl compound is hydrogenated at room temperature and atmospheric pressure in THF using Pd (5% on C). After work-up and purification by chromatography and/or crystallization, 1-(4-trifluoromethoxyphenyl)-2-[4-( 5-heptylpyrimidin-2-yl)phenyl]ethane having C 63° S$_B$ 98° S$_A$ 144° I is obtained.

The following are prepared analogously:
1-(4-Trifluoromethoxyphenyl)-2-[4-(5-ethylpyrimidin-2-yl)phenyl]ethane
1-(4-Trifluoromethoxyphenyl)-2-[4-(5-propylpyrimidin-2-yl)phenyl]ethane
1-(4-Trifluoromethoxyphenyl)-2-[4-(5-butylpyrimidin-2-yl)phenyl]ethane
1-(4-Trifluoromethoxyphenyl)-2-[4-(5-pentylpyrimidin-2-yl)phenyl]ethane
1-(4-Trifluoromethoxyphenyl)-2-[4-(5-hexylpyrimidin-2-yl)phenyl]ethane
1-(4-Trifluoromethoxyphenyl)-2-[4-(5-octylpyrimidin-2-yl)phenyl]ethane
1-(4-Trifluoromethoxyphenyl)-2-[4-(5-ethoxypyrimidin-2-yl)phenyl]ethane
1-(4-Trifluoromethoxyphenyl)-2-[4-(5-propoxypyrimidin-2-yl)phenyl]ethane
1-(4-Trifluoromethoxyphenyl)-2-[4-(5-butoxypyrimidin-2-yl)phenyl] ethane
1-(4-Trifluoromethoxyphenyl)-2-[4-(5-pentyloxypyrimidin-2-yl)phenyl]ethane
1-(4-Trifluoromethoxyphenyl)-2-[4-(5-hexyloxypyrimidin-2-yl)phenyl]ethane
1-(4-Trifluoromethoxyphenyl)-2-[4-(5-heptyloxypyrimidin-2-yl)phenyl]ethane
1-(4-Trifluoromethoxyphenyl)-2-[4-(5-octyloxypyrimidin-2-yl)phenyl]ethane

Example 12 a) A mixture of 25.7 g of 4-(trans-4-pentylcyclohexyl)styrene, 14.5 g of 4-(trifluoromethoxy)-iodobenzene, 100 ml of acetonitrile, 7 ml of triethylamine, 0.23 g or Pd(II) acetate and 0.6 g of tri-o-tolylphosphine is heated at the boiling point for 24 hours. After cooling to 0°, filtering off the precipitated substance with suction, and washing with acetonitrile and water, 1-(4-trifluoromethoxyphenyl)-2-[4-(trans-4-pentylcyclohexyl)phenyl]-ethene having C 72° S$_B$ 168° S$_A$ 194° N 224.1° I, is obtained after purification by crystallization from ethanol/ethyl acetate.

b) The ethene derivative from a) is hydrogenated in THF using Pd/C at room temperature and atmospheric pressure. After work-up and purification by crystallization, 1-(4-trifluoromethoxyphenyl)-2-[4-(trans-4-pentylcyclohexyl)phenyl]-ethane is obtained.

The following are prepared analogously:
1-(4- Trifluoromethoxyphenyl)-2-[4-(trans-4-methylcyclohexyl)phenyl]-ethane
1-(4-Trifluoromethoxyphenyl)-2-[4-(trans-4-ethylcyclohexyl)phenyl]-ethane
1-(4-Trifluoromethoxyphenyl)-2-[4-(trans-4-propylcyclohexyl)phenyl]-ethane
1-(4-Trifluoromethoxyphenyl)-2-[4-(trans-4-butylcyclohexyl)phenyl]-ethane
1-(4-Trifluoromethoxyphenyl)-2-[4-(trans-4-pentylcyclohexyl)phenyl]-ethane
1-(4-Trifluoromethoxyphenyl)-2-[4-(trans-4-hexylcyclohexyl)phenyl] -ethane
1-(4-Trifluoromethoxyphenyl)-2-[4-(trans-4-heptylcyclohexyl)phenyl]-ethane

Example 13

A Grignard compound is prepared from 1.2 g of magnesium, 50 ml of THF and 11.4 g of 4-pentyl-bromobenzene in 25 ml of THF. When the addition is complete, the mixture is refluxed for a further 1 hour and cooled to 10° and 14 g of 4-trifluoromethoxy-bromobenzene in 25 ml of THF and 0.73 g of PdCl$_2$ (dppf) are added. The cooling is removed, but the reaction mixture should not climb above 20°. The mixture is subsequently stirred at room temperature for 16 hours, poured into 100 ml of saturated NH$_4$Cl solution and stirred for a further 15 minutes, and the organic phase is then worked up. After purification by crystallization, trifluoromethoxy-4-(4-pentylphenyl)benzene having C 67° I is obtained.

The following are prepared analogously:
Trifluoromethoxy-4-(4-methylphenyl)benzene
Trifluoromethoxy-4-(4-ethylphenyl)benzene
Trifluoromethoxy-4-(4-propylphenyl)benzene
Trifluoromethoxy-4-(4-butylphenyl)benzene
Trifluoromethoxy-4-(4-hexylphenyl)benzene
Trifluoromethoxy-4-(4-heptylphenyl)benzene
Trifluoromethoxy-4-(2,3-difluoro-4-methylphenyl)benzene
Trifluoromethoxy-4-(2,3-difluoro-4-ethylphenyl)benzene
Trifluoromethoxy-4-(2,3-difluoro-4-propylphenyl)benzene
Trifluoromethoxy-4-(2,3-difluoro-4-butylphenyl)benzene
Trifluoromethoxy-4-(2,3-difluoro-4-pentylphenyl)benzene
Trifluoromethoxy-4-(2,3-difluoro-4-ethoxyphenyl)benzene
Trifluoromethoxy-4-(2,3-difluoro-4-methoxyphenyl)benzene
Trifluoromethoxy-4-(2,3-difluoro-4-propoxyphenyl)benzene
Trifluoromethoxy-4-(2,3-difluoro-4-butoxyphenyl)benzene
Trifluoromethoxy-4-(2,3-difluoro-4-pentyloxyphenyl)benzene

Example 14

By reacting 7.5 g of 4-ethoxystyrene with 14.4 g of 4-trifluoromethoxyiodobenzene, 6.9 ml of triethylamine, 0.23 g of Pd(II) acetate and 0.6 g of tri-o-tolylphosphine in 75 ml of acetonitrile, 1-(4-trifluoromethoxyphenyl)- 2-(4-ethoxyphenyl)-ethene is obtained analogously to Example 12a).

The following are prepared analogously:
1-(4-Trifluoromethoxyphenyl)-2-(4-methoxyphenyl)-ethene
1-(4-Trifluoromethoxyphenyl)-2-(4-propoxyphenyl)-ethene
1-(4-Trifluoromethoxyphenyl)-2-(4-butoxyphenyl)-ethene
1-(4-Trifluoromethoxyphenyl)-2-(4-pentyloxyphenyl)-ethene
1-(4-Trifluoromethoxyphenyl)-2-(4-hexyloxyphenyl)-ethene
1-(4-Trifluoromethoxyphenyl)-2-(4-heptyloxyphenyl)-ethene
1-(4-Trifluoromethoxyphenyl)-2-(4-methylphenyl)-ethene
1-(4-Trifluoromethoxyphenyl)-2-(4-ethylphenyl)-ethene
1-(4-Trifluoromethoxyphenyl)-2-(4-propylphenyl)-ethene
1-(4-Trifluoromethoxyphenyl)-2-(4-butylphenyl)-ethene
1-(4-Trifluoromethoxyphenyl)-2-(4-pentylphenyl)-ethene
1-(4-Trifluoromethoxyphenyl)-2-(4-hexylphenyl)-ethene
1-(4-Trifluoromethoxyphenyl)-2-(4-heptylphenyl)-ethene
1-(4-Trifluoromethoxyphenyl)-2-(4-octylphenyl)-ethene

Example 15

By hydrogenation of the ethene derivatives, prepared in Example 14, using Pd/C in THF, the corresponding ethane derivatives are obtained:
1-(4-Trifluoromethoxyphenyl)-2-(4-ethoxyphenyl)-ethane
1-(4-Trifluoromethoxyphenyl)-2-(4-methoxyphenyl)-ethane
1-(4-Trifluoromethoxyphenyl)-2-(4-propoxyphenyl)-ethane
1-(4-Trifluoromethoxyphenyl)-2-(4-butoxyphenyl)-ethane
1-(4-Trifluoromethoxyphenyl)-2-(4-pentyloxyphenyl)-ethane
1-(4-Trifluoromethoxyphenyl)-2-(4-hexyloxyphenyl)-ethane
1-(4-Trifluoromethoxyphenyl)-2-(4-heptyloxyphenyl)-ethane
1-(4-Trifluoromethoxyphenyl)-2-(4-methylphenyl)-ethane
1-(4-Trifluoromethoxyphenyl)-2-(4-ethylphenyl)-ethane
1-(4-Trifluoromethoxyphenyl)-2-(4-propylphenyl)-ethane
1-(4-Trifluoromethoxyphenyl)-2-(4-butylphenyl)-ethane
1-(4-Trifluoromethoxyphenyl)-2-(4-pentylphenyl)-ethane
1-(4-Trifluoromethoxyphenyl)-2-(4-hexylphenyl)-ethane
1-(4-Trifluoromethoxyphenyl)-2-(4-heptylphenyl)-ethane
1-(4-Trifluoromethoxyphenyl)-2-(4-octylphenyl)-ethane
1-(4-Trifluoromethoxyphenyl)-2-(2,3-difluoro-4-ethoxyphenyl)-ethane
1-(4-Trifluoromethoxyphenyl)-2-(2,3-difluoro-4-propoxyphenyl)-ethane
1-(4-Trifluoromethoxyphenyl)-2-(2,3-difluoro-4-butoxyphenyl)-ethane
1-(4-Trifluoromethoxyphenyl)-2-(2,3-difluoro-4-pentyloxyphenyl)-ethane
1-(4-Trifluoromethoxyphenyl)-2-(2,3-difluoro-4-ethylphenyl)-ethane
1-(4-Trifluoromethoxyphenyl)-2-(2,3-difluoro-4-propylphenyl)-ethane
1-(4-Trifluoromethoxyphenyl)-2-(2,3-difluoro-4-butylphenyl)-ethane
1-(4-Trifluoromethoxyphenyl)-2-(2,3-difluoro-4-pentylphenyl)-ethane

Example 16

0.7 g of lithium and 5.7 g of ZnBr$_2$ are added at 0° to a mixture of 15.4 g of trans-4-pentylcyclohexylethyliodide and 100 ml of THF/toluene (1:4), and the reaction mixture is treated with ultrasound at 0°–10° for 4 hours. 14.8 g of 4-trifluoromethoxybromobenzene and 0.88 g of PdCl$_2$ (dppf) are subsequently added at 5°. The mixture is allowed to warm to room temperature and is stirred for a further 16 hours. The mixture is then poured into 100 ml of saturated NH$_4$Cl solution, and the organic phase is worked up. After purification by chromatography and/or crystallization, 1-(4-trifluoromethoxyphenyl)-2-(trans- 4-pentylcyclohexyl)-ethane is obtained.

The following are prepared analogously:
1-(4-Trifluoromethoxyphenyl)-2-(trans-4-ethylcyclohexyl)ethane
1-(4-Trifluoromethoxyphenyl)-2-(trans-4-propylcyclohexyl)ethane
1-(4-Trifluoromethoxyphenyl)-2-(trans-4-butylcyclohexyl)ethane
1-(4-Trifluoromethoxyphenyl)-2-(trans-4-hexylcyclohexyl)ethane
1-(4-Trifluoromethoxyphenyl)-2-(trans-4-heptylcyclohexyl)ethane

Example 17

Trifluoromethoxy-4-(trans-4-propylcyclohexyl)benzene is obtained analogously to Example 16 from 15.4 g of trans-4-propylcyclohexyl bromide and 18.2 g of 4-trifluoromethoxybromobenzene after purification by chromatography and/or vacuum distillation.

The following are prepared analogously:
Trifluoromethoxy-4-(trans-4-ethylcyclohexyl)benzene
Trifluoromethoxy-4-(trans-4-butylcyclohexyl)benzene Trifluoromethoxy-4-(trans-4-pentylcyclohexyl)benzene
Trifluoromethoxy-4-(trans-4-hexylcyclohexyl)benzene
Trifluoromethoxy-4-(trans-4-heptylcyclohexyl)benzene
Trifluoromethoxy-4-(trans-4-octylcyclohexyl)benzene Example 18

First, 4.6 g of dicyclohexylcarbodiimide in 80 ml of toluene are added to a mixture of 4 g of 4-trifluoromethoxyphenol and 20 ml of toluene, 0.2 g of dimethylaminopyridine is then added, the mixture is stirred at room temperature for 1 hour, and 3.8 g of trans-4-ethylcyclohexanecarboxylic acid are then added. After work-up and purification by chromatography and/or crystallization, 4-(trifluoromethoxy)phenyl trans-4-ethylcyclohexanecarboxylate is obtained.

The following are prepared analogously:
4-(Trifluoromethoxy)phenyl trans-4-propylcyclohexanecarboxylate
4-(Trifluoromethoxy)phenyl trans-4-butylcyclohexanecarboxylate
4-(Trifluoromethoxy)phenyl trans-4-pentylcyclohexanecarboxylate
4-(Trifluoromethoxy)phenyl trans-4-hexylcyclohexanecarboxylate
4-(Trifluoromethoxy)phenyl trans-4-heptylcyclohexancarboxylate
4-(Trifluoromethoxy)phenyl trans-4-(trans-4-propylcyclohexyl)cyclohexanecarboxylate
4-(Trifluoromethoxy)phenyl trans-4-(trans-4-ethylcyclohexyl)cyclohexanecarboxylate
4-(Trifluoromethoxy)phenyl trans-4-(trans-4-butylcyclohexyl)cyclohexanecarboxylate
4-(Trifluoromethoxy)phenyl trans-4-(trans-4-pentylcyclohexyl)cyclohexanecarboxylate
4-(Trifluoromethoxy)phenyl trans-4-(trans-4-hexylcyclohexyl)cyclohexanecarboxylate
4-(Trifluoromethoxy)phenyl trans-4-(trans-4-heptylcyclohexyl)cyclohexanecarboxylate Example 19

10.0 g of dicyclohexylcarbodiimide in 20 ml of toluene are added with water cooling to a mixture of 9.1 g of 4-trifluoromethoxybenzoic acid, 6.0 g of 4-propylphenol, 2.7 g of dimethylaminopyridine and 30 ml of toluene. The mixture is stirred for 2 hours, 1 g of oxalic acid is added, and the mixture is stirred for a further hour and filtered with suction. The filtrate is washed by shaking with 1M HCl, the phases are separated, and the organic phase is washed by shaking with 1M NaOH and worked up. After purification by chromatography and/or crystallization, 4-propylphenyl 4-(trifluoromethoxy)-benzoate having C 59° I is obtained.

The following are prepared analogously:
4-Ethylphenyl 4-(trifluoromethoxy)benzoate
4-Butylphenyl 4-(trifluoromethoxy)benzoate
4-Pentylphenyl 4-(trifluoromethoxy)benzoate
4-Hexylphenyl 4-(trifluoromethoxy)benzoate
4-Heptylphenyl 4-(trifluoromethoxy)benzoate
4-Octylphenyl 4-(trifluoromethoxy)benzoate The examples below concern liquid-crystalline phases according to the invention:

Example A

A liquid-crystalline phase, comprising
16% of p-trans-4-propylcyclohexylbenzonitrile,
4% of p-trans-4-pentylcyclohexylbenzonitrile,
9% of trifluoromethoxy-4-(5-propyl-1,3-dioxan-2-yl)benzene,
9% of trifluoromethoxy-4-(5-pentyl-1,3-dioxan-2-yl)benzene,
20% of trans-1-p-methoxyphenyl-4-propylcyclohexane,
11% of 4-ethyl-4'-(trans-4-propylcyclohexyl)biphenyl,
11% of 4-ethyl-4'-(trans-4-pentylcyclohexyl)biphenyl,
4% of 4,4'-bis-(trans-4-propylcyclohexyl)biphenyl,
6% of 4-(trans-4-pentylcyclohexyl)-4'-(trans-4-propylcyclohexyl)biphenyl,
3% of 4-(trans-4-propylcyclohexyl)-2'-fluoro-4'-(trans-4-propylcyclohexyl)biphenyl,
4% of 2-fluoro-4-(trans-4-pentylcyclohexyl)-4'-(trans-4-propylcyclohexyl)biphenyl and
3% of 4-(trans-4-pentylcyclohexyl)-2'-fluoro-4'-(trans-4-pentylcyclohexyl)biphenyl,
has a melting point of −17°, a clear point of 92° and a viscosity of 21 mm$^2$/s at 20°.

Example B

A liquid-crystalline phase, comprising
8% of p-trans-4-propylcyclohexylbenzonitrile
12% of trifluoromethoxy-4-(5-propyl-1,3-dioxan-2-yl)benzene
10% of p-trans-4-butylcyclohexylbenzonitrile,
12% of trans-1-p-ethylphenyl-4-propylcyclohexane
6% of trans-1-p-methoxyphenyl-4-propylcyclohexane,
13% of 4-ethyl-4'-(trans-4-propylcyclohexyl)biphenyl,
12% of 4-ethyl-4'-(trans-4-pentylcyclohexyl)biphenyl,
3% of 4,4'-bis-(trans-4-propylcyclohexyl)biphenyl,
6% of 4-(trans-4-pentylcyclohexyl)-4'-(trans-4-propylcyclohexyl)biphenyl,
3% of 4,4'-bis-(trans-4-pentylcyclohexyl)biphenyl,
4% of 4-(trans-4-pentylcyclohexyl)-4'-(trans-4-propylcyclohexyl)biphenyl,
7% of 2-fluoro-4-(trans-4-pentylcyclohexyl)-4'-(trans-4-propylcyclohexyl)biphenyl, and
4% of 4-(trans-4-pentylcyclohexyl)-2'-fluoro-4'-(trans-4-pentylcyclohexyl)biphenyl,
has a melting point of −20.8°, clear point of 108° and viscosity of 25 mm$^2$/s at 20°.

Example C

A liquid-crystalline phase, comprising
7% of 2-p-cyanophenyl-5-propyl-1,3-dioxane,
6% of 2-p-cyanophenyl-5-butyl-1,3-dioxane,
4% of 2-p-cyanophenyl-5-pentyl-1,3-dioxane,
9% of trifluoromethoxy-4-(5-propyl-1,3-dioxan-2-yl)benzene
9% of trifluoromethoxy-4-(5-pentyl-1,3-dioxan-2-yl) benzene,
12% of 4-ethyl-4'-(trans-4-propylcyclohexyl)biphenyl,
10% of 4-ethyl-4'-(trans-4-pentylcyclohexyl)biphenyl,
5% of 2-p-pentyloxyphenyl-5-hexylpyrimidine,
5% of 2-p-hexyloxyphenyl-5-hexylpyrimidine,
5% of 2-p-heptyloxyphenyl-5-hexylpyrimidine,
4% of 2-p-propoxyphenyl-5-hexylpyrimidine,
4% of 2-p-heptyloxyphenyl-5-heptylpyrimidine,
4% of 2-p-nonyloxyphenyl-5-heptylpyrimidine,
7% of 2-fluoro-4-(trans-4-pentylcyclohexyl)-4'-(trans-4-propylcyclohexyl)biphenyl, and
9% of trans-1-p-methoxyphenyl-4-propylcyclohexane,
has C-17° Sm 30° N 70° I.

Example D

A liquid-crystalline phase comprising
20% of 1-(4-trifluoromethoxyphenyl)-2-[trans-4-(trans-4-propylcyclohexyl)cyclohexyl]-ethane
20% of 1-(4-trifluoromethoxyphenyl)-2-[trans-4-(trans-4-pentylcyclohexyl)cyctohexyl]-ethane
20% of trans-1-p-methoxyphenyl-4-propylcyclohexane,
20% of trans-1-p-ethoxyphenyl-4-propylcyclohexane and
20% of trans-1-p-butoxyphenyl-4-propylcyclohexane
has a melting point of −6.2°, a clear point of 64° and a viscosity of 12 mm$^2$/s at 20°.

Example E

A liquid-crystalline phase comprising
20% of p-trans-4-propylcyclohexyl-benzonitrile,
20% of trans-1-p-propylphenyl-4-pentylcyclohexane,
15% of trans-1-p-ethoxyphenyl-4-propylcyclohexane,
15% of trans-1-p-butoxyphenyl-4-propylcyclohexane,
15% of 4-trifluoromethoxy-4'-(trans-4-propylcyclohexyl)biphenyl and
15% of 4-trifluoromethoxy-4'-(trans-4-pentylcyclohexyl)biphenyl
has a clear point of 62°, a viscosity of 12 mm$^2$/s at 20° and Δn=+0.12.

Example F

A liquid-crystalline phase comprising
10% of p-trans-4-propylcyclohexyl-benzonitrile,
10% of 2-p-cyanophenyl-5-propyl-1,3-dioxane,
10% of 4-propyl-4'-cyanobiphenyl,
10% of p-cyanophenyl 4-propylbenzoate,
10% of 3-fluoro-4-cyanophenyl 4-propylbenzoate
10% of trans-1-p-methoxyphenyl-4-propylcyclohexane,
10% of trans-1-p-ethoxyphenyl-4-propylcyclohexane,
15% of 4-ethyl-1-trans-4-(trans-4-propylcyclohexyl)cyclohexyl-benzene and
15% of 4-trifluoromethoxy-1-trans-4-(trans-4-propylcyclohexyl)cyclohexyl-benzene
has a clear point of 66°, a viscosity of 22 mm$^2$/s and Δn=+0.14.

Example G

A liquid-crystalline phase comprising
7% of 2-p-cyanophenyl-5-propyl-1,3-dioxane,
6of 2-p-cyanophenyl-5-butyl-1,3-dioxane,
4% of 2-p-cyanophenyl-5-pentyl-1,3-dioxane,
9% of 1-(4-trifluoromethoxyphenyl)-2-[trans-4-(trans-4-propylcyclohexyl)cyclohexyl]-ethane,
9% of 1-(4-trifluoromethoxyphenyl-2-[trans-4-(trans-4-pentylcyclohexyl)cyclohexyl]-ethane,
12% of 4-ethyl-4'-(trans-4-propylcyclohexyl)-biphenyl,
10% of 4-ethyl-4'-(trans-4-pentylcyclohexyl)-biphenyl,
5% of 2-p-pentyloxyphenyl-5-hexylpyrimidine,
5% of 2-p-hexyloxyphenyl-5-hexylpyrimidine,
5% of 2-p-heptyloxyphenyl-5-hexylpyrimidine,
4% of 2-p-propoxyphenyl-5-hexylpyrimidine,
4% of 2-p-heptyloxyphenyl-5-heptylpyrimidine,
4% of 2-p-nonyloxyphenyl-5-heptylpyrimidine,
7% of 2-fluoro-4-(trans-4-pentylcyclohexyl)-4'-(trans-4-propylcyclohexyl)-biphenyl and
9% of trans-1-p-methoxyphenyl-4-propylcyclohexane
has a melting point of −17°, a clear point of 99° and a viscosity of 32 mm$^2$/s at 20°.

Example H

A liquid-crystalline phase comprising
8% of p-trans-4-propylcyclohexyl-benzonitrile,
12% of 1-(4-trifluoromethoxyphenyl)-2-[trans-4-trans-4-propylcyclohexyl)cyclohexyl]-ethane,
10% of p-trans-4-butylcyclohexyl-benzonitrile,
12% of trans-1-p-ethylphenyl-4-propylcyclohexane,
6% of trans-1-p-methoxyphenyl-4-propylcyclohexane,
13% of 4-ethyl-4'-(trans-4-propylcyclohexyl)-biphenyl,
12% of 4-ethyl-4'-(trans-4-pentylcyclohexyl)-biphenyl
3% of 4,4'-bis-(trans-4-propylcyclohexyl)-biphenyl,
6% of 4-(trans-4-pentylcyclohexyl)-4'-(trans-4-propylcyclohexyl)-biphenyl,
3% of 4,4'-bis-(trans-4-pentylcyclohexyl)-biphenyl,
4% of 4-(trans-4-pentylcyclohexyl)-4'-(trans-4-propylcyclohexyl)-biphenyl,
7% of 2-fluoro-4-(trans-4-pentylcyclohexyl)-4'-(trans-4-propylcyclohexyl)-biphenyl and
4% of 4-(trans-4-pentylcyclohexyl)-2'-fluoro-4'-(trans-4-pentylcyclohexyl)-biphenyl
has a melting point of −21°, a clear point of 123° and a viscosity of 27 mm$^2$/s at 20°.

Example I

A liquid-crystalline phase comprising
16% of p-trans-4-propylcyclohexyl-benzonitrile,
4% of p-trans-4-pentylcyclohexyl-benzonitrile,
9% of 1-(4-trifluoromethoxyphenyl)-2-[trans-4-(trans-4-propylcyclohexyl)cyclohexyl]-ethane
9% of 1-(4-trifluoromethoxyphenyl)-2-[trans-4-(trans-4-pentylcyclohexyl)cyclohexyl]-ethane,
20% of trans-1-p-methoxyphenyl-4-propylcyclohexane,
11% of 4-ethyl-4'-(trans-4-propylcyclohexyl)-biphenyl,
11% of 4-ethyl-4'-(trans-4-pentylcyclohexyl)-biphenyl,
4% of 4,4'-bis-(trans-4-propylcyclohexyl)-biphenyl,
6% of 4-(trans-4-pentylcyclohexyl)-4'-(trans-4-propylcyclohexyl)-biphenyl,
3% of 4-(trans-4-propylcyclohexyl)-2'-fluoro-4'-(trans-4-propylcyclohexyl)-biphenyl,
4% of 2-fluoro-4-(trans-4-pentylcyclohexyl)-4'-(trans-4-propylcyclohexyl)-biphenyl and
3% of 4-(trans-4-pentylcyclohexyl)-2'-fluoro-4'-(trans-4-pentylcyclohexyl)-biphenyl
has a melting point of −15°, a clear point of 120° and a viscosity 23 mm$^2$/s at 20°.

Example 1a

4-Difluoromethoxy-4'-octoxy-biphenyl

A mixture of 20 g of 4-hydroxy-4'-octyloxybiphenyl, 13.6 g of NaOH, 100 ml of water and 150 ml of dioxane is heated to 70° C. with stirring. 10 g of chlorodifluoromethane are passed into the cooled two-phase mixture with vigorous stirring. The reaction mixture is poured into water, and the product is extracted with petroleum ether. The organic phase is dried over Na$_2$SO$_4$, evaporated, and the residue is filtered through a short silica gel column using petroleum ether as eluent. The product is recrystallized from acetonitrile. Colorless crystals are obtained. m.p.: 104° C., c.p.: 20° C. (extrapolated), Δn=0.093, viscosity: 17.

The following were prepared analogously:
4-difluoromethoxy-4'-methoxy-biphenyl
4-difluoromethoxy-4'-ethoxy-biphenyl
4-difluoromethoxy-4'-propoxy-biphenyl
4-difluoromethoxy-4'-butoxy-biphenyl, m.p.: 122° C., Δn=0.146

4-difluoromethoxy-4'-pentoxy-biphenyl
4-difluoromethoxy-4'-hexoxy-biphenyl
4-difluoromethoxy-4'-heptoxy-biphenyl
4-difluoromethoxy-4'-nonoxy-biphenyl
4-difluoromethoxy-4'-decoxy-biphenyl
4-difluoromethoxy-4'-methyl-biphenyl
4-difluoromethoxy-4'-ethyl-biphenyl
1-(4-difluoromethoxyphenyl)-4-ethyl-bicyclo[2.2.2]octane
4-difluoromethoxy-4'-propyl-biphenyl, m.p.: 84° C., c.p. (extrapolated): −30° C. viscosity: 6
4-difluoromethoxy-4'-butyl-biphenyl
4-difluoromethoxy-4'-pentyl-biphenyl
4-difluoromethoxy-4'-hexyl-biphenyl
4-difluoromethoxy-4'-heptyl-biphenyl
4-difluoromethoxy-4'-nonyl-biphenyl
4-difluoromethoxy-4'-decyl-biphenyl
1-propyl-3-(4-difluoromethoxyphenyl-4'-yl)-cyclobutane
6-(4-difluoromethoxyphenyl)-2-methyl-naphthalene
6-(4-difluoromethoxyphenyl)-2-methyl-1,2,3,4-tetrahydronaphthalene
difluoromethoxy-4-(trans-4-ethylcyclohexyl)-benzene
difluoromethoxy-4-(trans-4-propylcyclohexyl)-benzene m.p.: −15° C., c.p.: −40° C. (extrapolated), Δn=0.035, viscosity: 5;
difluoromethoxy-4-(trans-4-butylyclohexyl)-benzene (sic) m.p.: 8° C., c.p.: −30° C. (extrapolated), Δn=0.043, viscosity: 6;
difluoromethoxy-4-(trans-4-pentylcyclohexyl)-benzene m.p.: 1° C., c.p.: −17° C., Δn=0.058, viscosity: 7;
difluoromethoxy-4-(trans-4-hexylcyclohexyl)-benzene
difluoromethoxy-4-(trans-4-heptylcyclohexyl)-benzene
difluoromethoxy-4-(trans-4-octylcyclohexyl)-benzene
difluoromethoxy-4-(trans-4-nonylcyclohexyl)-benzene
difluoromethoxy-4-(trans-4-decylcyclohexyl)-benzene
4-difluoromethoxy-2',3'-difluoro-4'-methoxy-biphenyl
4-difluoromethoxy-2',3'-difluoro-4'-ethoxy-biphenyl
4-difluoromethoxy-2',3'-difluoro-4'-propoxy-biphenyl
4-difluoromethoxy-2',3'-difluoro-4'-butoxy-biphenyl
4-difluoromethoxy-2',3'-difluoro-4'-pentoxy-biphenyl
4-difluoromethoxy-2',3'-difluoro-4'-hexoxy-biphenyl
4-difluoromethoxy-2',3'-difluoro-4'-heptoxy-biphenyl
4-difluoromethoxy-2',3'-difluoro-4'-octoxy-biphenyl
4-difluoromethoxy-2',3'-difluoro-4'-nonoxy-biphenyl
4-difluoromethoxy-2',3'-difluoro-4'-decoxy-biphenyl
4-difluoromethoxy-2',3'-difluoro-4'-methyl-biphenyl
4-difluoromethoxy-2',3'-difluoro-4'-ethyl-biphenyl
4-difluoromethoxy-2',3'-difluoro-4'-propyl-biphenyl
4-difluoromethoxy-2',3'-difluoro-4'-butyl-biphenyl
4-difluoromethoxy-2',3'-difluoro-4'-pentyl-biphenyl
4-difluoromethoxy-2',3'-difluoro-4'-hexyl-biphenyl
4-difluoromethoxy-2',3'-difluoro-4'-heptyl-biphenyl
4-difluoromethoxy-2',3'-difluoro-4'-octyl-biphenyl
4-difluoromethoxy-2',3'-difluoro-4'-nonyl-biphenyl
4-difluoromethoxy-2',3'-difluoro-4'-decyl-biphenyl
4-difluoromethoxy-4'-cyano-3'-fluorobiphenyl
4-difluoromethoxy-4'-methyl-terphenyl
4-difluoromethoxy-4'-ethyl-terphenyl
4-difluoromethoxy-4'-propyl-terphenyl
4-difluoromethoxy-4'-butyl-terphenyl
4-difluoromethoxy-4'-pentyl-terphenyl, m.p.: 223° C., c.p.: 41° C.
4-difluoromethoxy-4'-hexyl-terphenyl
4-difluoromethoxy-4'-heptyl-terphenyl
4-difluoromethoxy-4'-octyl-terphenyl
4-difluoromethoxy-4'-nonyl-terphenyl
4-difluoromethoxy-4'-decyl-terphenyl
4-difluoromethoxy-4'-(trans-4-methylcyclohexyl)-biphenyl
4-difluoromethoxy-4'-(trans-4-ethylcyclohexyl)-biphenyl
4-difluoromethoxy-4'-(trans-4-propylcyclohexyl)-biphenyl, m.p.: 82° C., c.p.: 169.4° C., Δn=0.174
4-difluoromethoxy-4'-(trans-4-butylcyclohexyl)-biphenyl
4-difluoromethoxy-4'-(trans-4-pentylcyclohexyl)-biphenyl, m.p.: 67° C., c.p.: 161.8° C., Δn=0.115
4-difluoromethoxy-4'-(trans-4-hexylcyclohexyl)-biphenyl
4-difluoromethoxy-4'-(trans-4-heptylcyclohexyl)-biphenyl
4-difluoromethoxy-4'-(trans-4-octylcyclohexyl)-biphenyl
4-difluoromethoxy-4'-(trans-4-nonylcyclohexyl)-biphenyl
4-difluoromethoxy-4'-(trans-4-decylcyclohexyl)-biphenyl
4-methyl-4'-(4-difluoromethoxyphenyl)-trans,trans-bicyclohexyl
4-trifluoromethyl-4'-(4-difluoromethoxyphenyl)-trans,trans-bicyclohexyl
4-ethyl-4'-(4-difluoromethoxyphenyl)-trans,trans-bicyclohexyl
4-propyl-4'-(4-difluoromethoxyphenyl)-trans,trans-bicyclohexyl, m.p.: 39° C., c.p.: 148.6° C., Δn=0.088, viscosity: 16
4-isopropyl-4'-(4-difluoromethoxyphenyl)-trans,trans-bicyclohexyl
4-butyl-4'-(4-difluoromethoxyphenyl)-trans,trans-bicyclohexyl
4-methoxyethyl-4'-(4-difluoromethoxyphenyl)-trans,trans-bicyclohexyl
4-pentyl-4'-(4-difluoromethoxyphenyl)-trans,trans-bicyclohexyl
4-hexyl-4'-(4-difluoromethoxyphenyl)-trans,trans-bicyclohexyl
4-heptyl-4'-(4-difluoromethoxyphenyl)-trans,trans-bicyclohexyl
4-octyl-4'-(4-difluoromethoxyphenyl)-trans,trans-bicyclohexyl
4-nonyl-4'-(4-difluoromethoxyphenyl)-trans,trans-bicyclohexyl
4-decyl-4'-(4-difluoromethoxyphenyl)-trans,trans-bicyclohexyl
1-(4-difluoromethoxyphenyl)-4-(trans-4-methylcyclohexyl)-cyclohexene
1-(4-difluoromethoxyphenyl)-4-(trans-4-ethylcyclohexyl)-cyclohexene
1-(4-difluoromethoxyphenyl)-4-(trans-4-propylcyclohexyl)-cyclohexene
1-(4-difluoromethoxyphenyl)-4-(trans-4-butylcyclohexyl)-cyclohexene
1-(4-difluoromethoxyphenyl)-4-(trans-4-pentylcyclohexyl)-cyclohexene
1-(4-difluoromethoxyphenyl)-4-(trans-4-hexylcyclohexyl)-cyclohexene
1-(4-difluoromethoxyphenyl)-4-(trans-4-heptylcyclohexyl)-cyclohexene
1-(4-difluoromethoxyphenyl)-4-(trans-4-octylcyclohexyl)-cyclohexene
1-(4-difluoromethoxyphenyl)-4-(trans-4-nonylcyclohexyl)-cyclohexene
1-(4-difluoromethoxyphenyl)-4-(trans-4-decylcyclohexyl)-cyclohexene
1-(4-difluoromethoxyphenyl)-trans-4-(1-methylcyclohexen-4-yl)-cyclohexane
1-(4-difluoromethoxyphenyl)-trans-4-(1-ethylcyclohexen-4-yl)-cyclohexane
1-(4-difluoromethoxyphenyl)-trans-4-(1-propylcyclohexen-4-yl)-cyclohexane
1-(4-difluoromethoxyphenyl)-trans-4-(1-butylcyclohexen-4-yl)-cyclohexane
1-(4-difluoromethoxyphenyl)-trans-4-(1-pentylcyclohexen-4-yl)-cyclohexane 1-(4-difluoromethoxyphenyl)-trans-4-(1-hexylcyclohexen-4-yl)-cyclohexane
1-(4-difluoromethoxyphenyl)-trans-4-(1-heptylcyclohexen-4-yl)-cyclohexane
1-(4-difluoromethoxyphenyl)-trans-4-(1-octylcyclohexen-4-yl)-cyclohexane
1-(4-difluoromethoxyphenyl)-trans-4-(1-nonylcyclohexen-4-yl)-cyclohexane
1-(4-difluoromethoxyphenyl)-trans-4-(1-decylcyclohexen-4-yl)cyclohexane
4-methyl-4'-(3-fluoro-4-difluoromethoxyphenyl)-trans, trans-bicyclohexyl
4-ethyl-4'-(3-fluoro-4-difluoromethoxyphenyl)-trans,trans-bicyclohexyl
4-propyl-4'-(3,5-difluoro-4-difluoromethoxyphenyl)-trans, trans-bicyclohexyl
4-propyl-4'-(3-fluoro-4-difluoromethoxyphenyl)-trans, trans-bicyclohexyl, m.p.: 33° C., c.p.: 144° C., Δn=0.106
4-butyl-4'-(3-fluoro-4-difluoromethoxyphenyl)-trans,trans-bicyclohexyl
4-pentyl-4'-(3-fluoro-4-difluoromethoxyphenyl)-trans, trans-bicyclohexyl
4-hexyl-4'-(3-fluoro-4-difluoromethoxyphenyl)-trans,trans-bicyclohexyl
4-heptyl-4'-(3-fluoro-4-difluoromethoxyphenyl)-trans, trans-bicyclohexyl
4-octyl-4'-(3-fluoro-4-difluoromethoxyphenyl)-trans,trans-bicyclohexyl
4-nonyl-4'-(3-fluoro-4-difluoromethoxyphenyl)-trans,trans-bicyclohexyl
4-decyl-4'-(3-fluoro-4-difluoromethoxyphenyl)-trans,trans-bicyclohexyl The following were prepared analogously from the corresponding thiols:
4-difluoromethylthio-4'-methyl-biphenyl
4-difluoromethylthio-4'-ethyl-biphenyl
4-difluoromethylthio-4'-propyl-biphenyl
4-difluoromethylthio-4'-butyl-biphenyl
4-difluoromethylthio-4'-pentyl-biphenyl
4-difluoromethylthio-4'-hexyl-biphenyl
4-difluoromethylthio-4'-heptyl-biphenyl
4-difluoromethylthio-4'-octyl-biphenyl
4-difluoromethylthio-4'-nonyl-biphenyl
4-difluoromethylthio-4'-decyl-biphenyl
difluoromethylthio-4-(trans-4-methylcyclohexyl)-benzene
difluoromethylthio-4-(trans-4-ethylcyclohexyl)-benzene
difluoromethylthio-4-(trans-4-propylcyclohexyl)-benzene
difluoromethylthio-4-(trans-4-butylcyclohexyl)-benzene
difluoromethylthio-4-(trans-4-pentylcyclohexyl)-benzene
difluoromethylthio-4-(trans-4-hexylcyclohexyl)-benzene
difluoromethylthio-4-(trans-4-heptylcyclohexyl)-benzene
difluoromethylthio-4-(trans-4-octylcyclohexyl)-benzene
difluoromethylthio-4-(trans-4-nonylcyclohexyl)-benzene
difluoromethylthio-4-(trans-4-decylcyclohexyl)-benzene
4-difluoromethylthio-4'-(trans-4-methylcyclohexyl)-biphenyl
4-difluoromethylthio-4'-(trans-4-ethylcyclohexyl)-biphenyl
4-difluoromethylthio-4'-(trans-4-methylcyclohexyl)- 4-difluoromethylthio-4'-(trans-4-propylcyclohexyl)-biphenyl
4-difluoromethylthio-4'-(trans-4-butylcyclohexyl)-biphenyl
4-difluoromethylthio-4'-(trans-4-pentylcyclohexyl)-biphenyl
4-difluoromethylthio-4'-(trans-4-hexylcyclohexyl)-biphenyl
4-difluoromethylthio-4'-(trans-4-heptylcyclohexyl)-biphenyl
4-difluoromethylthio-4'-(trans-4-octylcyclohexyl)-biphenyl
4-difluoromethylthio-4'-(trans-4-nonylcyclohexyl)-biphenyl
4-difluoromethylthio-4'-(trans-4-decylcyclohexyl)-biphenyl Example 2a Difluoromethoxy-(5-propyl-1,3-dioxan-2-yl)-benzene 17.2 g of p-difluoromethoxybenzaldehyde (commercially available from Fluorochem. Ltd. (GB)), 10.4 g of ethylpropanediol and 0.2 g of p-TsOH are heated to boiling for 2 hours in 100 ml of toluene. After evaporation of the solvent, the mixture is worked up as usual.

The following were prepared analogously:
difluoromethoxy-(5-ethyl-1,3-dioxan-2-yl)-benzene
difluoromethoxy-(5-butyl-1,3-dioxan-2-yl)-benzene
difluoromethoxy-(5-pentyl-1,3-dioxan-2-yl)-benzene
difluoromethoxy-(5-hexyl-1,3-dioxan-2-yl)-benzene
difluoromethoxy-(5-heptyl-1,3-dioxan-2-yl)-benzene
difluoromethoxy-(5-octyl-1,3-dioxan-2-yl)-benzene
difluoromethoxy-(5-nonyl-1,3-dioxan-2-yl)-benzene
difluoromethoxy-(5-decyl-1,3-dioxan-2-yl)-benzene
difluoromethoxy-4-[5-(trans-4-ethylcyclohexyl)-1,3-dioxan-2-yl]-benzene
difluoromethoxy-4-[5-(trans-4-propylcyclohexyl)-1,3-dioxan-2-yl]-benzene
difluoromethoxy-4-[5-(trans-4-butylcyclohexyl)-1,3-dioxan-2-yl]-benzene
difluoromethoxy-4-[5-(trans-4-pentylcyclohexyl)-1,3-dioxan-2-yl]-benzene
difluoromethoxy-4-[5-(trans-4-hexylcyclohexyl)-1,3-dioxan-2-yl]-benzene
difluoromethoxy-4-[5-(trans-4-heptylcyclohexyl)-1,3-dioxan-2-yl]-benzene
difluoromethoxy-4-[5-(trans-4-octylcyclohexyl)-1,3-dioxan-2-yl]-benzene
difluoromethoxy-4-[5 -(trans-4-nonylcyclohexyl)-1,3-dioxan-2-yl]-benzene
difluoromethoxy-4-[5-(trans-4-decylcyclohexyl)-1,3-dioxan-2-yl]-benzene Example 3a Difluoromethoxy-4-(5-heptyl-1,3-pyrimidin-2-yl)-benzene A mixture of 22.2 g of p-difluoromethoxybenzimidamide hydrochloride (available from the nitrile via the corresponding ethyl benzimidate hydrochloride) and 31.8 g of heptylmalonedialdehyde bis(diethyl) acetal is stirred at 150° C. for 15 hours. After cooling, the mixture is worked up as usual. m.p.: 26° C., c.p.: 32° C., Δn: 0.112, viscosity: 16.

The following were prepared analogously:
difluoromethoxy-4-(5-methyl-1,3-pyrimidin-2-yl)-benzene
difluoromethoxy-4-(5-ethyl-1,3-pyrimidin-2-yl)-benzene
difluoromethoxy-4-(5-propyl-1,3-pyrimidin-2-yl)-benzene, m.p.: 41° C., c.p. (extrapolated): 0° C., Δn=0.150, viscosity: 14
difluoromethoxy-4-(5-butyl-1,3-pyrimidin-2-yl)-benzene
difluoromethoxy-4-(5-pentyl-1,3-pyrimidin-2-yl)-benzene, m.p.: 21° C., c.p.: 26° C., Δn: 0.13, viscosity: 14
difluoromethoxy-4-(5-hexyl-1,3-pyrimidin-2-yl)-benzene
difluoromethoxy-4-(5-octyl-1,3-pyrimidin-2-yl)-benzene
difluoromethoxy-4-(5-nonyl-1,3-pyrimidin-2-yl)-benzene
difluoromethoxy-4-(5-decyl-1,3-pyrimidin-2-yl)-benzene
difluoromethoxy-4-(5-methoxy-1,3-pyrimidin-2-yl)-benzene
difluoromethoxy-4-(5-ethoxy-1,3-pyrimidin-2-yl)-benzene
difluoromethoxy-4-(5-propoxy-1,3-pyrimidin-2-yl)-benzene
difluoromethoxy-4-(5-butoxy-1,3-pyrimidin-2-yl)-benzene
difluoromethoxy-4-(5-pentoxy-1,3-pyrimidin-2-yl)-benzene
difluoromethoxy-4-(5-hexoxy-1,3-pyrimidin-2-yl)-benzene
difluoromethoxy-4-(5-heptoxy-1,3-pyrimidin-2-yl)-benzene difluoromethoxy-4-(5-octoxy-1,3-pyrimidin-2-yl)-benzene
difluoromethoxy-4-(5-nonoxy-1,3-pyrimidin-2-yl)-benzene
difluoromethoxy-4-(5-decoxy-1,3-pyrimidin-2-yl)-benzene
difluoromethoxy-4-[5-(trans-4-methylcyclohexyl)-1,3-pyrimidin- 2-yl]-benzene
difluoromethoxy-4-[5-(trans-4-ethylcyclohexyl)-1,3-pyrimidin- 2-yl]-benzene
difluoromethoxy-4-[5-(trans-4-propylcyclohexyl)-1,3-pyrimidin- 2-yl]-benzene
difluoromethoxy-4-[5-(trans-4-butylcyclohexyl)-1,3-pyrimidin- 2-yl]-benzene
difluoromethoxy-4-[5-(trans-4-pentylcyclohexyl)-1,3-pyrimidin- 2-yl]-benzene
difluoromethoxy-4-[5-(trans-4-hexylcyclohexyl)-1,3-pyrimidin- 2-yl]-benzene
difluoromethoxy-4-[5-(trans-4-heptylcyclohexyl)-1,3-pyrimidin- 2-yl]-benzene
difluoromethoxy-4-[5-(trans-4-octylcyclohexyl)-1,3-pyrimidin- 2-yl]-benzene
difluoromethoxy-4-[5-(trans-4-nonylcyclohexyl)-1,3-pyrimidin- 2-yl]-benzene
difluoromethoxy-4-[5-(trans-4-decylcyclohexyl)-1,3-pyrimidin- 2-yl]-benzene
difluoromethoxy-4-[5-(2-(trans-4-methylcyclohexyl)-ethyl)- 1,3-pyrimidin-2-yl]-benzene
difluoromethoxy-4-[5-(2-(trans-4-ethylcyclohexyl)-ethyl)-1,3-pyrimidin-2-yl]-benzene
difluoromethoxy-4-[5-(2-(trans-4-propylcyclohexyl)-ethyl)-1,3-pyrimidin-2-yl]-benzene
difluoromethoxy-4-[5-(2-(trans-4-butylcyclohexyl)-ethyl)-1,3-pyrimidin-2-yl]-benzene
difluoromethoxy-4-[5-(2-(trans-4-pentylcyclohexyl)-ethyl)-1,3-pyrimidin-2-yl]-benzene
difluoromethoxy-4-[5-(2-(trans-4-hexylcyclohexyl)-ethyl)-1,3-pyrimidin-2-yl]-benzene
difluoromethoxy-4-[5-(2-(trans-4-heptylcyclohexyl)-ethyl)-1,3-pyrimidin-2-yl]-benzene
difluoromethoxy-4-[5-(2-(trans-4-octylcyclohexyl)-ethyl)-1,3-pyrimidin-2-yl]-benzene
difluoromethoxy-4-[5-(2-(trans-4-nonylcyclohexyl)-ethyl)-1,3-pyrimidin-2-yl]-benzene
difluoromethoxy-4-[5-(2-(trans-4-decylcyclohexyl)-ethyl)-1,3-pyrimidin-2-yl]-benzene Using 4-mercaptobenzonitrile (available from 4-cyanophenol by reaction with dimethylcarbamoyl chloride and thermal rearrangement), the following were prepared analogously:

difluoromethylthio-4-(5-methyl-1,3-pyrimidin-2-yl)-benzene
difluoromethylthio-4-(5-ethyl-1,3-pyrimidin-2-yl)-benzene
difluoromethylthio-4-(5-propyl-1,3-pyrimidin-2-yl)-benzene
difluoromethylthio-4-(5-butyl-1,3-pyrimidin-2-yl)-benzene
difluoromethylthio-4-(5-pentyl-1,3-pyrimidin-2-yl)-benzene
difluoromethylthio-4-(5-hexyl-1,3-pyrimidin-2-yl)-benzene
difluoromethylthio-4-(5-heptyl-1,3-pyrimidin-2-yl)-benzene
difluoromethylthio-4-(5-octyl-1,3-pyrimidin-2-yl)-benzene
difluoromethylthio-4-(5-nonyl-1,3-pyrimidin-2-yl)-benzene
difluoromethylthio-4-(5-decyl-1,3-pyrimidin-2-yl)-benzene
difluoromethylthio-4-(5-methoxy-1,3-pyrimidin-2-yl)-benzene
difluoromethylthio-4-(5-ethoxy-1,3-pyrimidin-2-yl)-benzene
difluoromethylthio-4-(5-propoxy-1,3-pyrimidin-2-yl)-benzene
difluoromethylthio-4-(5-butoxy-1,3-pyrimidin-2-yl)-benzene
difluoromethylthio-4-(5-pentoxy-1,3-pyrimidin-2-yl)-benzene
difluoromethylthio-4-(5-hexoxy-1,3-pyrimidin-2-yl)-benzene
difluoromethylthio-4-(5-heptoxy-1,3-pyrimidin-2-yl)-benzene
difluoromethylthio-4-(5-octoxy-1,3-pyrimidin-2-yl)-benzene
difluoromethylthio-4-(5-nonoxy-1,3-pyrimidin-2-yl)-benzene
difluoromethylthio-4-(5-decoxy-1,3-pyrimidin-2-yl)-benzene
difluoromethoxy-4-(5-methylpyridin-2-yl)-benzene
difluoromethoxy-4-(5-ethylpyridin-2-yl)-benzene
difluoromethoxy-4-(5-propylpyridin-2-yl)-benzene
difluoromethoxy-4-(5-butylpyridin-2-yl)-benzene
difluoromethoxy-4-(5-pentylpyridin-2-yl)-benzene
difluoromethoxy-4-(5-hexylpyridin-2-yl)-benzene
difluoromethoxy-4-(5-heptylpyridin-2-yl)-benzene
difluoromethoxy-4-(5-octylpyridin-2-yl)-benzene
difluoromethoxy-2-fluoro-4-(2-octylpyridin-5-yl)-benzene
difluoromethoxy-4-(5-nonylpyridin-2-yl)-benzene
difluoromethoxy-4-(5-decylpyridin-2-yl)-benzene
difluoromethoxy-4-(5-methoxypyridin-2-yl)-benzene
difluoromethoxy-4-(5-ethoxypyridin-2-yl)-benzene
difluoromethoxy-4-(5-propoxypyridin-2-yl)-benzene
difluoromethoxy-4-(5-butoxypyridin-2-yl)-benzene
difluoromethoxy-4-(5-pentoxypyridin-2-yl)-benzene
difluoromethoxy-4-(5-hexoxypyridin-2-yl)-benzene
difluoromethoxy-4-(5-heptoxypyridin-2-yl)-benzene
difluoromethoxy-4-(5-octoxypyridin-2-yl)-benzene
difluoromethoxy-2-fluoro-4-(2-octoxypyridin-5-yl)-benzene
difluoromethoxy-4-(5-nonoxypyridin-2-yl)-benzene
difluoromethoxy-4-(5-decoxypyridin-2-yl)-benzene
4-difluoromethoxy-4'-(5-methyl-1,3-pyrimidin-2-yl)-biphenyl
4-difluoromethoxy-4'-(5-ethyl-1,3-pyrimidin-2-yl)-biphenyl
4-difluoromethoxy-4'-(5-propyl-1,3-pyrimidin-2-yl)-biphenyl
4-difluoromethoxy-4'-(5-butyl-1,3-pyrimidin-2-yl)-biphenyl
4-difluoromethoxy-4'-(5-pentyl-1,3-pyrimidin-2-yl)-biphenyl
4-difluoromethoxy-4'-(5-hexyl-1,3-pyrimidin-2-yl)-biphenyl
4-difluoromethoxy-4'-(5-heptyl-1,3-pyrimidin-2-yl)-biphenyl
4-difluoromethoxy-4'-(5-octyl-1,3-pyrimidin-2-yl)-biphenyl
4-difluoromethoxy-4'-(5-nonyl-1,3-pyrimidin-2-yl)-biphenyl
4-difluoromethoxy-4'-(5-decyl-1,3-pyrimidin-2-yl)-biphenyl Example 4a 4-Benzyloxy-difluoromethoxy-benzene A mixture of 40.0 g of hydroquinone monobenzyl ether, 40 g of NaOH, 200 ml of water and 300 ml of dioxane are heated to 70° C. with stirring. 35.5 g of chlorodifluoromethane are passed into the cooled mixture with vigorous stirring. The reaction mixture is poured into water, and the product is extracted with petroleum ether. The organic phase is dried over $Na_2SO_4$, evaporated, and the residue is chromatographed through a short silica gel column, using petroleum ether/ethyl acetate 8:2 as eluent. A colorless liquid is obtained.

Example 5a a) Hydroquinone monodifluoromethyl ether

A solution of 25.0 g of the product from Example 4 in 100 ml of THF is hydrogenated at room temperature and atmospheric pressure, using 8 g of Pd/C (5% Pd) as catalyst. The catalyst is filtered off, and the filtrate is evaporated.

b) 4-Difluoromethoxyphenyl trans-4-pentylcyclohexanecarboxylate

A solution of 10.3 g of DCC in 50 ml of dichloromethane is added dropwise to a solution maintained at 0° C. of 9.92 g of trans-4-pentylcyclohexanecarboxylic acid, 8.11 g of hydroquinone monodifluoromethyl ether and 611 mg of 4-dimethylaminopyridine in 100 ml of dichloromethane. After stirring at room temperature for 18 hours, the precipitate formed is filtered off, and the filtrate is evaporated. The residue is chromatographed through a silica gel column, using petroleum ether/ethyl acetate 9:1 as eluent. Colorless crystals, m.p.: 54° C., c.p.: 30° C., Δn=0.061, viscosity: 16 are obtained.

The following are prepared analogously:

4-difluoromethoxyphenyl trans-4-ethylcyclohexanecarboxylate
4-difluoromethoxyphenyl trans-4-propylcyclohexanecarboxylate, m.p.: 54° C., c.p.: 0° C., Δn=0.052, viscosity: 10
4-difluoromethoxyphenyl trans-4-butylcyclohexanecarboxylate
4-difluoromethoxyphenyl trans-4-hexylcyclohexanecarboxylate
4-difluoromethoxyphenyl trans-4-heptylcyclohexanecarboxylate
4-difluoromethoxyphenyl trans-4-octylcyclohexanecarboxylate
4-difluoromethoxyphenyl trans-4-nonylcyclohexanecarboxylate
4-difluoromethoxyphenyl trans-4-decylcyclohexanecarboxylate
4-difluoromethoxybiphenyl-4'-yl trans-4-methylcyclohexanecarboxylate
4-difluoromethoxybiphenyl-4'-yl trans-4-ethylcyclohexanecarboxylate
4-difluoromethoxybiphenyl-4'-yl trans-4-propylcyclohexanecarboxylate
4-difluoromethoxybiphenyl-4'-yl trans-4-butylcyclohexanecarboxylate
4-difluoromethoxybiphenyl-4'-yl trans-4-pentylcyclohexanecarboxylate
4-difluoromethoxybiphenyl-4'-yl trans-4-hexylcyclohexanecarboxylate
4-difluoromethoxybiphenyl-4'-yl trans-4-heptylcyclohexanecarboxylate
4-difluoromethoxybiphenyl-4'-yl trans-4-octylcyclohexanecarboxylate
4-difluoromethoxybiphenyl-4'-yl trans-4-nonylcyclohexanecarboxylate
4-difluoromethoxybiphenyl-4'-yl trans-4-decylcyclohexanecarboxylate
4-difluoromethoxyphenyl-4'-methyl trans,trans-bicyclohexane-4-carboxylate
4-difluoromethoxyphenyl-4'-ethyl trans,trans-bicyclohexane-4-carboxylate
4-difluoromethoxyphenyl-4'-propyl trans,trans-bicyclohexane-4-carboxylate
4-difluoromethoxyphenyl-4'-butyl trans,trans-bicyclohexane-4-carboxylate
4-difluoromethoxyphenyl-4'-pentyl trans,trans-bicyclohexane-4-carboxylate, m.p.: 61° C., c.p.: 196.9° C. Δn=0.089
4-difluoromethoxyphenyl-4'-hexyl trans,trans-bicyclohexane-4-carboxylate
4-difluoromethoxyphenyl-4'-heptyl trans,trans-bicyclohexane-4-carboxylate
4-difluoromethoxyphenyl-4'-octyl trans,trans-bicyclohexane-4-carboxylate
4-difluoromethoxyphenyl-4'-nonyl trans,trans-bicyclohexane-4-carboxylate
4-difluoromethoxyphenyl-4'-decyl trans,trans-bicyclohexane-4-carboxylate Using 4-difluoromethylthiophenol (obtainable by esterification of 4-hydroxybenzenesulfonic acid (Aldrich) with acetic acid, conversion to the sulfonyl chloride, reduction to the thiol using zinc/hydrochloric acid, etherification analogously to Example 1a) and alkaline ether cleavage), the following were prepared analogously:

4-difluoromethylthiophenyl trans-4-methylcyclohexanecarboxylate
4-difluoromethylthiophenyl trans-4-ethylcyclohexanecarboxylate
4-difluoromethylthiophenyl trans-4-propylcyclohexanecarboxylate
4-difluoromethylthiophenyl trans-4-butylcyclohexanecarboxylate
4-difluoromethylthiophenyl trans-4-pentylcyclohexanecarboxylate
4-difluoromethylthiophenyl trans-4-hexylcyclohexanecarboxylate
4-difluoromethylthiophenyl trans-4-heptylcyclohexanecarboxylate
4-difluoromethylthiophenyl trans-4-octylcyclohexanecarboxylate
4-difluoromethylthiophenyl trans-4-nonylcyclohexanecarboxylate
4-difluoromethylthiophenyl trans-4-decylcyclohexanecarboxylate
3-fluoro-4-difluoromethylthiophenyl-4'-methyl trans, trans-bicyclohexane-4-carboxylate
3-fluoro-4-difluoromethylthiophenyl-4'-ethyl trans, trans-bicyclohexane-4-carboxylate
3-fluoro-4-difluoromethylthiophenyl-4'-propyl trans, trans-bicyclohexane-4-carboxylate
3-fluoro-4-difluoromethylthiophenyl-4'-butyl trans, trans-bicyclohexane-4-carboxylate
3-fluoro-4-difluoromethylthiophenyl-4'-pentyl trans, trans-bicyclohexane-4-carboxylate
3-fluoro-4-difluoromethylthiophenyl-4'-hexyl trans, trans-bicyclohexane-4-carboxylate
3-fluoro-4-difluoromethylthiophenyl-4'-heptyl trans, trans-bicyclohexane-4-carboxylate
3-fluoro-4-difluoromethylthiophenyl-4'-octyl trans, trans-bicyclohexane-4-carboxylate
3-fluoro-4-difluoromethylthiophenyl-4'-nonyl trans, trans-bicyclohexane-4-carboxylate
3-fluoro-4-difluoromethylthiophenyl-4'-decyl trans, trans-bicyclohexane-4-carboxylate
2,3-difluoro-4-difluoromethylthiophenyl trans-4-methylcyclohexanebenzoate
2,3-difluoro-4-difluoromethylthiophenyl trans-4-ethylcyclohexanebenzoate
2,3-difluoro-4-difluoromethylthiophenyl trans-4-propylcyclohexanebenzoate
2,3-difluoro-4-difluoromethylthiophenyl trans-4-butylcyclohexanebenzoate
2,3-difluoro-4-difluoromethylthiophenyl trans-4-pentylcyclohexanebenzoate
2,3-difluoro-4-difluoromethylthiophenyl trans-4-hexylcyclohexanebenzoate
2,3-difluoro-4-difluoromethylthiophenyl trans-4-heptylcyclohexanebenzoate 2,3-difluoro-4-difluoromethylthiophenyl trans-4-octylcyclohexanebenzoate
2,3-difluoro-4-difluoromethylthiophenyl trans-4-nonylcyclohexanebenzoate
2,3-difluoro-4-difluoromethylthiophenyl trans-4-decylcyclohexanebenzoate

Example 6a a) 4-[2-(4-Benzyloxyphenyl)ethenyl]-4'-pentyl-trans, trans-bicyclohexyl 49.6 g of 4-benzyloxybenzaldehyde and 25.9 g of KOT are added to a suspension of 147.1 g of 4'-pentyl trans,trans-bicyclohexyl-4-methyltriphenylphosphonium iodide in 1 l of THF with ice-cooling. The mixture is stirred for 1 h at 5° C. 2N HCl is then added, until the aqueous phase is neutral, and water is added until the precipitate has been dissolved. The organic phase is separated off, dried over $Na_2SO_4$ and evaporated. The residue is chromatographed through a silica gel column, using petroleum ether/ethyl acetate 95:5 as eluent. Colorless crystals are obtained.

b) 4-[2-(4-Hydroxyphenyl)ethyl]-4'-pentyl-trans,trans-bicyclohexyl

A solution of 34.6 g of product 6aa) in 200 ml of THF is hydrogenated at room temperature and atmospheric pressure, using 10 g of Pd/C (5% Pd) as catalyst. The catalyst is filtered off, and the filtrate is evaporated. A grey crystalline solid is obtained:

c) 4-[2-(4-Difluoromethoxyphenyl)ethyl]-4'-pentyl-trans, trans-bicyclohexyl

The product 6ab) is converted to the difluoromethoxy compound analogously to Example 1, m.p.: 24° C., c.p.: 149.9° C., $\Delta n$=0.097, viscosity: 21.

d) The phosphonium iodide from 6ab) is reacted directly with 4-difluoromethoxybenzaldehyde as described in 6aa), and hydrogenated analogously to 6ab).

The following are prepared analogously:
4-[2-(4-difluoromethoxyphenyl)ethyl]-4'-ethyl-trans, trans-bicyclohexyl
4-[2-(4-difluoromethoxyphenyl)ethyl]-4'-propyl-trans, trans-bicyclohexyl
4-[2-(4-difluoromethoxyphenyl)ethyl]-4'-butyl-trans, trans-bicyclohexyl
4-[2-(4-difluoromethoxyphenyl)ethyl]-4'-hexyl-trans, trans-bicyclohexyl
4-[2-(4-difluoromethoxyphenyl)ethyl]-4'-heptyl-trans, trans-bicyclohexyl
4-[2-(4-difluoromethoxyphenyl)ethyl]-4'-octyl-trans, trans-bicyclohexyl
4-[2-(4-difluoromethoxyphenyl)ethyl]-4'-nonyl-trans, trans-bicyclohexyl
4-[2-(4-difluoromethoxyphenyl)ethyl]-4'-decyl-trans, trans-bicyclohexyl
4-[2-(2,3-difluoro-4-difluoromethoxyphenyl)ethyl]-4'-methyl-trans,trans-bicyclohexyl
4-[2-(2,3-difluoro-4-difluoromethoxyphenyl)ethyl]-4'-ethyl-trans,trans-bicyclohexyl
4-[2-(2,3-difluoro-4-difluoromethoxyphenyl)ethyl]-4'-propyl-trans,trans-bicyclohexyl, 81N 128I
4-[2-(2,3-difluoro-4-difluoromethoxyphenyl)ethyl]-4'-butyl-trans,trans-bicyclohexyl
4-[2-(2,3-difluoro-4-difluoromethoxyphenyl)ethyl]-4'-pentyl-trans,trans-bicyclohexyl
4-[2-(2,3-difluoro-4-difluoromethoxyphenyl)ethyl]-4'-hexyl-trans,trans-bicyclohexyl
4-[2-(2,3-difluoro-4-difluoromethoxyphenyl)ethyl]-4'-heptyl-trans,trans-bicyclohexyl
4-[2-(2,3-difluoro-4-difluoromethoxyphenyl)ethyl]-4'-octyl-trans,trans-bicyclohexyl
4-[2-(2,3-difluoro-4-difluoromethoxyphenyl)ethyl]-4'-nonyl-trans,trans-bicyclohexyl
4-[2-(2,3-difluoro-4-difluoromethoxyphenyl)ethyl]-4'-decyl-trans,trans-bicyclohexyl
4-[2-(trans-4-methylcyclohexyl)ethyl]-4'-difluoromethoxybiphenyl
4-[2-(trans-4-ethylcyclohexyl)ethyl]-4'-difluoromethoxybiphenyl
4-[2-(trans-4-propylcyclohexyl)ethyl]-4'-difluoromethoxybiphenyl
4-[2-(trans-4-butylcyclohexyl)ethyl]-4'-difluoromethoxybiphenyl
4-[2-(trans-4-pentylcyclohexyl)ethyl]-4'-difluoromethoxybiphenyl
4-[2-(trans-4-hexylcyclohexyl)ethyl]-4'-difluoromethoxybiphenyl
4-[2-(trans-4-heptylcyclohexyl)ethyl]-4'-difluoromethoxybiphenyl
4-[2-(trans-4-octylcyclohexyl)ethyl]-4'-difluoromethoxybiphenyl
4-[2-(trans-4-nonylcyclohexyl)ethyl]-4'-difluoromethoxybiphenyl
4-[2-(trans-4-decylcyclohexyl)ethyl]-4'-difluoromethoxybiphenyl
4-difluoromethoxy-[2-(trans-4-methylcyclohexyl)ethyl]-benzene
4-difluoromethoxy-[2-(trans-4-ethylcyclohexyl)ethyl]-benzene, m.p.: −37° C., c.p. (extrapolated): −60° C., $\Delta n$=0.033, viscosity: 6
4-difluoromethoxy-[2-(trans-4-propylcyclohexyl)ethyl]-benzene, m.p.: −2° C., c.p.: −14.5° C., $\Delta n$=0.042, viscosity: 6
4-difluoromethoxy-[2-(trans-4-butylcyclohexyl)ethyl]-benzene
4-difluoromethoxy-[2-(trans-4-pentylcyclohexyl)ethyl]-benzene, m.p.: 4° C., c.p.: 5.1° C., $\Delta n$: 0.065, viscosity: 7
4-difluoromethoxy-[2-(trans-4-hexylcyclohexyl)ethyl]-benzene
4-difluoromethoxy-[2-(trans-4-heptylcyclohexyl)ethyl]-benzene, m.p.: 30° C., c.p.: 16.9° C., $\Delta n$=0.065, viscosity: 8
4-difluoromethoxy-[2-(trans-4-octylcyclohexyl)ethyl]-benzene
4-difluoromethoxy-[2-(trans-4-nonylcyclohexyl)ethyl]-benzene
4-difluoromethoxy-[2-(trans-4-decylcyclohexyl)ethyl]-benzene

Example 7a a) 4-(1H,1H-Difluoroethoxy)-benzaldehyde 16.4 g of 2,2-difluoroethanol are added to a suspension of 3.3 g of sodium hydride in 100 ml of 1,3-dimethyl-2-imidazolidinone, and the mixture is stirred at 30° C. for 2 hours. It is cooled to 0°10° C., and 12.4 g of 4-fluorobenzaldehyde are added. The mixture is stirred at 5° C. for 2 hours and at 90° C. for 4 hours. After cooling, the reaction mixture is poured into 200 ml of 5% HCl, and the product is extracted with ether. The organic phase is dried over $Na_2SO_4$, evaporated, and the residue is distilled. A colorless liquid is obtained.

b) 4-{2-[4-(1H,1H-Difluoroethoxy)-phenyl]-ethenyl}-4'-pentyl-trans,trans-bicyclohexyl 17.1 g of the product 7aa) and 9.3 g of KOT are added to a suspension of 53 g of 4'-pentyl-trans,trans-bicyclohexyl- 4-methyltriphenylphosphonium iodide in 250 ml of THF with ice-cooling. The mixture is stirred at 5° C. for 1 hour. 2N HCl is then added until the aqueous phase is neutral, and water is added until the precipitate has been dissolved. The organic phase is separated off, dried over $Na_2SO_4$ and evaporated. The residue is chromatographed through a silica gel column, using petroleum ether/ethyl acetate 9:1 as eluent. Colorless crystals are obtained.

The following are prepared analogously:

4-{2-[4-(1H,1H-difluoroethoxy)-phenyl]-ethenyl}-4'-ethyl-trans,trans-bicyclohexyl
4-{2-[4-(1H,1H-difluoroethoxy)-phenyl]-ethenyl}-4'-propyl-trans,trans-bicyclohexyl
4-{2-[4-(1H,1H-difluoroethoxy)-phenyl]-ethenyl}-4'-butyl-trans,trans-bicyclohexyl
4-{2-[4-(1H,1H-difluoroethoxy)-phenyl]-ethenyl}-4'-hexyl-trans,trans-bicyclohexyl
4-{2-[4-(1H,1H-difluoroethoxy)-phenyl]-ethenyl}-4'-heptyl-trans,trans-bicyclohexyl
4-{2-[4-(1H,1H-difluoroethoxy)-phenyl]-ethenyl}-4'-octyl-trans,trans-bicyclohexyl
4-{2-[4-(1H,1H-difluoroethoxy)-phenyl]-ethenyl}-4'-nonyl-trans,trans-bicyclohexyl
4-{2-[4-(1H,1H-difluoroethoxy)-phenyl]-ethenyl}-4'-decyl-trans,trans-bicyclohexyl
4-difluoromethoxy-[2-(trans-4-methoxycyclohexyl)-ethenyl]-benzene
4-difluoromethoxy-[2-(trans-4-ethoxycyclohexyl)-ethenyl]-benzene
4-difluoromethoxy-[2-(trans-4-propoxycyclohexyl)-ethenyl]-benzene
4-difluoromethoxy-[2-(trans-4-butoxycyclohexyl)-ethenyl]-benzene
4-difluoromethoxy-[2-(trans-4-pentoxycyclohexyl)-ethenyl]-benzene
4-difluoromethoxy-[2-(trans-4-hexoxycyclohexyl)-ethenyl]-benzene
4-difluoromethoxy-[2-(trans-4-heptoxycyclohexyl)-ethenyl]-benzene
4-difluoromethoxy-[2-(trans-4-octoxycyclohexyl)-ethenyl]-benzene
4-difluoromethoxy-[2-(trans-4-nonoxycyclohexyl)-ethenyl]-benzene
4-difluoromethoxy-[2-(trans-4-decoxycyclohexyl)-ethenyl]-benzene Example 8a 4-{2-[4-1H,1H-Difluoroethoxy)-phenyl]-ethyl}-4'-pentyl-trans,trans-bicyclohexyl 10 g of Pd/C (5% Pd) are added to a solution of 16.8 g of product 7ab) in 150 ml of ethyl acetate, and the mixture is hydrogenated at room temperature and atmospheric pressure. The catalyst is filtered off, the filtrate is evaporated, and the residue is recrystallized from ethanol. Colorless crystals are obtained.

The following are prepared analogously:

4-{2-[4-1H,1H-difluoroethoxy)-phenyl]-ethyl}-4'-ethyl-trans,trans-bicyclohexyl
4-{2-[4-1H,1H-difluoroethoxy)-phenyl]-ethyl}-4'-propyl-trans,trans-bicyclohexyl
4-{2-[4-1H,1H-difluoroethoxy)-phenyl]-ethyl}-4'-butyl-trans,trans-bicyclohexyl
4-{2-[4-1H,1H-difluoroethoxy)-phenyl]-ethyl}-4'-hexyl-trans,trans-bicyclohexyl
4-{2-[4-1H,1H-difluoroethoxy)-phenyl]-ethyl}-4'-heptyl-trans,trans-bicyclohexyl
4-{2-[4-1H,1H-difluoroethoxy)-phenyl]-ethyl}-4'-octyl-trans,trans-bicyclohexyl
4-{2-[4-1H,1H-difluoroethoxy)-phenyl]-ethyl}-4'-nonyl-trans,trans-bicyclohexyl
4-{2-[4-1H,1H-difluoroethoxy)-phenyl]-ethyl}-4'-decyl-trans,trans-bicyclohexyl Example 9a a) 3-[4-(trans-4-Propylcyclohexyl)-phenyl]-propanoic acid A solution of 12.6 g of 3-[4-(trans-4-propylcyclohexyl)-phenyl]-propenoic acid (obtained by condensation of 4-(trans-4-propylcyclohexyl)-benzaldehyde with malonic acid in pyridine) in 120 ml of ethyl acetate is hydrogenated at room temperature and atmospheric pressure, using 4 g of Pd/C (5% Pd) as catalyst. The catalyst is filtered off, and the filtrate is evaporated. Colorless crystals are obtained.

b) 3-[4-(trans-4-Propylcyclohexyl)-phenyl]-propanol

A solution of 11.3 g of product 9aa) in 50 ml of THF is added dropwise to a suspension maintained at 0° C. of 1.52 g of lithium alanate in 200 ml of THF. After stirring at room temperature for 2 hours, the reaction mixture is poured into water and acidified with 13% HCl. The mixture is extracted with ether, the organic phase is dried and evaporated. Colorless crystals are obtained.

c) 3-[4-(trans-4-Propylcyclohexyl)-phenyl]-propanol

A solution of 7.2 g of dimethyl sulfoxide in 12 ml of dichloromethane is added dropwise to a solution maintained at −75° C. of 5.7 g of oxalyl chloride in 80 ml of dichloromethane, and the mixture is stirred for 5 minutes. A solution of 10.3 g of product 9ab) in 20 ml of dichloromethane is then added dropwise, and the mixture is stirred for another 15 minutes. 28 ml of triethylamine are then added, the mixture is allowed to reach 0° C., and 100 ml of water and 200 ml of ether are added. The organic phase is separated off, washed with water and saturated NaCl solution, dried over $Na_2SO_4$ and evaporated. The residue is chromatographed through a silica gel column, using petroleum ether/ethyl acetate 8:2 as eluent. A colorless oil is obtained.

d) 1-(3,3-Difluoropropyl)-4-(trans-4-propylcyclohexyl)-benzene

A solution of 4.1 g of DAST in 50 ml of hexane is added dropwise to a solution of 7.9 g of product 9ac) in 100 ml of hexane, and the mixture is stirred at room temperature for 2 hours. 100 ml of water are added, and the organic phase is separated off, dried over $Na_2SO_4$ and evaporated. The residue is chromatographed through a silica gel column, using petroleum ether as eluent, and is distilled in a kugelrohr apparatus. A colorless liquid is obtained. m.p.: 12° C., c.p.: −60° C. (extrapolated), Δn=0.032, viscosity: 11.

The following are prepared analogously:

1-(3,3-difluoropropyl)-4-(trans-4-ethylcyclohexyl)-benzene
1-(3,3-difluoropropyl)-4-(trans-4-butylcyclohexyl)-benzene
1-(3,3-difluoropropyl)-4-(trans-4-pentylcyclohexyl)-benzene
1-(3,3-difluoropropyl)-4-(trans-4-hexylcyclohexyl)-benzene
1-(3,3-difluoropropyl)-4-(trans-4-heptylcyclohexyl)-benzene
1-(3,3-difluoropropyl)-4-(trans-4-octylcyclohexyl)-benzene
1-(3,3-difluoropropyl)-4-(trans-4-nonylcyclohexyl)-benzene
1-(3,3-difluoropropyl)-4-(trans-4-decylcyclohexyl)-benzene

Example 10a 1H,1H-Difluoroethyl 4'-pentyl-trans,trans-bicyclohexane-4-carboxylate A mixture of 36.5 g of 4'-pentyl-trans,trans-bicyclohexane-4-carboxylic acid and 50 ml of thionyl chloride is heated to boiling for 1 hour. Excess thionyl chloride is distilled off, 50 ml of toluene are added to the residue, and the mixture is transferred to a dropping funnel. This solution is added dropwise to a solution of 11.9 g of 2,2-difluoroethanol and 43.3 ml of pyridine in 100 ml of toluene. The reaction mixture is heated to boiling for 1 hour and then left to stand at room temperature for 18 hours. 100 ml of 2N HCl are added, and the organic phase is separated off. The organic phase is washed twice with water, dried over $Na_2SO_4$ and evaporated. The residue is taken up in 50 ml of THF and 50 ml of 5% aqueous ammonia, and the mixture is stirred for 1 hour. It is extracted with petroleum ether, the organic phase is dried over $Na_2SO_4$ and evaporated. The residue is recrystallized from acetonitrile. Colorless crystals are obtained.

The following are prepared analogously:
1H,1H-difluoroethyl 4'-ethyl-trans,trans-bicyclohexane-4-carboxylate
1H,1H-difluoroethyl 4'-propyl-trans,trans-bicyclohexane-4-carboxylate
1H,1H-difluoroethyl 4'-butyl-trans,trans-bicyclohexane-4-carboxylate
1H,1H-difluoroethyl 4'-hexyl-trans,trans-bicyclohexane-4-carboxylate
1H,1H-difluoroethyl 4'-heptyl-trans,trans-bicyclohexane-4-carboxylate
1H,1H-difluoroethyl 4'-octyl-trans,trans-bicyclohexane-4-carboxylate
1H,1H-difluoroethyl 4'-nonyl-trans,trans-bicyclohexane-4-carboxylate
1H,1H-difluoroethyl 4'-decyl-trans,trans-bicyclohexane-4-carboxylate
1H,1H-difluoroethyl trans-4-(4-methylphenyl)-cyclohexanecarboxylate
1H,1H-difluoroethyl trans-4-(4-ethylphenyl)-cyclohexanecarboxylate
1H,1H-difluoroethyl trans-4-(4-propylphenyl)-cyclohexanecarboxylate
1H,1H-difluoroethyl trans-4-(4-butylphenyl)-cyclohexanecarboxylate
1H,1H-difluoroethyl trans-4-(4-pentylphenyl)-cyclohexanecarboxylate
1H,1H-difluoroethyl trans-4-(4-hexylphenyl)-cyclohexanecarboxylate
1H,1H-difluoroethyl trans-4-(4-heptylphenyl)-cyclohexanecarboxylate
1H,1H-difluoroethyl trans-4-(4-octylphenyl)-cyclohexanecarboxylate
1H,1H-difluoroethyl trans-4-(4-nonylphenyl)-cyclohexanecarboxylate
1H,1H-difluoroethyl trans-4-(4-decylphenyl)-cyclohexanecarboxylate
1H,1H-difluoroethyl trans-4-(4-methoxyphenyl)-cyclohexanecarboxylate
1H,1H-difluoroethyl trans-4-(4-ethoxyphenyl)-cyclohexanecarboxylate
1H,1H-difluoroethyl trans-4-(4-propoxyphenyl)-cyclohexanecarboxylate
1H,1H-difluoroethyl trans-4-(4-butoxyphenyl)-cyclohexanecarboxylate
1H,1H-difluoroethyl trans-4-(4-pentoxyphenyl)-cyclohexanecarboxylate
1H,1H-difluoroethyl trans-4-(3-fluoro-4-pentoxyphenyl)-cyclohexanecarboxylate
1H,1H-difluoroethyl trans-4-(4-hexoxyphenyl)-cyclohexanecarboxylate
1H,1H-difluoroethyl trans-4-(4-heptoxyphenyl)-cyclohexanecarboxylate
1H,1H-difluoroethyl trans-4-(4-octoxyphenyl)-cyclohexanecarboxylate
1H,1H-difluoroethyl trans-4-(4-nonoxyphenyl)-cyclohexanecarboxylate
1H,1H-difluoroethyl trans-4-(4-decoxyphenyl)-cyclohexanecarboxylate
1H,1H-difluoroethyl 4-(trans-4-ethylcyclohexyl)-benzoate
1H,1H-difluoroethyl 4-(trans-4-propylcyclohexyl)-benzoate
1H,1H-difluoroethyl 4-(trans-4-butylcyclohexyl)-benzoate
1H,1H-difluoroethyl 4-(trans-4-pentylcyclohexyl)-benzoate
1H,1H-difluoroethyl 4-(trans-4-hexylcyclohexyl)-benzoate
1H,1H-difluoroethyl 4-(trans-4-heptylcyclohexyl)-benzoate
1H,1H-difluoroethyl 4-(trans-4-octylcyclohexyl)-benzoate
1H,1H-difluoroethyl 4-(trans-4-nonylcyclohexyl)-benzoate
1H,1H-difluoroethyl 4-(trans-4-decylcyclohexyl)-benzoate

Example 11a a) 4-(trans-4-Formylcyclohexyl)-4'-pentylbiphenyl 112 ml of a 20% solution of DIBALH in hexane are added dropwise to a solution of 33.2 g of 4-(trans-4-cyanocyclohexyl)- 4'-pentylbiphenyl in 1 l of pentane, and the mixture is stirred for 18 hours. Water is then added dropwise until the evolution of gas subsides and then 200 ml of 25% sulfuric acid are added dropwise. The organic phase is separated off, dried over $Na_2SO_4$ and evaporated. Colorless deliquescent crystals are obtained.

b) 4-(trans-4-Difluoromethylcyclohexyl)-4'-pentylbiphenyl

A solution of 6.9 g of DAST in 10 ml of dichloromethane is added dropwise to a solution of 18.0 g of product 11aa) in 30 ml of dichloromethane at room temperature, and the mixture is stirred for 18 hours. 150 ml of water are added, the organic phase is separated off, dried over $Na_2SO_4$ and evaporated. The residue is chromatographed through a silica gel column, using petroleum ether/ethyl acetate 95:5. Colorless crystals are obtained.

The following are prepared analogously:
4-(trans-4-difluoromethylcyclohexyl)-4'-ethylbiphenyl
4-(trans-4-difluoromethylcyclohexyl)-2',3'-difluoro-4'-propylbiphenyl
4-(trans-4-difluoromethylcyclohexyl)-4'-propylbiphenyl
4-(trans-4-difluoromethylcyclohexyl)-4'-butylbiphenyl
4-(trans-4-difluoromethylcyclohexyl)-4'-hexylbiphenyl
4-(trans-4-difluoromethylcyclohexyl)-4'-heptylbiphenyl
4-(trans-4-difluoromethylcyclohexyl)-4'-octylbiphenyl
4-(trans-4-difluoromethylcyclohexyl)-4'-nonylbiphenyl
4-(trans-4-difluoromethylcyclohexyl)-4'-decylbiphenyl
4-(trans-4-difluoromethylcyclohexyl)-4'-methoxybiphenyl
4-(trans-4-difluoromethylcyclohexyl)-4'-ethoxybiphenyl
4-(trans-4-difluoromethylcyclohexyl)-3'-cyano-4'-ethoxybiphenyl
4-(trans-4-difluoromethylcyclohexyl)-4'-propoxybiphenyl
4-(trans-4-difluoromethylcyclohexyl)-4'-butoxybiphenyl
4-(trans-4-difluoromethylcyclohexyl)-4'-pentoxybiphenyl
4-(trans-4-difluoromethylcyclohexyl)-4'-hexoxybiphenyl
4-(trans-4-difluoromethylcyclohexyl)-4'-heptoxybiphenyl
4-(trans-4-difluoromethylcyclohexyl)-4'-octoxybiphenyl
4-(trans-4-difluoromethylcyclohexyl)-4'-nonoxybiphenyl
4-(trans-4-difluoromethylcyclohexyl)-4'-decoxybiphenyl

Example b 12a a) 4'-Propyl-trans,trans-bicyclohexane-4-carboxaldehyde

A solution of 59.6 g of 4-hydroxymethyl-4'-propyl-trans,trans-bicyclohexyl in 200 ml of dichloromethane is added dropwise to a suspension of 82.0 g of PCC in 400 ml of dichloromethane. After stirring for 2 hours, 200 ml of ether are added. The mixture is filtered, and the residue is washed with ether. The filtrate is evaporated, and the residue is chromatographed through a short silica gel column, using toluene as eluent. A colorless oil is obtained.

b) 4-Difluoromethyl-4'-propyl-trans,trans-bicyclohexyl

A solution of 2.7 ml of DAST in 30 ml of hexane is added dropwise to a solution of 4.9 g of product 12aa in 100 ml of hexane at room temperature, and the mixture is stirred for 18 hours. 100 ml of water are added, the organic phase is separated off, dried over $Na_2SO_4$ and evaporated. The residue is chromatographed through a silica gel column, using petroleum ether as eluent: a colourless liquid is obtained. m.p.: 19° C., c.p.: 17° C., Δn=0.003, viscosity: 10.

The following are prepared analogously:
4-difluoromethyl-4'-ethyl-trans,trans-bicyclohexyl
4-difluoromethyl-4'-butyl-trans,trans-bicyclohexyl
4-difluoromethyl-4'-pentyl-trans,trans-bicyclohexyl m.p.: 29° C., c.p.: 32.1° C., Δn=0.0, viscosity: 14
4-difluoromethyl-4'-hexyl-trans,trans-bicyclohexyl
4-difluoromethyl-4'-heptyl-trans,trans-bicyclohexyl
4-difluoromethyl-4'-octyl-trans,trans-bicyclohexyl
4-difluoromethyl-4'-nonyl-trans,trans-bicyclohexyl
4-difluoromethyl-4'-decyl-trans,trans-bicyclohexyl Example 13a a) 1-Difluoromethoxy-4-iodobenzene 100 g (0.4.55 mol) of 4-iodophenol and 54.6 g (1.365 mol) of sodium hydroxide are added to a mixture of 300 ml of THF and 30 ml of water. After stirring for about ½ hour, the mixture is evaporated in a rotary evaporator; this is repeated after the addition of 200 ml of toluene. The residue is taken up in 400 ml of THF. The mixture is cooled to 0° C., 47.1 g (0.545 mol) of chlorodifluoromethane are introduced, and the mixture is then stirred for 1 hour. It is then stirred at about +5° C. for 18 hours. The solution above the resulting slurry-like precipitate was decanted off. It was evaporated in a rotary evaporator, and the residue was chromatographed through a silica gel column, using petroleum ether as eluent.

The following were prepared analogously:
1-difluoromethoxy-4-bromobenzene
1-difluoromethoxy-2-fluoro-4-bromobenzene b) 4-Difluoromethoxy-4'-(trans-4-pentylcyclohexyl)-tolan A solution of 15.3 g of 4-(trans-4-pentylcyclohexyl)phenylacetylene (available from the acetophenone by dehydration, using $PCl_5$/KOT), 16.2 g of difluoromethoxy- 4-iodobenzene, 100 ml of triethylamine, 0.085 g of bis(triphenylphosphine)dichloropalladium and 0.11 g of copper(I) iodide is stirred at room temperature for 3 hours. The cloudy mixture is stirred into dilute hydrochloric acid (500 ml of water+200 ml of 37% hydrochloric acid), extracted with t-butyl methyl ether and worked up as usual. m.p.: 62° C., c.p.: 203.1° C.

The following were prepared analogously:
4-difluoromethoxy-4'-(trans-4-methylcyclohexyl)-tolan
4-difluoromethoxy-4'-(trans-4-ethylcyclohexyl)-tolan
4-difluoromethoxy-4'-(trans-4-propylcyclohexyl)-tolan, m.p.: 87° C., c.p.: 212° C.
4-difluoromethoxy-4'-(trans-4-butylcyclohexyl)-tolan
4-difluoromethoxy-4'-(trans-4-pentylcyclohexyl)-tolan
4-difluoromethoxy-4'-(trans-4-hexylcyclohexyl)-tolan
4-difluoromethoxy-4'-(trans-4-heptylcyclohexyl)-tolan
4-difluoromethoxy-4'-(trans-4-octylcyclohexyl)-tolan
4-difluoromethoxy-4'-(trans-4-nonylcyclohexyl)-tolan
4-difluoromethoxy-4'-(trans-4-decylcyclohexyl)-tolan
4-difluoromethoxy-4'-[2-(trans-4-methylcyclohexyl)-ethyl]-tolan
4-difluoromethoxy-4'-[2-(trans-4-ethylcyclohexyl)-ethyl]-tolan
4-difluoromethoxy-4'-[2-(trans-4-propylcyclohexyl)-ethyl]-tolan
4-difluoromethoxy-4'-[2-(trans-4-butylcyclohexyl)-ethyl]-tolan
4-difluoromethoxy-4'-[2-(trans-4-pentylcyclohexyl)-ethyl]-tolan
4-difluoromethoxy-4'-[2-(trans-4-hexylcyclohexyl)-ethyl]-tolan
4-difluoromethoxy-4'-[2-(trans-4-heptylcyclohexyl)-ethyl]-tolan
4-difluoromethoxy-4'-[2-(trans-4-octylcyclohexyl)-ethyl]-tolan
4-difluoromethoxy-4'-[2-(trans-4-nonylcyclohexyl)-ethyl]-tolan
4-difluoromethoxy-4'-[2-(trans-4-decylcyclohexyl)-ethyl]-tolan
4-difluoromethoxy-4'-methyl-tolan
4-difluoromethoxy-4'-ethyl-tolan
4-difluoromethoxy-4'-propyl-tolan m.p.: 50° C., c.p. (extrapolated): 10° C., viscosity: 7
4-difluoromethoxy-4'-butyl-tolan
4-difluoromethoxy-4'-pentyl-tolan
4-difluoromethoxy-4'-hexyl-tolan
4-difluoromethoxy-4'-heptyl-tolan
4-difluoromethoxy-4'-octyl-tolan
4-difluoromethoxy-4'-nonyl-tolan
4-difluoromethoxy-4'-decyl-tolan Using 4-(difluoromethylthio)-iodobenzene (obtainable by chlorosulfonation of iodobenzene, reduction to the 4-mercaptoiodobenzene, using zinc in dilute hydrochloric .acid, and etherification analogously to Example 1), the following were prepared analogously:
4-difluoromethylthio-4'-(trans-4-methylcyclohexyl)-tolan
4-difluoromethylthio-4'-(trans-4-ethylcyclohexyl)-tolan
4-difluoromethylthio-4'-(trans-4-propylcyclohexyl)-tolan
4-difluoromethylthio-4'-(trans-4-butylcyclohexyl)-tolan
4-difluoromethylthio-4'-(trans-4-pentylcyclohexyl)-tolan
4-difluoromethylthio-4'-(trans-4-hexylcyclohexyl)-tolan
4-difluoromethylthio-4'-(trans-4-heptylcyclohexyl)-tolan
4-difluoromethylthio-4'-(trans-4-octylcyclohexyl)-tolan
4-difluoromethylthio-4'-(trans-4-nonylcyclohexyl)-tolan
4-difluoromethylthio-4'-(trans-4-decylcyclohexyl)-tolan Example 14a 4-(2,2-Difluoroethyl)-4'-pentyl-trans,trans-bicyclohexyl 13 g of 4-(2-oxoethyl)-4'-pentyl-trans,trans-bicyclohexyl (available from bicyclohexanecarboxylic acid, reduction to the alcohol, conversion to the nitrile and conversion to the aldehyde with DIBALH) are dissolved in 100 ml of hexane. At room temperature, a solution of 6.2 ml of DAST in 100 ml of hexane is added dropwise, and stirring of the mixture at room temperature is continued for 10 hours. It is then worked up as usual. m.p.: −1° C., c.p.: 82° C., Δn=0.040, viscosity: 11

The following were prepared analogously:
4-(2,2-difluoroethyl)-4'-methyl-trans,trans-bicyclohexyl
4-(2,2-difluoroethyl)-4'-ethyl-trans,trans-bicyclohexyl
4-(2,2-difluoroethyl)-4'-propyl-trans,trans-bicyclohexyl
4-(2,2-difluoroethyl)-4'-butyl-trans,trans-bicyclohexyl
4-(2,2-difluoroethyl)-4'-hexyl-trans,trans-bicyclohexyl
4-(2,2-difluoroethyl)-4'-heptyl-trans,trans-bicyclohexyl 4-(2,2-difluoroethyl)-4'-octyl-trans,trans-bicyclohexyl
4-(2,2-difluoroethyl)-4'-nonyl-trans,trans-bicyclohexyl
4-(2,2-difluoroethyl)-4'-decyl-trans,trans-bicyclohexyl

Example 15a 1-(4-Ethoxyphenyl)-2-(4'-difluoromethoxyphenyl)-ethene 22.2 g of 4-ethoxystyrene, 33-5 g of 4-(difluoromethoxy)bromobenzene (available from 4-bromophenol analogously to Example 1a)), 0.67 g of palladium(II) acetate, 20.8 ml of triethylamine and 1.83 g of tri-o-tolylphosphine are heated to boiling in 225 ml of acetonitrile for 24 hours. After cooling to 0° C., the crystals are filtered off with suction and washed with acetonitrile and water. m.p.: 177° C.

The following were prepared analogously:
1-(4-methoxyphenyl)-2-(4'-difluoromethoxyphenyl)-ethene
1-(4-propoxyphenyl)-2-(4'-difluoromethoxyphenyl)-ethene
1-(4-butoxyphenyl)-2-(4'-difluoromethoxyphenyl)-ethene
1-(4-pentoxyphenyl)-2-(4'-difluoromethoxyphenyl)-ethene
1-(4-hexoxyphenyl)-2-(4'-difluoromethoxyphenyl)-ethene
1-(4-heptoxyphenyl)-2-(4'-difluoromethoxyphenyl)-ethene
1-(4-octoxyphenyl)-2-(4'-difluoromethoxyphenyl)-ethene
1-(4-nonoxyphenyl)-2-(4'-difluoromethoxyphenyl)-ethene
1-(4-decoxyphenyl)-2-(4'-difluoromethoxyphenyl)-ethene
1-[4-(trans-4-methylcyclohexyl)-phenyl]-2-(4'-difluoromethoxyphenyl)-ethene
1-[4-(trans-4-ethylcyclohexyl)-phenyl]-2-(4'-difluoromethoxyphenyl)-ethene
1-[4-(trans-4-propylcyclohexyl)-phenyl]-2-(4'-difluoromethoxyphenyl)-ethene
1-[4-(trans-4-butylcyclohexyl)-phenyl]-2-(4'-difluoromethoxyphenyl)-ethene
1-[4-(trans-4-pentylcyclohexyl)-phenyl]-2-(4'-difluoromethoxyphenyl)-ethene
1-[4-(trans-4-hexylcyclohexyl)-phenyl]-2-(4'-difluoromethoxyphenyl)-ethene
1-[4-(trans-4-heptylcyclohexyl)-phenyl]-2-(4'-difluoromethoxyphenyl)-ethene
1-[4-(trans-4-octylcyclohexyl)-phenyl]-2-(4'-difluoromethoxyphenyl)-ethene
1-[4-(trans-4-nonylcyclohexyl)-phenyl]-2-(4'-difluoromethoxyphenyl)-ethene
1-[4-(trans-4-decylcyclohexyl)-phenyl]-2-(4'-difluoromethoxyphenyl)-ethene
1-[4-(5-methyl-1,3-pyrimidin-2-yl)-phenyl]-2-(4'-difluoromethoxyphenyl)-ethene
1-[4-(5-ethyl-1,3-pyrimidin-2-yl)-phenyl]-2-(4'-difluoromethoxyphenyl)-ethene
1-[4-(5-propyl-1,3-pyrimidin-2-yl)-phenyl]-2-(4'-difluoromethoxyphenyl)-ethene
1-[4-(5-butyl-1,3-pyrimidin-2-yl)-phenyl]-2-(4'-difluoromethoxyphenyl)-ethene
1-[4-(5-pentyl-1,3-pyrimidin-2-yl)-phenyl]-2-(4'-difluoromethoxyphenyl)-ethene
1-[4-(5-hexyl-1,3-pyrimidin-2-yl)-phenyl]-2-(4'-difluoromethoxyphenyl)-ethene
1-[4-(5-heptyl-1,3-pyrimidin-2-yl)-phenyl]-2-(4'-difluoromethoxyphenyl)-ethene
1-[4-(5-octyl-1,3-pyrimidin-2-yl)-phenyl]-2-(4'-difluoromethoxyphenyl)-ethene
1-[4-(5-nonyl-1,3-pyrimidin-2-yl)-phenyl]-2-(4'-difluoromethoxyphenyl)-ethene
1-[4-(5-decyl-1,3-pyrimidin-2-yl)-phenyl]-2-(4'-difluoromethoxyphenyl)-ethene

Example 16a 1-(4-Ethoxyphenyl)-2-(4'-difluoromethoxyphenyl)-ethane 19.7 g of 1-(4-ethoxyphenyl)-2-(4'-difluoromethoxyphenyl)-ethene are hydrogenated in 150 ml of THF analogously to Example 6ab), using 6 g of Pd/C (5% Pd) as catalyst. m.p.: 37° C., Δn=0.103, viscosity: 8

The following were prepared analogously:
1-(4-methoxyphenyl)-2-(4'-difluoromethoxyphenyl)-ethane
1-(4-propoxyphenyl)-2-(4'-difluoromethoxyphenyl)-ethane
1-(4-butoxyphenyl)-2-(4'-difluoromethoxyphenyl)-ethane
1-(4-pentoxyphenyl)-2-(4'-difluoromethoxyphenyl)-ethane
1-(4-hexoxyphenyl)-2-(4'-difluoromethoxyphenyl)-ethane
1-(4-heptoxyphenyl)-2-(4'-difluoromethoxyphenyl)-ethane
1-(4-octoxyphenyl)-2-(4'-difluoromethoxyphenyl)-ethane
1-(4-nonoxyphenyl)-2-(4'-difluoromethoxyphenyl)-ethane
1-(4-decoxyphenyl)-2-(4'-difluoromethoxyphenyl)-ethane
1-(4-methylphenyl)-2-(4-difluoromethoxybiphenyl-4'-yl)-ethane
1-(4-ethylphenyl)-2-(4-difluoromethoxybiphenyl-4'-yl)-ethane
1-(4-propylphenyl)-2-(4-difluoromethoxybiphenyl-4'-yl)-ethane
1-(4-butylphenyl)-2-(4-difluoromethoxybiphenyl-4'-yl)-ethane
1-(4-pentylphenyl)-2-(4-difluoromethoxybiphenyl-4'-yl)-ethane
1-(4-hexylphenyl)-2-(4-difluoromethoxybiphenyl-4'-yl)-ethane
1-(4-heptylphenyl)-2-(4-difluoromethoxybiphenyl-4'-yl)-ethane
1-(4-octylphenyl)-2-(4-difluoromethoxybiphenyl-4'-yl)-ethane
1-(4-nonylphenyl)-2-(4-difluoromethoxybiphenyl-4'-yl)-ethane
1-(4-decylphenyl)-2-(4-difluoromethoxybiphenyl-4'-yl)-ethane
1-(4-methoxyphenyl)-2-(4-difluoromethoxybiphenyl-4'-yl)-ethane
1-(4-ethoxyphenyl)-2-(4-difluoromethoxybiphenyl-4'-yl)-ethane, m.p.: 153°, c.p. (extrapolated): 110°, Δn: 0.118
1-(4-propoxyphenyl)-2-(4-difluoromethoxybiphenyl-4'-yl)-ethane
1-(4-butoxyphenyl)-2-(4-difluoromethoxybiphenyl-4'-yl)-ethane
1-(4-pentoxyphenyl)-2-(4-difluoromethoxybiphenyl-4'-yl)-ethane
1-(4-hexoxyphenyl)-2-(4-difluoromethoxybiphenyl-4'-yl)-ethane
1-(4-heptoxyphenyl)-2-(4-difluoromethoxybiphenyl-4'-yl)ethane
1-(4-octoxyphenyl)-2-(4-difluoromethoxybiphenyl-4'-yl)-ethane
1-(4-nonoxyphenyl)-2-(4-difluoromethoxybiphenyl-4'-yl)-ethane
1-(4-decoxyphenyl)-2-(4-difluoromethoxybiphenyl-4'-yl)-ethane
1-[4-(trans-4-methylcyclohexyl)-phenyl]-2-(4'-difluoromethoxyphenyl)-ethane
1-[4-(trans-4-ethylcyclohexyl)-phenyl]-2-(4'-difluoromethoxyphenyl)-ethane
1-[4-(trans-4-propylcyclohexyl)-phenyl]-2-(4'-difluoromethoxyphenyl)-ethane, m.p.: 51° C., c.p.: 79.6° C., Δn= 0.125
1-[4-(trans-4-butylcyclohexyl)-phenyl]-2-(4'-difluoromethoxyphenyl)-ethane
1-[4-(trans-4-pentylcyclohexyl)-phenyl]-2-(4'-difluoromethoxyphenyl)-ethane, m.p.: 32° C., c.p.: 90.2° C., Δn=0.123
1-[4-(trans-4-hexylcyclohexyl)-phenyl]-2-(4'-difluoromethoxyphenyl)-ethane
1-[4-(trans-4-heptylcyclohexyl)-phenyl]-2-(4'-difluoromethoxyphenyl)-ethane
1-[4-(trans-4-octylcyclohexyl)-phenyl]-2-(4'-difluoromethoxyphenyl)-ethane
1-[4-(trans-4-nonylcyclohexyl)-phenyl]-2-(4'-difluoromethoxyphenyl)-ethane 1-[4-(trans-4-decylcyclohexyl)-phenyl]-2-(4'-difluoromethoxyphenyl)-ethane
1-[4-(trans-4-methylcyclohexyl)-phenyl]-2-(4'-difluoromethylthiophenyl)-ethane
1-[4-(trans-4-ethylcyclohexyl)-phenyl]-2-(4'-difluoromethylthiophenyl)-ethane
1-[4-(trans-4-propylcyclohexyl)-phenyl]-2-(4'-difluoromethylthiophenyl)-ethane
1-[4-(trans-4-butylcyclohexyl)-phenyl]-2-(4'-difluoromethylthiophenyl)-ethane
1-[4-(trans-4-pentylcyclohexyl)-phenyl]-2-(4'-difluoromethylthiophenyl)-ethane
1-[4-(trans-4-hexylcyclohexyl)-phenyl]-2-(4'-difluoromethylthiophenyl)-ethane
1-[4-(trans-4-heptylcyclohexyl)-phenyl]-2-(4'-difluoromethylthiophenyl)-ethane
1-[4-(trans-4-octylcyclohexyl)-phenyl]-2-(4'-difluoromethylthiophenyl)-ethane
1-[4-(trans-4-nonylcyclohexyl)-phenyl]-2-(4'-difluoromethylthiophenyl)-ethane
1-[4-(trans-4-decylcyclohexyl)-phenyl]-2-(4'-difluoromethylthiophenyl)-ethane
1-[4-(5-methyl-1,3-pyrimidin-2-yl)-phenyl]-2-(4'-difluoromethoxyphenyl)-ethane
1-[4-(5-ethyl-1,3-pyrimidin-2-yl)-phenyl]-2-(4'-difluoromethoxyphenyl)-ethane
1-[4-(5-propyl-1,3-pyrimidin-2-yl)-phenyl]-2-(4'-difluoromethoxyphenyl)-ethane
1-[4-(5-butyl-1,3-pyrimidin-2-yl)-phenyl]-2-(4'-difluoromethoxyphenyl)-ethane
1-[4-(5-pentyl-1,3-pyrimidin-2-yl)-phenyl]-2-(4'-difluoromethoxyphenyl)-ethane
1-[4-(5-hexyl-1,3-pyrimidin-2-yl)-phenyl]-2-(4'-difluoromethoxyphenyl)-ethane
1-[4-(5-heptyl-1,3-pyrimidin-2-yl)-phenyl]-2-(4'-difluoromethoxyphenyl)-ethane
1-[4-(5-octyl-1,3-pyrimidin-2-yl)-phenyl]-2-(4'-difluoromethoxyphenyl)-ethane
1-[4-(5-nonyl-1,3-pyrimidin-2-yl)-phenyl]-2-(4'-difluoromethoxyphenyl)-ethane
1-[4-(5-decyl-1,3-pyrimidin-2-yl)-phenyl]-2-(4'-difluoromethoxyphenyl)-ethane Example 17a 4-(trans-4-Propylcyclohexyl)-phenyl 4-difluoromethoxybenzoate 4-Difluoromethoxybenzoic acid (available by etherification of the phenolic OH group of p-hydroxybenzyl alcohol analogously to Example 1a), followed by oxidation with potassium permanganate) is esterified, as described in Example 5b), with 4-(trans-4-propylcyclohexyl)-phenol by the DCC method. m.p.: 104° C., c.p.: 193.5° C.

The following were prepared analogously:
4-(trans-4-methylcyclohexyl)-phenyl 4-difluoromethoxybenzoate
4-(trans-4-ethylcyclohexyl)-phenyl 4-difluoromethoxybenzoate
4-(trans-4-butylcyclohexyl)-phenyl 4-difluoromethoxybenzoate
4-(trans-4-pentylcyclohexyl)-phenyl 4-difluoromethoxybenzoate
4-(trans-4-hexylcyclohexyl)-phenyl 4-difluoromethoxybenzoate
4-(trans-4-heptylcyclohexyl)-phenyl 4-difluoromethoxybenzoate
4-(trans-4-nonylcyclohexyl)-phenyl 4-difluoromethoxybenzoate
4-(trans-4-octylcyclohexyl)-phenyl 4-difluoromethoxybenzoate
4-(trans-4-decylcyclohexyl)-phenyl 4-difluoromethoxybenzoate
4-methylphenyl 4-difluoromethoxybenzoate
4-ethylphenyl 4-difluoromethoxybenzoate
4-propylphenyl 4-difluoromethoxybenzoate
4-butylphenyl 4-difluoromethoxybenzoate
4-pentylphenyl 4-difluoromethoxybenzoate
4-hexylphenyl 4-difluoromethoxybenzoate
4-heptylphenyl 4-difluoromethoxybenzoate
4-octylphenyl 4-difluoromethoxybenzoate
4-nonylphenyl 4-difluoromethoxybenzoate
4-decylphenyl 4-difluoromethoxybenzoate
4'-methylbiphenyl-4-yl 4-difluoromethoxybenzoate
4'-ethylbiphenyl-4-yl 4-difluoromethoxybenzoate
4'-propylbiphenyl-4-yl 4-difluoromethoxybenzoate
4'-butylbiphenyl-4-yl 4-difluoromethoxybenzoate
4'-pentylbiphenyl-4-yl 4-difluoromethoxybenzoate
4'-hexylbiphenyl-4-yl 4-difluoromethoxybenzoate
4'-heptylbiphenyl-4-yl 4-difluoromethoxybenzoate
4'-octylbiphenyl-4-yl 4-difluoromethoxybenzoate
4'-nonylbiphenyl-4-yl 4-difluoromethoxybenzoate
4'-decylbiphenyl-4-yl 4-difluoromethoxybenzoate Using 4-difluoromethylthiobenzoic acid (available from p-toluenesulfonic acid by oxidation to give the carboxylic acid, esterification, conversion to the sulfonyl chloride, reduction, using zinc/hydrochloric acid, etherification analogously to Example 1 and liberation of the acid), the following are obtained analogously:
4-(trans-4-methylcyclohexyl)-phenyl 4-difluoromethylthiobenzoate
4-(trans-4-ethylcyclohexyl)-phenyl 4-difluoromethylthiobenzoate
4-(trans-4-propylcyclohexyl)-phenyl 4-difluoromethylthiobenzoate
4-(trans-4-butylcyclohexyl)-phenyl 4-difluoromethylthiobenzoate
4-(trans-4-pentylcyclohexyl)-phenyl 4-difluoromethylthiobenzoate
4-(trans-4-hexylcyclohexyl)-phenyl 4-difluoromethylthiobenzoate
4-(trans-4-heptylcyclohexyl)-phenyl 4-difluoromethylthiobenzoate
4-(trans-4-octylcyclohexyl)-phenyl 4-difluoromethylthiobenzoate
4-(trans-4-nonylcyclohexyl)-phenyl 4-difluoromethylthiobenzoate
4-(trans-4-decylcyclohexyl)-phenyl 4-difluoromethylthiobenzoate The following examples refer to liquid-crystalline phases according to the invention.

Example A1

A liquid-crystalline phase consisting of:
10% of p-trans-4-propylcyclohexylbenzonitrile
10% of p-trans-4-butylcyclohexylbenzonitrile
10% of p-trans-4-pentylcyclohexylbenzonitrile
20% of difluoromethoxy-4-(trans-4-pentylcyclohexyl)-benzene
10% of trans-1-p-ethoxyphenyl-4-propylcyclohexane
8% of trans-1-p-butoxyphenyl-4-propylcyclohexane
5% of 4'-p-propylphenyl trans-4-(trans-4-propylcyclohexyl)-cyclohexanecarboxylate
5% of 4'-p-pentylphenyl trans-4-(trans-4-propylcyclohexyl)-cyclohexanecarboxylate
5% of 4'-p-propylphenyl trans-4-(trans-4-butylcyclohexyl)-cyclohexanecarboxylate
5% of 4'-p-pentylphenyl trans-4-(trans-4-butylcyclohexyl)-cyclohexanecarboxylate 4% of 4-(trans-4-propylcyclohexyl)-2'-fluoro-4'-(trans-4-propylcyclohexyl)-biphenyl
4% of 2-fluoro-4-(trans-4-pentylcyclohexyl)-4'-(trans-4-propylcyclohexyl)biphenyl and
4% of 4-(trans-4-pentylcyclohexyl)-2'-fluoro-4'-(trans-4-pentylcyclohexyl)-biphenyl
has a melting point of −18.8° C., a clear point of 78° C. and a viscosity of 16 mm$^2$/s at 20° C.

Example B1

A liquid-crystalline phase consisting of
15% of difluoromethoxy-4-(trans-4-propylcyclohexyl)-benzene
17% of difluoromethoxy-4-(trans-4-pentylcyclohexyl)-benzene
13% of difluoromethoxy-4-(trans-4-heptylcyclohexyl)-benzene
10% of trans-1-p-methoxyphenyl-4-propylcyclohexane
10% of trans-1-p-ethoxyphenyl-4-propylcyclohexane
5% of trans-1-p-butoxyphenyl-4-propylcyclohexane
5% of 4-(trans-4-propylcyclohexyl)-2'-fluoro-4'-(trans-4-propylcyclohexyl)-biphenyl
5% of 2-fluoro-4-(trans-4-pentylyclohexyl)-4'-(trans- 4-propylcyclohexyl)-biphenyl
5% of 4-(trans-4-pentylcyclohexyl)-2'-fluoro-4'-(trans-4-pentylcyclohexyl)-biphenyl
5% of 4,4'-bis-(trans-4-propylcyclohexyl)-biphenyl
5% of 4-(trans-4-pentylcyclohexyl)-4'-(trans-4-propylcyclohexyl)-biphenyl and
5% of 4,4'-bis-(trans-4-pentylcyclohexyl)-biphenyl
has a melting point of −20.8° C., a clear point of 72° C. and a viscosity of 12 mm$^2$/s at 20° C.

Example C1

A liquid-crystalline phase consisting of
16% of p-trans-4-propylcyclohexyl-benzonitrile
4% of p-trans-4-pentylcyclohexyl-benzonitrile
18% of 1-(3,3-difluoropropyl)-4-(trans-4-propylcyclohexyl)-benzene
10% of trans-1-p-methoxyphenyl-4-propylcyclohexane
10% of trans-1-p-ethoxyphenyl-4-propylcyclohexane
11% of 4-ethyl-4'-(trans-4-propylcyclohexyl)-biphenyl
11% of 4-ethyl-4'-(trans-4-pentylcyclohexyl)-biphenyl
3% of 4-(trans-4-propycyclohexyl)-2'-fluoro-4'-(trans-4-propylcyclohexyl)-biphenyl
4% of 2-fluoro-4-(trans-4-pentylcyclohexyl)-4'-(trans-4-propylcyclohexyl)-biphenyl
3% of 4-(trans-4-pentylcyclohexyl)-2'-fluoro-4'-(trans-4-pentylcyclohexyl)-biphenyl
3% of 4,4'-bis-(trans-4-propylcyclohexyl)-biphenyl
4% of 4-(trans-4-pentylcyclohexyl)-4'-(trans-4-propylcyclohexyl)-biphenyl and
3% of 4,4'-bis-(trans-4-pentylcyclohexyl)-biphenyl
has a melting point of −10.3° C., a clear point of 91° C. and a viscosity of 17 mm$^2$/s at 20° C.

Example D1

A liquid-crystalline phase consisting of
24% of p-trans-4-propylcycloyhexyl-benzonitrile
36% of p-trans-4-pentylcyclohexyl-benzonitrile
25% of p-trans-4-heptylcyclohexyl-benzonitrile
15% of 4-cyano-4'-(trans-4-pentylcyclohexyl)-biphenyl
has a clear point of 71° C., a Δn of 0.140 and a viscosity of 28.

This phase is mixed with 10% of one of the following compounds I according to the invention. The values of this phase according to the invention obtained are summarized in Table 1 below.

Compounds I
1 4-difluoromethoxy-4'-octoxy-biphenyl
2 difluoromethoxy-4-(trans-4-propylcyclohexyl)-benzene
3 difluoromethoxy-4-(trans-4-pentylcyclohexyl)-benzene
4 4-[2-(4-difluoromethoxyphenyl)-ethyl]-4'-pentyl-trans,trans-bicyclohexyl
5 difluoromethoxy-4-(5-heptyl-1,3-pyrimidin-2-yl)-benzene
6 4-difluoromethoxy-4'-(trans-4-pentylcyclohexyl)-biphenyl

TABLE 1

| I | c.p. [°C.] | Δn | Viscosity |
|---|---|---|---|
| 1 | 65.4 | 0.1349 | 26.8 |
| 2 | 60.2 | 0.1291 | 23.8 |
| 3 | 61.8 | 0.1313 | 24.5 |
| 4 | 76.7 | 0.1353 | 27.4 |
| 5 | 63.7 | 0.1368 | 26.7 |
| 6 | 76.1 | 0.1411 | 28.2 |

Example E1

A liquid-crystalline phase consisting of 22% of trans-1-p-ethylphenyl-4-propylcyclohexane
20% of trans-1-p-methoxyphenyl-4-propylcyclohexane
15% of trans-1-p-ethoxyphenyl-4-propylcyclohexane
19% of 4-ethyl-4'-(trans-4-propylcyclohexyl)-biphenyl
14% of 4-ethyl-4'-(trans-4-pentylcyclohexyl)-biphenyl
5% of 4-(trans-4-propylcyclohexyl)-4'-(trans-4-propylcyclohexyl)-biphenyl
5% of 4-(trans-4-pentylcyclohexyl)-4'-(trans-4-propylcyclohexyl)-biphenyl
has a clear point of 72° C., a Δn of 0.1131 and a viscosity of 11.

This phase is mixed with 10% of one of the following compounds I according to the invention. The values of this phase according to the invention obtained are summarized in Table 2 below.

Compounds I
7 4-difluoromethoxyphenyl trans-4-pentyl-cyclohexanecarboxylate
8 4-difluoromethoxyphenyl 4'-pentyl-trans,trans-bicyclohexane-4-carboxylate

TABLE 2

| I | c.p. [°C.] | Δn | Viscosity |
|---|---|---|---|
| 7 | 67.8 | 0.1080 | 11.9 |
| 8 | 82.7 | 0.1108 | 12.6 |

In the following examples, the structures of the liquid crystal compounds are indicated by acronyms, the transformation into chemical formulae taking place according to the following Tables A and B. All radicals $C_nH_{2n+1}$ and $C_mH_{2m+1}$ are straight-chain alkyl radical shaving n or m C atoms. The coding according to Table B is self-evident. In Table A, only the acronym for the basic structure is indicated. In the individual case, a code for the substituents $R^1$, $R^2$, $L^1$ and $L^2$ follows separately from the acronym for the basic structure.

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| nT | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nOmFF | $C_nH_{2n+1}$ | $OC_mH_{2m+1}$ | F | F |
| nmF | $C_nH_{2n+1}$ | $C_mH_{2m+1}$ | F | H |
| nCF$_3$ | $C_nH_{2n+1}$ | $CF_3$ | H | H |
| nOCF$_3$ | $C_nH_{2n+1}$ | $OCF_3$ | H | H |
| nOCF$_2$ | $C_nH_{2n+1}$ | $OCHF_2$ | H | H |
| nS | $C_nH_{2n+1}$ | NCS | H | H |
| rVsN | $^1C_rH_{2r+1}-CH=CH-C_sH_{2s}-$ | CN | H | H |
| rEsN | $C_rH_{2r+1}-O-C_sH_{2s}-$ | CN | H | H |
| nNF | $C_nH_{2n+1}$ | CN | F | H |
| nAm | $C_nH_{2n+1}$ | $COOC_mH_{2m+1}$ | H | H |

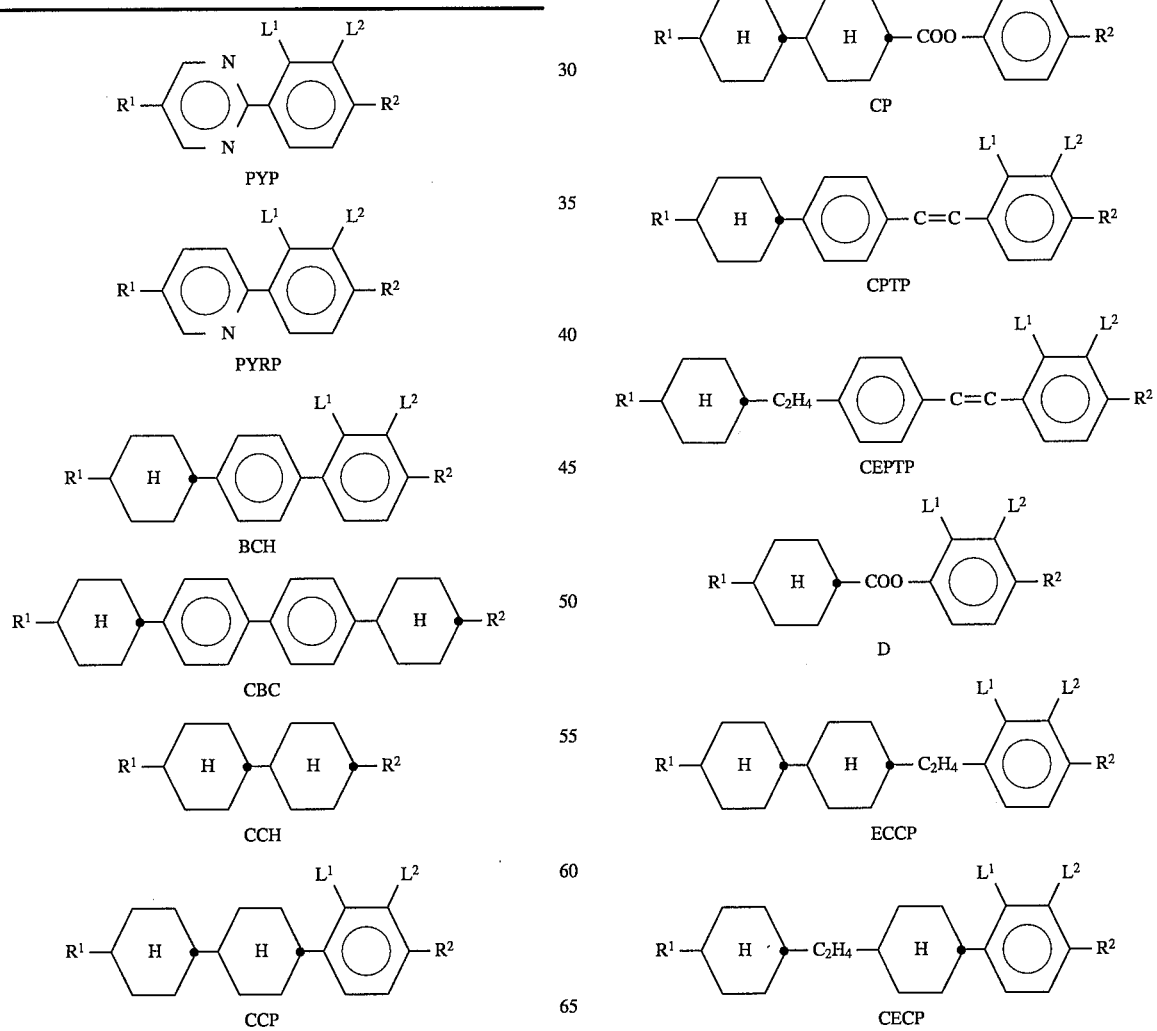

TABLE A-continued

EPCH: $R^1$-H-$C_2H_4$-(ring with $L^1$, $L^2$)-$R^2$

HP: $R^1$-H-(ring)-COO-(ring with $L^1$, $L^2$)-$R^2$

ME: $R^1$-(ring)-COO-(ring with $L^1$, $L^2$)-$R^2$

PCH: $R^1$-H-(ring with $L^1$, $L^2$)-$R^2$

PDX: $R^1$-(dioxane ring)-(ring with $L^1$, $L^2$)-$R^2$

PTP: $R^1$-(ring)-C=C-(ring with $L^1$, $L^2$)-$R^2$

BECH: $R^1$-H-$C_2H_4$-(ring)-(ring with $L^1$, $L^2$)-$R^2$

EBCH: $R^1$-H-(ring)-$C_2H_4$-(ring with $L^1$, $L^2$)-$R^2$

CPC: $R^1$-H-(ring)-H-$R^2$

TABLE B

T15: $C_5H_{11}$-(ring)-(ring)-(ring)-CN

K3n: $C_nH_{2n+1}$-(ring)-(ring)-CN

M3n: $C_nH_{2n+1}$-O-(ring)-(ring)-CN

BCH-n.Fm: $C_nH_{2n+1}$-H-(ring)-(ring)-$C_mH_{2m+1}$, with F

Inm: $C_nH_{2n+1}$-H-$C_2H_4$-(ring)-(ring)-$C_mH_{2m+1}$, with F

C-nm: $C_nH_{2n+1}$-H-H-OOC-$C_mH_{2m+1}$

C15: $C_2H_5$-CH(CH$_3$)*-CH$_2$-O-(ring)-(ring)-CN

CB15: $C_2H_5$-CH(CH$_3$)*-CH$_2$-(ring)-(ring)-CN

CBC-nmF: $C_nH_{2n+1}$-H-(ring)-(ring)-H-$C_mH_{2m+1}$, with F

CCN-nm: $C_nH_{n+1}$-H-H(CN)-$C_mH_{2m+1}$

CCPC-nm: $C_nH_{2n+1}$-H-H-COO-(ring)-H-$C_mH_{2m+1}$

CH-nm: $C_nH_{2n+1}$-H-H-COO-H-$C_mH_{2m+1}$

HD-nm: $C_nH_{2n+1}$-H-(ring)-OOC-H-$C_mH_{2m+1}$

HH-nm: $C_nH_{2n+1}$-H-(ring)-COO-H-$C_mH_{2m+1}$

NCB-nm: $C_nH_{2n+1}$-(ring)-(ring)-H(CN)-$C_mH_{2m+1}$

TABLE B-continued $C_nH_{2n+1}$—⟨H⟩—COO—⟨H⟩—$C_mH_{2m+1}$

OS-nm $C_2H_5$—⟨H⟩—COO—⟨O⟩—⟨O⟩—CN

CHE $C_nH_{2n+1}$—⟨H⟩—$C_2H_4$—⟨O⟩—⟨O⟩—⟨H⟩—$C_mH_{2m+1}$

ECBC-nm $C_nH_{2n+1}$—⟨H⟩—$C_2H_4$—⟨H⟩—$C_mH_{2m+1}$

ECCH-nm $C_nH_{2n+1}$—⟨H⟩—⟨H⟩—$CH_2O$—$C_mH_{2m+1}$

CCH-n1Em $C_nH_{2n+1}$—⟨O⟩—⟨O⟩(F)—⟨O⟩—CN

T-nFn $C_nH_{2n+1}$—⟨H⟩—$C_2H_4$—⟨H⟩—$C_mH_{2m+1}$

ECCH-nm $C_nH_{2n+1}$—⟨H⟩—⟨H⟩—$CH_2O$—$C_mH_{2m+1}$

CCH-n1Em $C_nH_{2n+1}$—⟨O⟩—⟨O⟩(F)—⟨O⟩—CN

T-nFN $C_nH_{2n+1}$—⟨H⟩—⟨H⟩—$CH_2CH_2CF_3$

CCH-n2CF3

TABLE B-continued $C_nH_{2n+1}$—⟨H⟩—⟨H⟩—⟨O⟩(F,F,F)

CCP-nF.F.F.

$C_nH_{2n+1}$—⟨H⟩—⟨O⟩—⟨O⟩(F,F,F)

BCH-nF.F.F

Example 1b 0.1 mole of n-BuLi (1.5M in hexane) is added dropwise at about −65° C. to a solution of 0.1 mol of 1-trans-4-(trans 4-n-propylcyclohexyl) cyclohexyl-2-(3,5-difluorophenyl)-ethane (prepared according to scheme 1) and 0.1 mol of TMEDA in 300 ml of THF. Stirring at this temperature is continued for another 30 minutes, and 0.1 mol of $B(OCH_3)_3$ is added to this mixture at −60° to −70° C. Stirring is continued for another half hour. 0.3 mol of $H_2O_2$ (30%) is added dropwise, during which the temperature should not exceed +40° C. Extractive work-up gives the phenol, which can be purified by crystallization or distillation.

The $OCHF_2$ derivative is obtained from this phenol by introducing $CHClF_2$ into the THF solution of the phenolate. Extractive work-up and conventional purification gives 1-[trans-4-(trans-4-n-propylcyclohexyl)cyclohexyl]-2-(4-difluoromethoxy- 3,5-difluorophenyl)ethane.

Examples 2b to 23b

The following compounds according to the invention are obtained analogously from the corresponding precursors of the formula II":

| R | $(A^1—Z^1)_m—A^2—Z^2—$ | Q—Y | L |
|---|---|---|---|
| (2) Ethyl | ⟨H⟩—⟨H⟩—$CH_2CH_2$— | $OCHF_2$ | F |
| (3) n-Butyl | ⟨H⟩—⟨H⟩—$CH_2CH_2$— | $OCHF_2$ | F |
| (4) n-Pentyl | ⟨H⟩—⟨H⟩—$CH_2CH_2$— | $OCHF_2$ | F |
| (5) n-Heptyl | ⟨H⟩—⟨H⟩—$CH_2CH_2$— | $OCHF_2$ | F |

-continued
| R | $(A^1-Z^1)_m-A^2-Z^2-$ | Q—Y | L |
|---|---|---|---|
| (6) Ethyl | 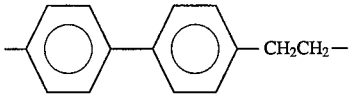 | OCHF$_2$ | F |
| (7) Methoxy | 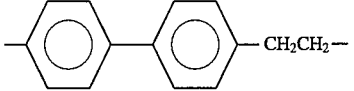 | OCHF$_2$ | F |
| (8) Ethoxy | 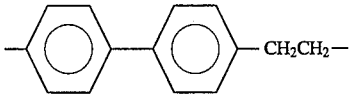 | OCHF$_2$ | F |
| (9) n-Propyl | 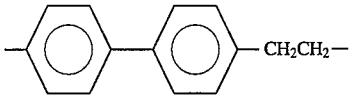 | OCHF$_2$ | F |
| (10) n-Pentyl | 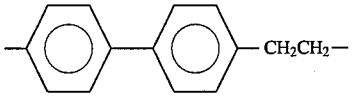 | OCHF$_2$ | F |
| (11) Methoxymethyl | 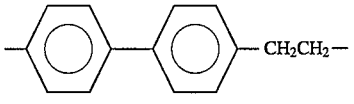 | OCHF$_2$ | F |
| (12) n-Propyl | 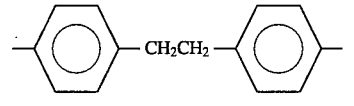 | OCHF$_2$ | F |
| (13) n-Pentyl | 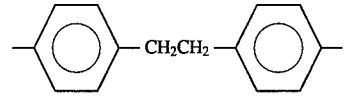 | OCHF$_2$ | F |
| (14) n-Propyl | 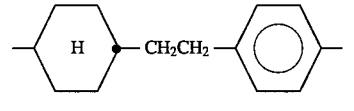 | OCHF$_2$ | F |
| (15) n-Pentyl | 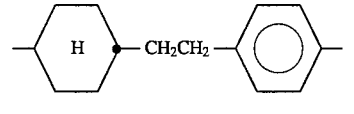 | OCHF$_2$ | F |
| (16) n-Propyl | 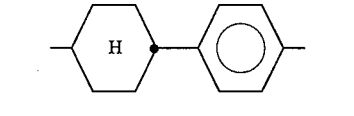 | OCHF$_2$ | F |
| (17) n-Butyl | 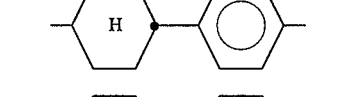 | OCHF$_2$ | F |
| (18) n-Pentyl | 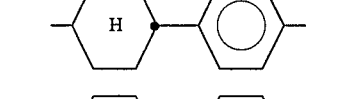 | OCHF$_2$ | F |
| (19) n-Propyl | 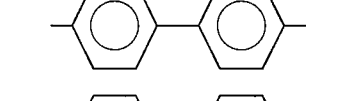 | OCHF$_2$ | F |
| (20) n-Pentyl | 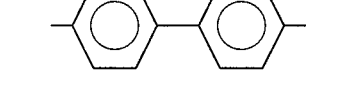 | OCHF$_2$ | F |

| R | $(A^1-Z^1)_m-A^2-Z^2-$ | Q—Y | L |
|---|---|---|---|
| (21) n-Propyl | —[H]—[H]— | OCHF$_2$ | F, C61N128I |
| (22) n-Butyl | —[H]—[H]— | OCHF$_2$ | F |
| (23) n-Pentyl | —[H]—[H]— | OCHF$_2$ | F |

Example 24b

2mol of anhydrous hydrofluoric acid is poured into an autoclave which has been cooled to 0° C. A mixture of 0.18 mol of carbon tetrachloride and 0.06 mol of 1-[trans-4-(trans-4-n-propylhexyl)cyclohexyl]-2-(4-hydroxy- 3,5-difluorophenyl)-ethane (Example 1b) is then added. The mixture is stirred at 150° for about 8 hours, cooled, poured into ice water, and the autoclave is subsequently washed out with ether. The two phases are combined, stirred for about 30 minutes, separated, and the ether solution is washed with 5% KOH solution until it remains alkaline. The organic phase is dried, filtered, evaporated, and the residue is purified to give 1-[trans-4-(trans-4-n-propylcyclohexyl)cyclohexyl]-2-(4-trifluoromethoxy- 3,5-difluorophenyl)-ethane.

Examples 25b to 45b

The following compounds are obtained analogously from the corresponding precursors of the formula II":

| R | $(A^1-Z^1)_m-A^2-Z^2-$ | Q—Y | L |
|---|---|---|---|
| (25) n-Butyl | —[H]—[H]—CH$_2$CH$_2$— | OCF$_3$ | F |
| (26) n-Pentyl | —[H]—[H]—CH$_2$CH$_2$— | OCF$_3$ | F |
| (27) n-Heptyl | —[H]—[H]—CH$_2$CH$_2$— | OCF$_3$ | F |
| (28) Ethyl | —[○]—[○]—CH$_2$CH$_2$— | OCF$_3$ | F |
| (29) Methoxy | —[○]—[○]—CH$_2$CH$_2$— | OCF$_3$ | F |
| (30) Ethoxy | —[○]—[○]—CH$_2$CH$_2$— | OCF$_3$ | F |
| (31) n-Propyl | —[○]—[○]—CH$_2$CH$_2$— | OCF$_3$ | F |

| R | $(A^1-Z^1)_m-A^2-Z^2-$ | Q—Y | L |
|---|---|---|---|
| (32) n-Pentyl | —[phenyl]—[phenyl]—CH₂CH₂— | OCF₃ | F |
| (33) Methoxymethyl | —[phenyl]—[phenyl]—CH₂CH₂— | OCF₃ | F |
| (34) n-Propyl | —[phenyl]—CH₂CH₂—[phenyl]— | OCF₃ | F |
| (35) n-Pentyl | —[phenyl]—CH₂CH₂—[phenyl]— | OCF₃ | F |
| (36) n-Propyl | —[cyclohexyl]—CH₂CH₂—[phenyl]— | OCF₃ | F |
| (37) n-Pentyl | —[cyclohexyl]—CH₂CH₂—[phenyl]— | OCF₃ | F |
| (38) n-Propyl | —[cyclohexyl]—[phenyl]— | OCF₃ | F |
| (39) n-Butyl | —[cyclohexyl]—[phenyl]— | OCF₃ | F |
| (40) n-Pentyl | —[cyclohexyl]—[phenyl]— | OCF₃ | F |
| (41) n-Propyl | —[phenyl]—[phenyl]— | OCF₃ | F |
| (42) n-Pentyl | —[phenyl]—[phenyl]— | OCF₃ | F |
| (43) n-Propyl | —[cyclohexyl]—[cyclohexyl]— | OCF₃ | F |
| (44) n-Butyl | —[cyclohexyl]—[cyclohexyl]— | OCF₃ | F |
| (45) n-Pentyl | —[cyclohexyl]—[cyclohexyl]— | OCF₃ | F |

Example 46b 31.6 g of 2-fluoro-4-[trans-4-(trans-4-n-propylcyclohexyl)cyclohexyl]phenol (prepared by hydrogenation from the corresponding benzyl ether, which had been obtained by cross-coupling of bis[trans-4-(trans-4-n-propylcyclohexyl)cyclohexyl]zinc with 4-bromo-2-fluorobenzyl phenyl ether) and 49.3 g of carbon tetrachloride are initially introduced into a Hastelloy autoclave and cooled with dry ice/acetone.

After the autoclave has been evacuated, 66.7 g of HF and 1.67 g of BF$_3$ are added. After stirring at 150° C. for 8 hours, the mixture is allowed to cool to room temperature, and the HF is removed by means of an aspirator. The residue is taken up in methylene chloride, and NaF is added to separate off any remaining HF. The mixture is filtered, the filtrate is evaporated, and the residue is purified by chromatography over silica gel and repeated crystallization from hexane and ethanol to give 2-fluoro- 4-[trans-4-(trans-4-n-propylcyclohexyl)cyclohexyl]trifluoromethoxybenzene.

Examples 47b to 68h

The following compounds are obtained analogously from the corresponding phenols:

| R | $(A^1-Z^1)_m-A^2-Z^2-$ | Q—Y | L |
|---|---|---|---|
| (47) n-Propyl | 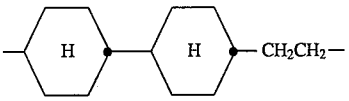 | OCF$_3$ | H |
| (48) n-Pentyl | 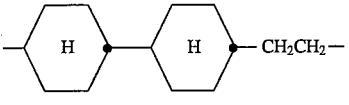 | OCF$_3$ | H |
| (49) n-Heptyl | 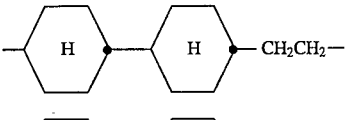 | OCF$_3$ | H |
| (50) Ethyl |  | OCF$_3$ | H |
| (51) Methoxy |  | OCF$_3$ | H |
| (52) Ethoxy |  | OCF$_3$ | H |
| (53) n-Propyl |  | OCF$_3$ | H |
| (54) n-Pentyl | 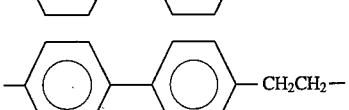 | OCF$_3$ | H |
| (55) Methoxymethyl | 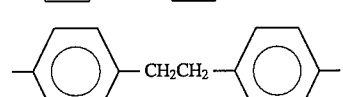 | OCF$_3$ | H |
| (56) n-Propyl | 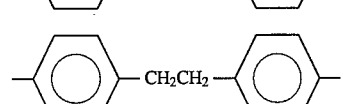 | OCF$_3$ | H |
| (57) n-Pentyl | 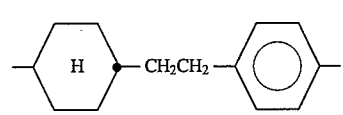 | OCF$_3$ | H |
| (58) n-Propyl |  | OCF$_3$ | H |

-continued

| R | $(A^1-Z^1)_m-A^2-Z^2-$ | Q—Y | L |
|---|---|---|---|
| (59) n-Pentyl | —[Cy(H)]—CH₂CH₂—[Ph]— | OCF₃ | H |
| (60) n-Propyl | —[Cy(H)]—[Ph]— | OCF₃ | H |
| (61) n-Butyl | —[Cy(H)]—[Ph]— | OCF₃ | H |
| (62) n-Pentyl | —[Cy(H)]—[Ph]— | OCF₃ | H |
| (63) n-Propyl | —[Ph]—[Ph]— | OCF₃ | H |
| (64) n-Pentyl | —[Ph]—[Ph]— | OCF₃ | H |
| (65) Ethyl | —[Cy(H)]—[Cy(H)]— | OCF₃ | H |
| (66) n-Propyl | —[Cy(H)]—[Cy(H)]— | OCF₃ | H |
| (67) n-Butyl | —[Cy(H)]—[Cy(H)]— | OCF₃ | H |
| (68) n-Pentyl | —[Cy(H)]—[Cy(H)]— | OCF₃ | H |

Examples 69b to 91b

The following compounds are obtained analogously to Example 1 from the corresponding phenols:

| R | $(A^1-Z^1)_m-A^2-Z^2-$ | Q—Y | L |
|---|---|---|---|
| (69) Ethyl | 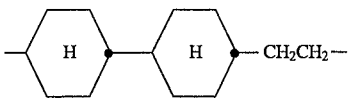 | OCHF$_2$ | H |
| (70) n-Butyl | 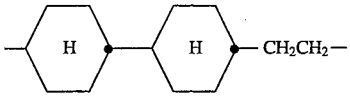 | OCHF$_2$ | H |
| (71) n-Pentyl | 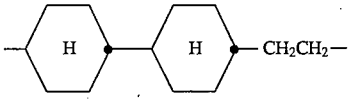 | OCHF$_2$ | H |
| (72) n-Heptyl | 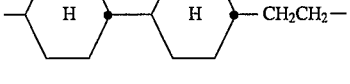 | OCHF$_2$ | H |
| (73) Ethyl |  | OCHF$_2$ | H |
| (74) Methoxy |  | OCHF$_2$ | H |
| (75) Ethoxy |  | OCHF$_2$ | H |
| (76) n-Propyl | 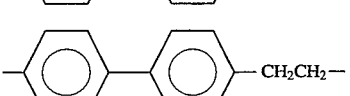 | OCHF$_2$ | H |
| (77) n-Pentyl | 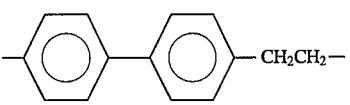 | OCHF$_2$ | H |
| (78) Methoxymethyl | 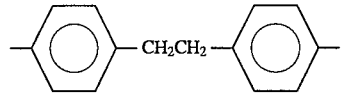 | OCHF$_2$ | H |
| (79) n-Propyl | 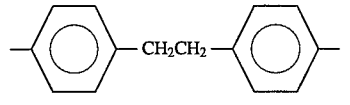 | OCHF$_2$ | H |
| (80) n-Pentyl | 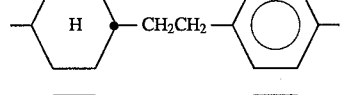 | OCHF$_2$ | H |
| (81) n-Propyl | 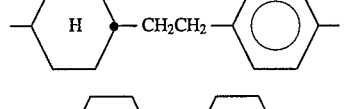 | OCHF$_2$ | H |
| (82) n-Pentyl |  | OCHF$_2$ | H |
| (83) n-Propyl |  | OCHF$_2$ | H, C50N121I |

-continued
| R | $(A^1-Z^1)_m-A^2-Z^2-$ | Q—Y | L |
|---|---|---|---|
| (84) n-Butyl | 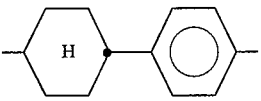 | OCHF$_2$ | H |
| (85) n-Pentyl | 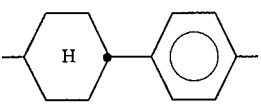 | OCHF$_2$ | H, C38N123I |
| (86) n-Propyl | 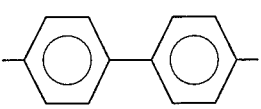 | OCHF$_2$ | H |
| (87) n-Pentyl | 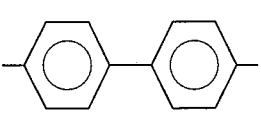 | OCHF$_2$ | H |
| (88) Ethyl | 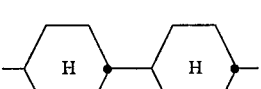 | OCHF$_2$ | H, C15N108I |
| (89) n-Propyl | 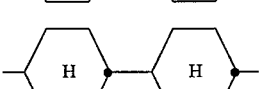 | OCHF$_2$ | H, C33N144I |
| (90) n-Butyl | 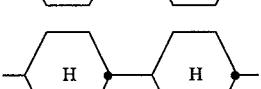 | OCHF$_2$ | H, C37N143I |
| (91) n-Pentyl | 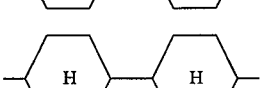 | OCHF$_2$ | H, C37S$_B$(21)N149I |
| (92) Ethyl | 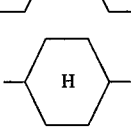 | OCHF$_2$ | H |
| (93) n-Propyl | 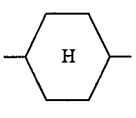 | OCHF$_2$ | H |
| (94) n-Butyl | 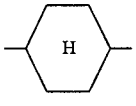 | OCHF$_2$ | H |
| (95) n-Pentyl | 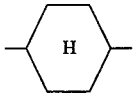 | OCHF$_2$ | H, C9I |
| (96) n-Heptyl | 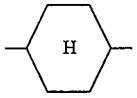 | OCHF$_2$ | H, C7N(-28)I |
| (97) n-Propyl |  | OCHF$_2$ | H |

-continued

| R | (A¹—Z¹)ₘ—A²—Z²— | Q—Y | L |
|---|---|---|---|
| (98) n-Pentyl | phenyl | OCHF₂ | H |

Example 99b 0.1 mol of n-BuLi (1.5M in hexane) is added dropwise at about −65° to a solution of 0.1 mol of 1-[trans-4-(trans-4-n-propylcyclohexyl)cyclohexyl]-2-(3,5-difluorophenyl)-ethane (prepared according to scheme 3) and 0.1 mol of TMEDA in 300 ml of THF. Stirring at this temperature is continued for another 30 minutes, and 0.2 mol of N-chlorosuccinimide in 70 ml of THF are then slowly added. After the addition is completed, the mixture is allowed to warm to −20° and hydrolyzed with H₂O. Diethyl ether is added until the product is completely dissolved. Extractive work-up and purification by chromatography and crystallization gives 1-[trans-4-(trans-4-n-propylcyclohexyl)cyclohexyl]-2-(4-chloro-3,5-difluorophenyl)ethane, C 88 N 129 I.

Examples 100b to 143b

The following compounds according to the invention are obtained analogously from the corresponding precursors of the formula II″:

| R | (A¹—Z¹)ₘ—A²—Z²— | Q—Y |
|---|---|---|
| (100) Ethyl | trans,trans-dicyclohexyl-CH₂CH₂— | Cl |
| (101) n-Butyl | trans,trans-dicyclohexyl-CH₂CH₂— | Cl |
| (102) n-Pentyl | trans,trans-dicyclohexyl-CH₂CH₂— | Cl |
| (103) n-Heptyl | trans,trans-dicyclohexyl-CH₂CH₂— | Cl |
| (104) Ethyl | biphenyl-CH₂CH₂— | Cl |
| (105) Methoxy | biphenyl-CH₂CH₂— | Cl |
| (106) Ethoxy | biphenyl-CH₂CH₂— | Cl |
| (107) n-Propyl | biphenyl-CH₂CH₂— | Cl |
| (108) n-Pentyl | biphenyl-CH₂CH₂— | Cl |
| (109) Methoxymethyl | biphenyl-CH₂CH₂— | Cl |

-continued
| R | $(A^1-Z^1)_m-A^2-Z^2-$ | Q—Y |
|---|---|---|
| (110) n-Propyl | 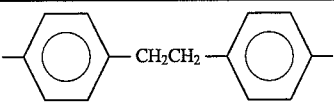 | Cl |
| (111) n-Pentyl | 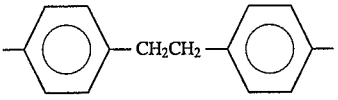 | Cl |
| (112) n-Propyl | 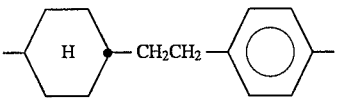 | Cl |
| (113) n-Pentyl | 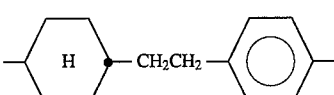 | Cl |
| (114) n-Propyl | 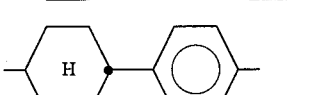 | Cl |
| (115) n-Butyl | 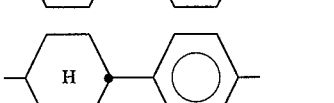 | Cl |
| (116) n-Pentyl | 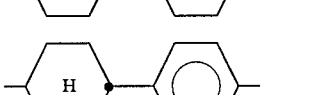 | Cl |
| (117) n-Propyl | 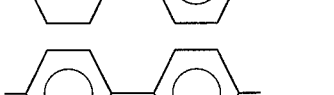 | Cl |
| (118) n-Pentyl | 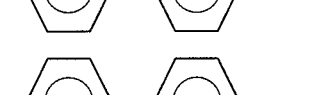 | Cl |
| (119) n-Propyl |  | Cl |
| (120) n-Butyl | 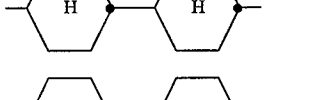 | Cl |
| (121) n-Pentyl | 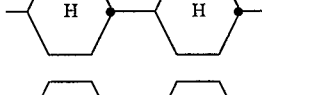 | Cl |
| (122) Ethyl | 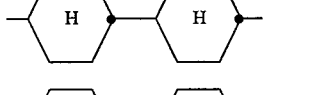 | F |
| (123) n-Butyl | 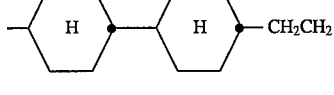 | F |
| (124) n-Pentyl | 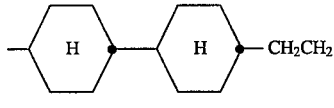 | F |

-continued
| R | $(A^1-Z^1)_m-A^2-Z^2-$ | Q—Y |
|---|---|---|
| (125) n-Heptyl | 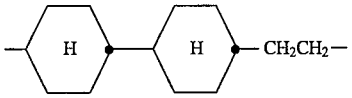 | F |
| (126) Ethyl | 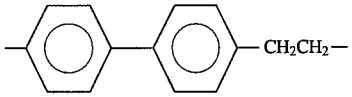 | F |
| (127) Methoxy | 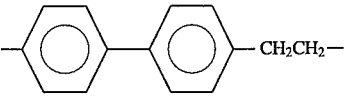 | F |
| (128) Ethoxy | 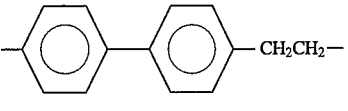 | F |
| (129) n-Propyl | 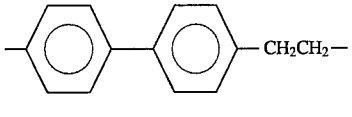 | F |
| (130) n-Pentyl |  | F |
| (131) Methoxymethyl | 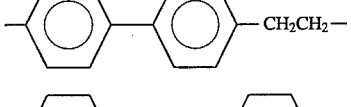 | F |
| (132) n-Propyl | 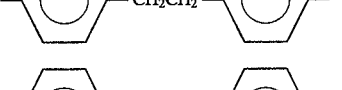 | F |
| (133) n-Pentyl |  | F |
| (134) n-Propyl |  | F |
| (135) n-Pentyl |  | F |
| (136) n-Propyl | 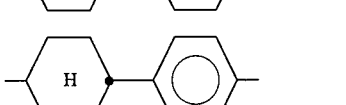 | F, C42N(33)I |
| (137) n-Butyl | 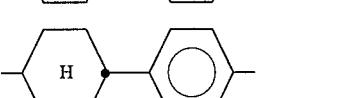 | F |
| (138) n-Pentyl |  | F, C20N42I |

-continued

| R | $(A^1-Z^1)_m-A^2-Z^2-$ | Q—Y |
|---|---|---|
| (139) n-Propyl | phenyl-phenyl | F |
| (140) n-Pentyl | phenyl-phenyl | F |
| (141) n-Propyl | cyclohexyl(H)-cyclohexyl(H) | F, C64N78I |
| (142) n-Butyl | cyclohexyl(H)-cyclohexyl(H) | F |
| (143) n-Pentyl | cyclohexyl(H)-cyclohexyl(H) | F, C86N91I |

Example 144b

A mixture of 0.1 mol of 4-(trans-4-n-pentylcyclohexyl)-2-fluorobenzoic acid and 0.3 mol of $SF_4$ is heated in an autoclave at 130° for 8 hours. The crude product obtained is taken up in pentane and subjected to extractive work-up. Conventional purification by distillation and crystallization gives 4-(trans-4-n-pentylcyclohexyl)-2-fluorobenzo trifluoride.

Example 145b 0.01 mol of TMEDA is added to a solution of 0.01 mol of 4-(trans-4-n-propylcyclohexyl)-4'-trifluoromethylbiphenyl in 10 ml of n-hexane. At 0°–5° C., 0.01 mol of n-BuLi is added, and stirring at RT is continued for another half an hour and at 40° C. for half an hour. The mixture is then cooled to 0° C., 20 ml of THF are added, and the fluorinating agent 1-fluoro-2,4,6-trimethylpyridinium triflate (in THF) is added dropwise at this temperature according to scheme 21. Extractive work-up and, as is customary, chromatography and crystallization give 4-(trans-4-n-propylcyclohexyl)-3'-fluoro-4'-trifluoromethylbiphenyl.

Examples 146b to 175b

The following compounds are obtained from the corresponding precursors analogously to Examples 144b or 145b:

| R | $(A^1-Z^1)_m-A^2-Z^2-$ | Q—Y | L |
|---|---|---|---|
| (146) Ethyl | cyclohexyl(H)-cyclohexyl(H)-$CH_2CH_2$- | $CF_3$ | H |
| (147) n-Butyl | cyclohexyl(H)-cyclohexyl(H)-$CH_2CH_2$- | $CF_3$ | H |
| (148) n-Pentyl | cyclohexyl(H)-cyclohexyl(H)-$CH_2CH_2$- | $CF_3$ | H |
| (149) n-Heptyl | cyclohexyl(H)-cyclohexyl(H)-$CH_2CH_2$- | $CF_3$ | H |
| (150) Ethyl | phenyl-phenyl-$CH_2CH_2$- | $CF_3$ | H |

-continued
| R | $(A^1-Z^1)_m-A^2-Z^2-$ | Q-Y | L |
|---|---|---|---|
| (151) Methoxy | 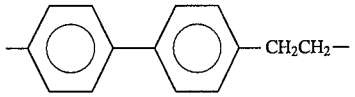 | CF$_3$ | H |
| (152) Ethoxy | 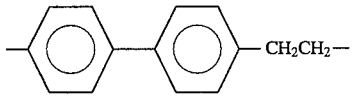 | CF$_3$ | H |
| (153) n-Propyl | 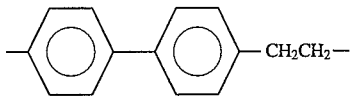 | CF$_3$ | H |
| (154) n-Pentyl | 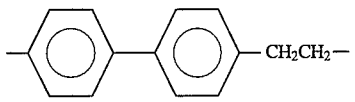 | CF$_3$ | H |
| (155) Methoxymethyl | 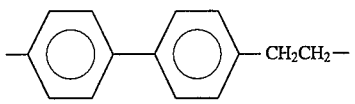 | CF$_3$ | H |
| (156) n-Propyl | 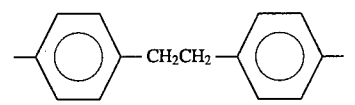 | CF$_3$ | H |
| (157) n-Pentyl | 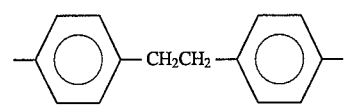 | CF$_3$ | H |
| (158) n-Propyl | 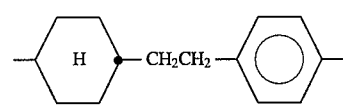 | CF$_3$ | H |
| (159) n-Pentyl | 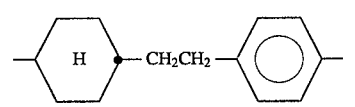 | CF$_3$ | H |
| (160) n-Propyl | 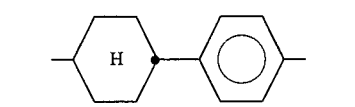 | CF$_3$ | H |
| (161) n-Butyl | 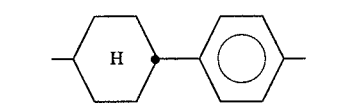 | CF$_3$ | H |
| (162) n-Pentyl | 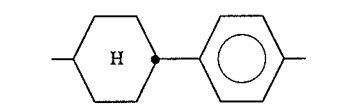 | CF$_3$ | H |
| (163) n-Propyl | 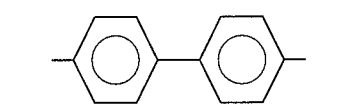 | CF$_3$ | H |
| (164) n-Pentyl | 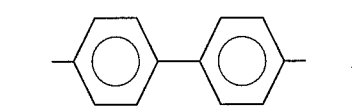 | CF$_3$ | H |
| (165) Ethyl |  | CF$_3$ | H |

-continued

| R | $(A^1-Z^1)_m-A^2-Z^2-$ | Q-Y | L |
|---|---|---|---|
| (166) n-Propyl | H—H— | CF$_3$ | H, C115I Δε = +10.2 |
| (167) n-Butyl | H—H— | CF$_3$ | H |
| (168) n-Pentyl | H—H— | CF$_3$ | H |
| (169) Ethyl | H— | CF$_3$ | H |
| (170) n-Propyl | H— | CF$_3$ | H |
| (171) n-Butyl | H— | CF$_3$ | H |
| (172) n-Pentyl | H— | CF$_3$ | H |
| (173) n-Heptyl | H— | CF$_3$ | H |
| (174) n-Propyl | ⌬— | CF$_3$ | H |
| (175) n-Pentyl | ⌬— | CF$_3$ | H |

Example 176b

A mixture of 0.025 mol of CuI, 0.0125 mol of CF$_3$COONa and 0.0125 mol of 1-[trans-4-(trans-4-n-propylcyclohexyl)cyclohexyl]-2-(4-iodo-3,5-difluorophenyl)-ethane [obtainable according to scheme 15] is heated in 100 ml of N-methylpyrrolidone to 150° with stirring. After one hour, the mixture is subjected as usual to extractive work-up to give, after purification by chromatography, 1-[trans-4-(trans-4-n-propylcyclohexyl)cyclohexyl]-2-(4-trifluoromethyl- 3,5-difluorophenyl)-ethane.

Examples 177b to 206b

The following compounds are obtained from the corresponding 3,5-difluorophenyl compounds analogously to Example 176b:

| R | $(A^1-Z^1)_m-A^2-Z^2-$ | Q-Y | L |
|---|---|---|---|
| (177) Ethyl | H—H—CH$_2$CH$_2$— | CF$_3$ | F |

| R | (A¹—Z¹)ₘ—A²—Z²— | Q—Y | L |
|---|---|---|---|
| (178) n-Butyl | 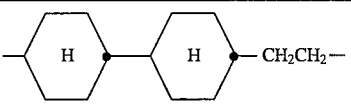 | CF₃ | F |
| (179) n-Pentyl | 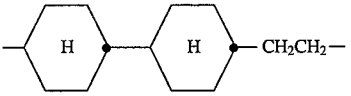 | CF₃ | F |
| (180) n-Heptyl | 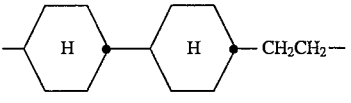 | CF₃ | F |
| (181) Ethyl | 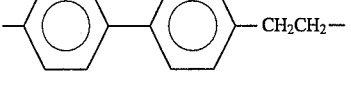 | CF₃ | F |
| (182) Methoxy | 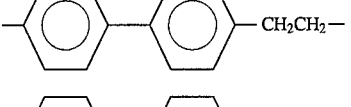 | CF₃ | F |
| (183) Ethoxy | 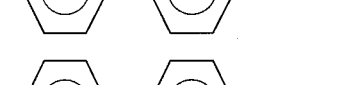 | CF₃ | F |
| (184) n-Propyl |  | CF₃ | F |
| (185) n-Pentyl | 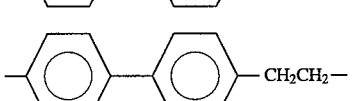 | CF₃ | F |
| (186) Methoxymethyl | 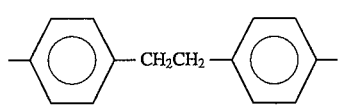 | CF₃ | F |
| (187) n-Propyl | 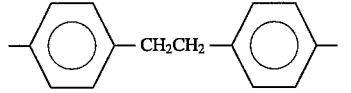 | CF₃ | F |
| (188) n-Pentyl | 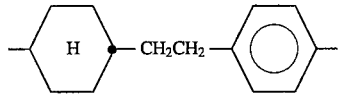 | CF₃ | F |
| (189) n-Propyl | 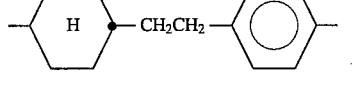 | CF₃ | F |
| (190) n-Pentyl |  | CF₃ | F |
| (191) n-Propyl |  | CF₃ | F |
| (192) n-Butyl |  | CF₃ | F |

-continued

| R | $(A^1-Z^1)_m-A^2-Z^2-$ | Q—Y | L |
|---|---|---|---|
| (193) n-Pentyl | Cy-Ph | $CF_3$ | F |
| (194) n-Propyl | Ph-Ph | $CF_3$ | F |
| (195) n-Pentyl | Ph-Ph | $CF_3$ | F |
| (196) Ethyl | Cy-Cy | $CF_3$ | F |
| (197) n-Propyl | Cy-Cy | $CF_3$ | F, C93I $\Delta\epsilon = +13.1$ |
| (198) n-Butyl | Cy-Cy | $CF_3$ | F |
| (199) n-Pentyl | Cy-Cy | $CF_3$ | F |
| (200) Ethyl | Cy | $CF_3$ | F |
| (201) n-Propyl | Cy | $CF_3$ | F |
| (202) n-Butyl | Cy | $CF_3$ | F |
| (203) n-Pentyl | Cy | $CF_3$ | F |
| (204) n-Heptyl | Cy | $CF_3$ | F |
| (205) n-Propyl | Ph | $CF_3$ | F |
| (206) n-Pentyl | Ph | $CF_3$ | F |

Example 207b

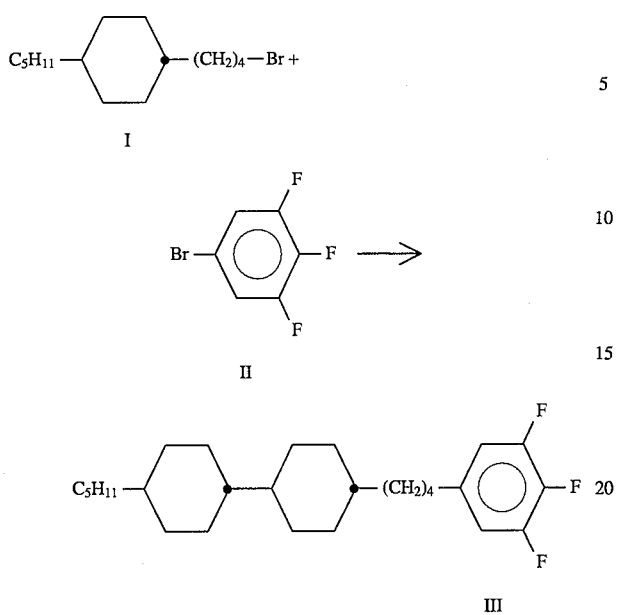

37.1 g of I (0.1 mol) are initially introduced into 150 ml of a solvent mixture of THF/toluene (1:4 volume ratio), then 11.5 g of anhydrous zinc bromide and, after that, 1.4 g of lithium granules are added. The mixture is treated between 0° C. and 10° C. with ultrasound under argon and with stirring for 4 hours in order to convert I into the corresponding dialkyl zinc compound. 21.1 g of II (0.1 mol) and 1.5 g (2 mol %) of 1,1'-bis(diphenylphosphino)ferrocene-palladium(II) dichloride ($PdCl_2$ dppf) are added to the organozinc compound and, after removal of the ultrasonic bath and the cooling, stirred at room temperature for 24 h. The mixture is decomposed with 100 ml of saturated $NH_4Cl$ solution with stirring, the organic phase is separated off, and the aqueous phase is extracted twice with toluene. The combined organic extracts give III after drying, concentrating and chromatographing on silica gel with hexane. (I can be prepared by chain elongation of

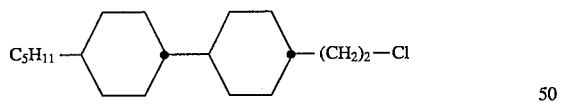

by means of malonic ester). The alkyl bromides listed below can be reacted with II analogously to I:

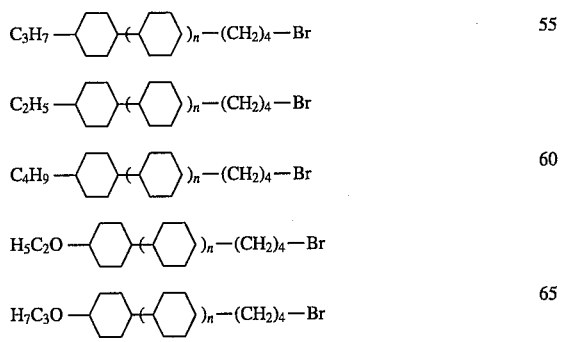

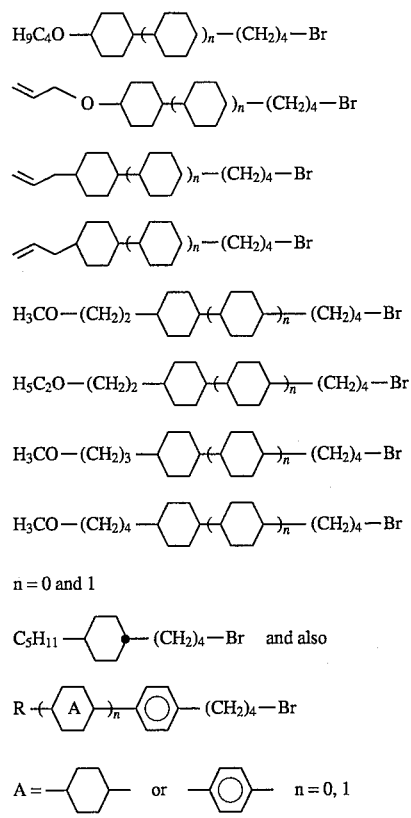

$n = 0$ and $1$

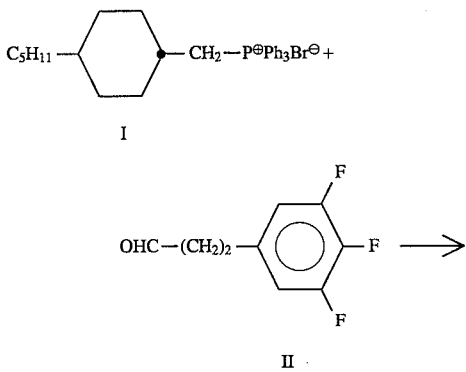

$A = $ cyclohexyl or phenyl   $n = 0, 1$

Example 208b

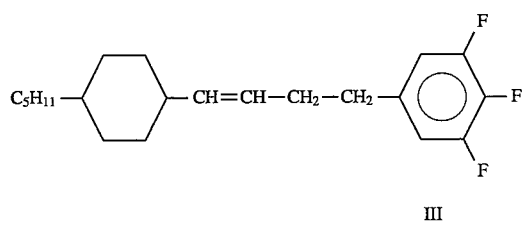

11.5 g of potassium tert-butylate are added in portions between 0° C. and 10° C. to 50.9 g (0.1 mol) of Wittig salt I and 17.2 g of aldehyde II (prepared by Heck reaction of 1-bromotrifluorobenzene with allyl alcohol). After the addition, the mixture is stirred at room temperature for 24 hours, poured into water, neutralized, extracted with toluene, the toluene extract is evaporated after drying and the residue is filtered through silica gel using hexane. 28 g of III are obtained.

Example 209b

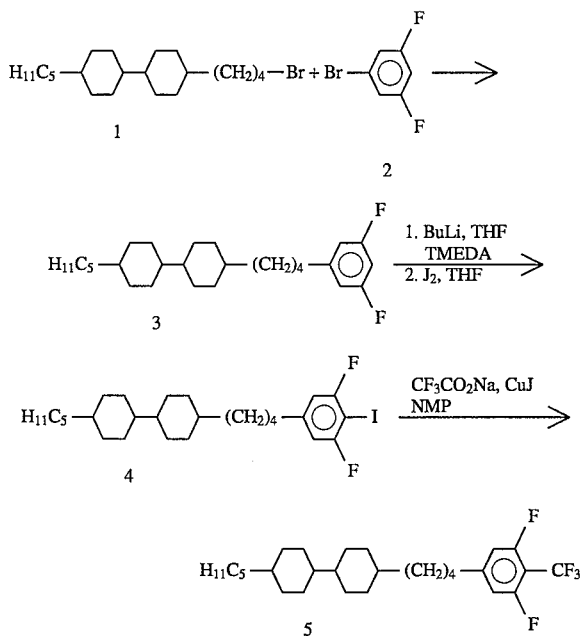

37.1 g (100 mmol) of 1 are converted into 3 by reaction with 2 analogously to Example 207b.

31 ml of n-BuLi (15% in hexane) are added dropwise at −65° to −70° C. to a mixture of 19.0 g (47 mmol) of 3, 7.5 ml of TMEDA (50 mmol) and 150 ml of THF and the mixture is subsequently stirred at −70° C. for 1 hour. A solution of 12.0 g (47 mmol) of iodine in 25 ml of THF is then added dropwise at −65° to −70° C. and the mixture is subsequently stirred at −70° C. for 0.5 h. It is warmed to −30° C., hydrolyzed with 15 ml of water and excess iodine is reduced by addition of 15 ml of sodium hydrogensulphite solution. Customary work-up and recrystallization from hexane gives 23.9 g (45 mmol) of 4. 400 ml of NMP are removed by distillation at 70° C. and 4 mbar from a mixture of 20.2 g (38 mmol) of 4, 4.4 g (76 mmol) of KF, 22.8 g (168 mmol) of sodium trifluoroacetate and 800 ml of NMP. 14.4 g (76 mmol) of dried CuI are then added to the reaction mixture and it is stirred at 160° C. for 5 h. About 300 ml of NMP are then removed by distillation. The mixture is allowed to cool to RT and 300 ml of MTB ether are added. The mixture is washed with water, dried using $Na_2SO_4$, filtered and concentrated to give a residue. Chromatography on silica gel using hexane gives 5.

Example 210b

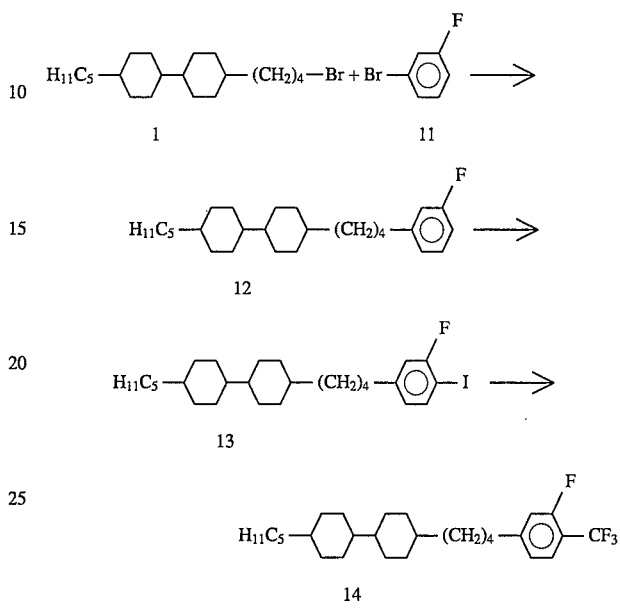

31.1 g (100 mmol) of 1 are converted into 12 by reaction with 11 analogously to Example 207b.

40 ml of n-BuLi are added dropwise at −100° C. to a mixture of 18.2 g (47 mmol) of 12, 7.4 g of potassium tertiary butylate and 110 ml of THF and the mixture is subsequently stirred at −100° C. for 1 h. A solution of 15.9 g of iodine in 60 ml of THF is then added dropwise at −85° to −90° C. The mixture is subsequently stirred at −90° C. for a further 0.5 h, warmed to −30° C., hydrolyzed with 30 ml of water and acidified with conc. hydrochloric acid, and excess iodine is reduced by addition of sodium hydrogensulphite solution. Customary working-up and recrystallization from hexane gives 21.4 g (41 mmol) of 13. 19.5 g (38 mmol) of 13 are converted into 14 by conversion with sodium trifluoroacetate according to Example 209b Chromatographic purification gives 14.

Example 211b

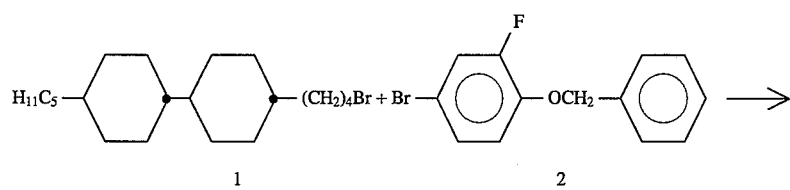

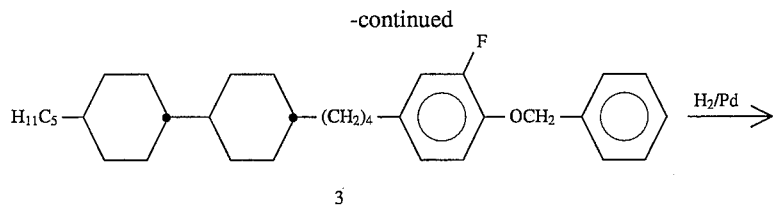

3

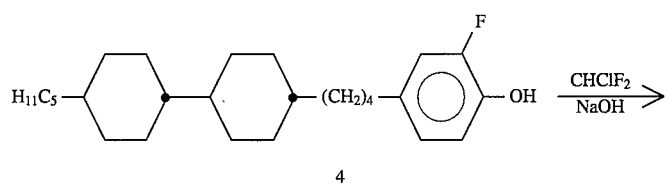

4

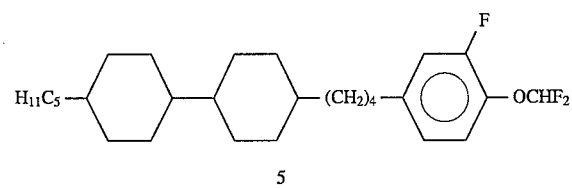

5

According to the above synthesis scheme, the compound 3 is obtained analogously to Example 207b after conversion of 1 into the organozinc compound by a Pd(II)-catalyzed coupling reaction with 2. Hydrogenolytic cleavage of the benzyl ether leads to the phenol 4.

4.0 g (0.01 mol) of this phenol are initially introduced into THF, 3.1 g of 32% sodium hydroxide solution and 0.5 g of tetrabutylammonium hydrogensulphate are added, the mixture is warmed to 50° C. and chlorodifluoromethane is introduced with stirring until it condenses in a condenser cooled with dry ice. After cooling, the THF solution is decanted off from the precipitated oily product and concentrated, and the 5 obtained is recrystallized from ethanol.

Example 212b 25 ml of butyllithium (15% in hexane) are added dropwise at −70° C. to a solution of 15 g of 4-(trans-4-n-propylcyclohexyl)- 2-fluoro-4'-bromobiphenyl in 50 ml of THF and a cooled solution of 4.5 g of $ZnBr_2$ in 25 ml of THF is added after 30 min. After addition of 8.5 g of 1-bromo-3,4,5-triflurobenzene in 75 ml of THF and 0.6 g of $PdCl_2$-dppf, the mixture is allowed to come to room temperature. After stirring for 24 h, the mixture is poured into 100 ml of saturated $NH_4Cl$ solution and worked up as usual. 4"-(trans-4-n-Propylcyclohexyl)-2",3,4,5-tetrafluoroterphenyl is obtained, C 148 N 233 I.

The following are obtained analogously from the corresponding bromoaromatics:
4"-n-propyl-2",3,4,5-tetrafluoroterphenyl
4"-n-pentyl-2",3,4,5-tetrafluoroterphenyl
4'-(trans-4-Methoxymethylcyclohexyl)-3,4,5-trifluorobiphenyl

Example 213b

A mixture of 10.5 g of 1-bromo-3,4,5-trifluorobenzene, 7.4 g of p-ethoxystyrene, 0.25 g of Pd acetate, 0.6 g of tri-o-tolylphosphine, 7 g of triethylamine and 125 ml of acetonitrile is heated at reflux until completion of the reaction. Customary working-up gives 1-(p-ethoxyphenyl)-2-(3,4,5-trifluorophenyl)ethene (C 76 I), which is hydrogenated on Pd-C (5%) in THF to give 1-(p-ethoxyphenyl)-2-(3,4,5-trifluorophenyl)-ethane, C 45 I.

Example 214b 1-(p-Ethoxyphenyl)-2-(3-fluoro-4-benzyloxyphenyl)ethene is obtained from p-ethoxystyrene and the benzyl ether of p-bromo-o-fluorophenol analogously to Example 213. Hydrogenation on Pd-C (5%) in THF gives 1-(p-ethoxyphenyl)- 2-(4-hydroxy-3-fluorophenyl)ethane, of which 41.3 g together with 5.6 g of tetrabutylammonium hydrogensulphate are dissolved in 500 ml of THF at 40° C. 43 g of chlorodifluoromethane are introduced into this solution in such a way that a small amount condenses in the dry ice reflux condenser. 32 g of NaOH (50%) are then added dropwise with vigorous stirring in the course of 10 min. After stirring at 40° for a further hour, the mixture is cooled and decanted off from the oily precipitate formed. After evaporating the solvent, the residue is purified by chromatography and recrystallization. 1-(p-Ethoxyphenyl)-2-(3-fluoro-4-difluoromethoxyphenyl)ethane is obtained, C 43 I.

Example 215b

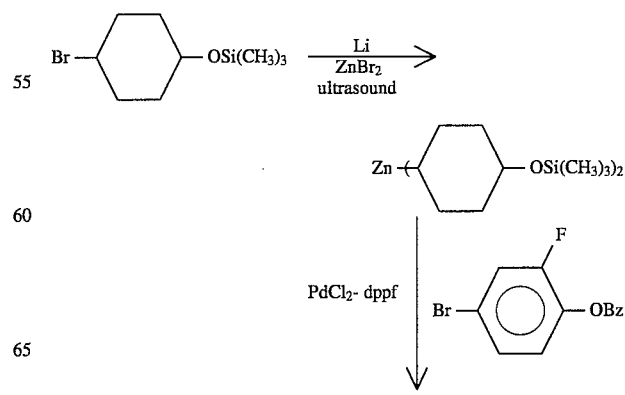

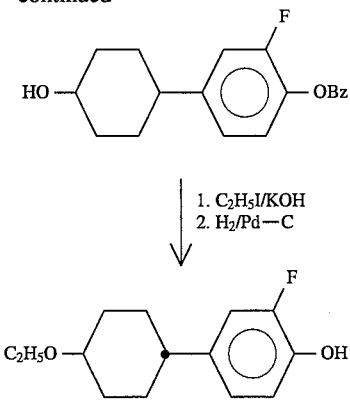

11 g of NaOH (32%) are added to a solution of 8.2 of the resultant p-(trans-4-ethoxycyclohexyl)-o-flurophenol in 80 ml of THF and 13.8 g of chlorodifluoromethane are introduced (dry ice reflux condenser). After subsequently stirring for one hour, the solution is decanted off from the precipitate and concentrated to give a residue. Bulb tube distillation gives p-(trans-4-ethoxycyclohexyl)-o-fluorodifluoromethoxybenzene, b.p.$_1$ ~220° C., Tg −62°.

Example 216b 2-n-Octyloxy-5-(3-fluoro-4-hydroxyphenyl)pyridine [prepared by reaction of 2,5-dibromopyridine with NaH/1-octanol, conversion of the 2-n-octyloxy-5-bromopyridine into the zinc compound (BuLi/ZnBr$_2$/−70°), cross-coupling with 3-fluoro-4-acetoxybromobenzene (PdCl$_2$dppf/THF) and hydrolysis of the acetyl group with KOH/MeOH] gives 2-n-octyloxy-5-(3-fluoro-4-difluoromethoxyphenyl)-pyridine, C 29 I, analogously to Example 214b:

The following are prepared analogously:
2-n-Octyl-5-(3-fluoro-4-difluoromethoxyphenyl)pyridine, C 29 I.

Example A$^2$:

| | | | |
|---|---|---|---|
| PCH-5F | 10.0% | S → N [°C.] | <−40 |
| PCH-6F | 7.0% | Clear point [°C.] | +64 |
| PCH-7F | 15.0% | Viscosity 20° C. | 14 |
| CCP-20CF$_3$ | 10.0% | Δn (589 nm, 20° C.) | 0.0800 |
| CCP-30CF$_3$ | 12.0% | n$_{68}$ (589 nm, 20° C.) | 1.5576 |
| CCP-40CF$_3$ | 8.0% | V$_{(10, 0, 20)}$ | 1.61 |
| CCP-50CF$_3$ | 12.0% | V$_{(50, 0, 20)}$ | 2.04 |
| CCp-3F.F.F | 10.0% | V$_{(90, 0, 20)}$ | 2.66 |
| BCH-5F.F | 16.0% | | |

Example B$^2$:

| | | | |
|---|---|---|---|
| PCH-5F | 12.0% | S → N [°C.] | <−30 |
| PCH-7F | 8.0% | Clear point [°C.] | +80 |
| CCP-20CF$_3$ | 10.0% | Viscosity 20° C. | — |
| CCP-30CF$_3$ | 12.0% | Δn (589 nm, 20° C.) | +0.0756 |
| CCP-40CF$_3$ | 8.0% | n$_{68}$ (589 nm, 20° C.) | 1.5489 |
| CCP-50CF$_3$ | 12.0% | V$_{(10, 0, 20)}$ | 1.66 |
| ECP-3F.F | 12.0% | V$_{(50, 0, 20)}$ | 2.12 |
| CCP-3F.F.F | 14.0% | V$_{(90, 0, 20)}$ | 2.73 |

Example C$^2$:

| | | | |
|---|---|---|---|
| PCH-5F | 12.0% | S → N [°C.] | — |
| PCH-7F | 7.0% | Clear point [°C.] | +78 |
| CCP-20CF$_3$ | 10.0% | Viscosity 20° C. | 16 |
| CCP-30CF$_3$ | 12.0% | Δn (589 nm, 20° C.) | 0.0844 |
| CCP-40CF$_3$ | 8.0% | n$_{68}$ (589 nm, 20° C.) | 1.5610 |
| CCP-50CF$_3$ | 12.0% | V$_{(10, 0, 20)}$ | 1.61 |
| BCP-3F.F | 8.0% | V$_{(50, 0, 20)}$ | 2.06 |
| BCH-5F.F | 6.0% | V$_{(90, 0, 20)}$ | 2.72 |
| CCP-3F.F.F | 13.0% | | |
| CCP-5F.F.F | 12.0% | | |

Example D$^2$:

| | | | |
|---|---|---|---|
| PCH-5F | 12.0% | S → N [°C.] | — |
| PCH-7F | 8.0% | Clear point [°C.] | 77 |
| CCP-20CF$_3$ | 10.0% | Viscosity 20° C. | — |
| CCP-30CF$_3$ | 12.0% | Δn (589 nm, 20° C.) | +0.0847 |
| CCP-40CF$_3$ | 8.0% | n$_{68}$ (589 nm, 20° C.) | 1.5605 |
| CCP-50CF$_3$ | 12.0% | V$_{(10, 0, 20)}$ | 1.59 |
| BCP-3F.F.F | 14.0% | V$_{(50, 0, 20)}$ | — |
| ECCP-3F.F | 12.0% | V$_{(90, 0, 20)}$ | — |
| CCP-5F.F.F | 12.0% | | |

Example E$^2$:

| | | | |
|---|---|---|---|
| PCH-5F | 11.0% | S → N [°C.] | — |
| PCH-7F | 9.0% | Clear point [°C.] | 75 |
| CCP-20CF$_3$ | 8.0% | Viscosity 20° C. | — |
| CCP-30CF$_3$ | 10.0% | Δn (589 nm, 20° C.) | +0.0876 |
| CCP-40CF$_3$ | 7.0% | n$_{68}$ (589 nm, 20° C.) | 1.5666 |
| CCP-50CF$_3$ | 10.0% | V$_{(10, 0, 20)}$ | 1.51 |
| BCP-3F.F | 10.0% | V$_{(50, 0, 20)}$ | 1.95 |
| BCH-5F.F | 10.0% | V$_{(90, 0, 20)}$ | 2.54 |
| CCP-3F.F.F | 13.0% | | |
| CCP-5F.F.F | 12.0% | | |

Example F$^2$:

| | | | |
|---|---|---|---|
| PCH-5F | 12.0% | S → N [°C.] | — |
| PCH-7F | 7.0% | Clear point [°C.] | 76 |
| CCP-20CF$_3$ | 10.0% | Viscosity 20° C. | — |
| CCP-30CF$_3$ | 12.0% | Δn (589 nm, 20° C.) | 0.0835 |
| CCP-40CF$_3$ | 8.0% | n$_{68}$ (589 nm, 20° C.) | 1.5595 |
| CCP-50CF$_3$ | 12.0% | V$_{(10, 0, 20)}$ | 1.49 |
| BCH-3F.F | 8.0% | V$_{(50, 0, 20)}$ | 1.93 |
| BCH-5F.F | 6.0% | V$_{(90, 0, 20)}$ | 2.52 |
| CCP-3F.F.F | 13.0% | | |
| CCP-5F.F.F | 12.0% | | |

Example G$^2$:

| | | | |
|---|---|---|---|
| PCH-5F | 8.0% | S → N [°C.] | — |
| PCH-7F | 4.0% | Clear point [°C.] | 81 |
| CCP-20CF$_3$ | 10.0% | Viscosity 20° C. | — |
| CCP-30CF$_3$ | 12.0% | Δn (589 nm, 20° C.) | +0.0907 |
| CCP-40CF$_3$ | 8.0% | n$_{68}$ (589 nm, 20° C.) | 1.5672 |
| CCP-50CF$_3$ | 12.0% | V$_{(10, 0, 20)}$ | 1.46 |
| BCH-3F.F | 14.0% | V$_{(50, 0, 20)}$ | — |
| BCH-5F.F.F | 10.0% | V$_{(90, 0, 20)}$ | — |
| CCP-3F.F.F | 10.0% | | |
| CCP-5F.F.F | 8.0% | | |
| ECCP-3F.F | 4.0% | | |

Example H$^2$:

| | | | |
|---|---|---|---|
| PCH-5F | 8.0% | S → N [°C.] | — |
| CCP-20CF$_3$ | 10.0% | Clear point [°C.] | 86 |
| CCP-30CF$_3$ | 12.0% | Viscosity 20° C. | — |
| CCP-40CF$_3$ | 8.0% | Δn (589 nm, 20° C.) | +0.0930 |
| CCP-50CF$_3$ | 12.0% | n$_{68}$ (589 nm, 20° C.) | 1.5697 |
| BCH-3F.F | 14.0% | V$_{(10, 0, 20)}$ | 1.45 |
| BCH-5F.F | 11.0% | V$_{(50, 0, 20)}$ | 1.89 |
| CCP-3F.F.F | 12.0% | V$_{(90, 0, 20)}$ | 2.46 |
| CCP-5F.F.F | 7.0% | | |
| ECCP-3F.F | 6.0% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid crystal compound having a terminal structure —A$^2$—Q—CHF$_2$, wherein A$^2$ is 3-fluoro-1,4-phenylene or 3,5-difluoro-1,4-phenylene, and Q is attached to the 4-position of A$^2$ and is —O— or a single bond.

2. A compound according to claim 1, wherein $A^2$ is 3-fluoro-1,4-phenylene.

3. A liquid crystal compound according claim 1, wherein $A^2$ is 3,5-difluoro-1,4-phenylene.

4. A compound according to claim 2, wherein Q is —O—.

5. A compound according to claim 2, wherein Q is a single bond.

6. A compound according to claim 3, wherein Q is —O—.

7. A compound according to claim 3, wherein Q is a single bond.

8. In a liquid crystal medium containing at least two components, the improvement wherein one of said components is at least one compound according to claim 1.

9. In an electrooptical display containing a liquid crystal medium, the improvement wherein said medium is a medium according to claim 8.

10. A compound according to claim 3, wherein said terminal structure —$A^2$—Q—$CHF_2$ is attached to the remainder of said liquid crystal compound by group $Z^1$, wherein $Z^1$ is —CO—O—, —O—CO—, —$CH_2$O—, —$OCH_2$—, —$CH_2CH_2$—, —CH=CH— or —C≡C—.

11. A compound according to claim 3, wherein said terminal structure —$A^2$—Q—$CHF_2$ is attached to the remainder of said liquid crystal compound by group $A^1$, wherein
$A^1$ is
   (a) trans-1,4-cyclohexylene or trans-1,4-cyclohexylene in which one or more non-adjacent $CH_2$ groups is, in each case, replaced by —O— or —S—,
   (b) 1,4-phenylene or 1,4-phenylene in which one or two CH groups are each replaced by N,
   (c) 1,4-cyclohexenylene, 1,4-bicyclo[2.2.2]-octylene, piperidine-1,4-diyl, naphthalene-2,6-diyl, decahydronaphthalene- 2,6-diyl or and 1,2,3,4-tetrahydronaphthalene-2,6-diyl, in which the radicals of (a) and (b) can, in each case, be substituted by CN or fluorine.

12. A compound according to claim 3, wherein said terminal structure —$A^2$—Q—$CHF_2$ is attached to the remainder of the liquid crystal compound by group —$A^1$—$Z^1$—, wherein
$Z^1$ is —CO—O—, —O—CO—, —$CH_2$O—, —$OCH_2$—, —$CH_2CH_2$—, —CH=CH—, —C≡C— or a single bond; and $A^1$ is
   (a) trans-1,4-cyclohexylene or trans-1,4-cyclohexylene in which one or more non-adjacent $CH_2$ groups is, in each case, replaced by —O— or —S—,
   (b) 1,4-phenylene or 1,4-phenylene in which one or two CH groups are each replaced by N,
   (c) 1,4-cyclohexenylene, 1,4-bicyclo[2.2.2]-octylene, piperidine-1,4-diyl, naphthalene-2,6-diyl, decahydronaphthalene- 2,6-diyl or and 1,2,3,4-tetrahydronaphthalene-2,6-diyl, in which the radicals of (a) and (b) may, in each case, be substituted by CN or fluorine.

13. A compound according to claim 10, wherein $Z^1$ is —CO—O—, —O—CO—, —$CH_2CH_2$—, —$CH_2$O— or —$OCH_2$—.

14. A compound according to claim 12, wherein $Z^1$ is —CO—O—, —O—CO—, —$CH_2CH_2$—, —$CH_2$O—, —$OCH_2$— or a single bond.

15. A compound according to claim 11, wherein $A^1$ is 1,4-phenylene, trans-1,4-cyclohexylene, 1,4-cyclohexenylene, pyrimidine- 2,5-diyl or 1,3-dioxane-2,5-diyl.

16. A compound according to claim 12, wherein $A^1$ is 1,4-phenylene, trans-1,4-cyclohexylene, 1,4-cyclohexenylene, pyrimidine- 2,5-diyl or 1,3-dioxane-2,5-diyl.

* * * * *